(12) United States Patent
Curatolo et al.

US007887840B2

(10) Patent No.: US 7,887,840 B2
(45) Date of Patent: Feb. 15, 2011

(54) PHARMACEUTICAL COMPOSITIONS COMPRISING DRUG AND CONCENTRATION-ENHANCING POLYMERS

(75) Inventors: William J. Curatolo, Niantic, CT (US); Dwayne T. Friesen, Bend, OR (US)

(73) Assignee: Bend Research, Inc., Bend, OR (US)

( * ) Notice: Subject to any disclaimer, the term of this patent is extended or adjusted under 35 U.S.C. 154(b) by 2511 days.

(21) Appl. No.: 10/176,462

(22) Filed: Jun. 20, 2002

(65) Prior Publication Data

US 2003/0072801 A1 Apr. 17, 2003

Related U.S. Application Data

(60) Provisional application No. 60/300,314, filed on Jun. 22, 2001.

(51) Int. Cl.
*A61K 9/20* (2006.01)
*A61K 31/715* (2006.01)
*A61K 31/56* (2006.01)

(52) U.S. Cl. ............................ 424/465; 514/58; 514/171
(58) Field of Classification Search .................. 514/171
See application file for complete search history.

(56) References Cited

U.S. PATENT DOCUMENTS

| | | | |
|---|---|---|---|
| 4,344,934 A | 8/1982 | Martin et al. ................. 424/80 |
| 4,610,875 A | 9/1986 | Panoz et al. .................. 424/80 |
| 4,769,236 A | 9/1988 | Panoz et al. .................. 424/80 |
| 4,880,623 A | 11/1989 | Piergiorgio et al. ............ 424/78 |
| 5,008,114 A | 4/1991 | Lovrecich .................... 424/484 |
| 5,071,643 A | 12/1991 | Yu et al. ...................... 514/570 |
| 5,093,372 A | 3/1992 | Uedo et al. ................... 514/687 |
| 5,134,127 A | 7/1992 | Stella et al. ................... 514/58 |
| 5,145,684 A * | 9/1992 | Liversidge et al. ........... 424/489 |
| 5,225,192 A | 7/1993 | Lovrecich ................... 424/78.02 |
| 5,275,824 A | 1/1994 | Carli et al. ................... 424/490 |
| 5,354,560 A | 10/1994 | Lovrecich .................... 424/489 |
| 5,360,615 A | 11/1994 | Yu et al. ...................... 424/455 |
| 5,376,645 A | 12/1994 | Stella et al. ................... 514/58 |
| 5,376,688 A | 12/1994 | Morton et al. ................ 514/786 |
| 5,405,616 A | 4/1995 | Wunderlich et al. .......... 424/451 |
| 5,449,521 A | 9/1995 | Lovrecich .................... 424/489 |
| 5,456,923 A | 10/1995 | Nakamichi et al. ........... 424/489 |
| 5,560,924 A | 10/1996 | Wunderlich et al. .......... 424/451 |
| 5,560,932 A | 10/1996 | Bagchi et al. ................ 424/489 |
| 5,569,452 A | 10/1996 | Amidon et al. .............. 424/78.1 |
| 5,569,469 A | 10/1996 | Lovrecich .................... 424/501 |
| 5,645,856 A | 7/1997 | Lacy et al. ................... 424/455 |
| 5,686,133 A | 11/1997 | Amidon et al. ............. 427/2.22 |
| 5,834,022 A | 11/1998 | Amidon et al. .............. 424/492 |
| 5,851,275 A | 12/1998 | Amidon et al. ............ 106/148.1 |
| 5,858,410 A | 1/1999 | Muller et al. ................ 424/489 |
| 5,874,029 A | 2/1999 | Subramaniam et al. ....... 264/12 |
| 5,874,418 A | 2/1999 | Stella et al. ................... 514/58 |
| 5,880,095 A | 3/1999 | Park et al. ..................... 514/12 |
| 5,925,645 A | 7/1999 | Schmidt et al. .............. 514/277 |
| 5,932,587 A | 8/1999 | Schmeck et al. ............. 514/278 |
| 5,993,858 A | 11/1999 | Crison et al. ................. 424/490 |
| 6,042,847 A | 3/2000 | Kerc et al. ................... 424/472 |
| 6,046,177 A | 4/2000 | Stella et al. .................... 514/58 |
| 6,054,136 A | 4/2000 | Farah et al. .................. 424/400 |
| 6,069,148 A | 5/2000 | Schmidt et al. .............. 514/277 |
| 6,096,338 A | 8/2000 | Lacy et al. ................... 424/455 |
| 6,117,949 A * | 9/2000 | Rathi et al. .................. 525/415 |
| 6,127,383 A | 10/2000 | Schmidt et al. .............. 514/312 |
| 6,140,342 A | 10/2000 | Goldstein et al. ............ 514/313 |
| 6,140,343 A | 10/2000 | DeNinno et al. ............. 514/313 |
| 6,147,090 A | 11/2000 | DeNinno et al. ............. 514/313 |
| 6,177,103 B1 | 1/2001 | Pace et al. ................... 424/489 |
| 6,197,349 B1 | 3/2001 | Westesen et al. ............. 424/501 |
| 6,197,786 B1 | 3/2001 | DeNinno et al. ............. 514/313 |
| 6,207,671 B1 | 3/2001 | Schmidt et al. .............. 514/277 |
| 6,228,894 B1 | 5/2001 | Rinaldi et al. ................ 514/951 |
| 6,232,304 B1 * | 5/2001 | Kim et al. ..................... 514/58 |
| 6,310,075 B1 | 10/2001 | DeNinno et al. ............. 514/313 |
| 6,586,613 B1 | 7/2003 | Brandes et al. .............. 556/449 |
| 6,958,346 B2 | 10/2005 | Stoltefuss et al. ............ 514/278 |
| 2001/0018446 A1 | 8/2001 | Sikorski et al. .............. 514/357 |
| 2001/0028895 A1 | 10/2001 | Bisgaier et al. .............. 424/450 |
| 2002/0006443 A1 | 1/2002 | Curatolo et al. .............. 424/486 |
| 2003/0054038 A1 | 3/2003 | Crew et al. .................. 424/486 |
| 2003/0091643 A1 | 5/2003 | Friesen et al. ............... 424/486 |

FOREIGN PATENT DOCUMENTS

EP 0605497 9/1992

(Continued)

OTHER PUBLICATIONS

Baraldi et al., J. Med Chem., vol. 41, No. 17, pp. 3174-3185, 1998.
Usue, et al., International Journal of Pharmaceutics 154, 1997, pp. 59-66.
Bodmeier, J. of Microencapsulation, vol. 8, No. 2, pp. 161-170, 1991.
Fenyvest et al, Pharmacie, vol. 39, p. 473, 1984.
Gordon, D. J., et al., Circulation, vol. 79, No. 1, pp. 8-15, Jan. 1989, "High-Density Lipoprotein Cholesterol and Cardiovascular Disease, Four Prospective American Studies."
Gordon, David J., Circulation, vol. 79, No. 1, Jan. 1989, pp. 8-15.
U.S. Appl. No. 10/459,808, filed Jun. 10, 2003.
U.S. Appl. No. 10/173,945, filed Jun. 17, 2002.
U.S. Appl. No. 09/495,061, filed Jan. 31, 2000.
U.S. Appl. No. 09/495,059, filed Jan. 31, 2000.
US 6,586,613 English equivalent to WO 99/14174.
US 6,958,346 English equivalent to WO 99/14215.
JP 10287662 English Abstract (attached).
JP H02-149518A with English translation.

*Primary Examiner*—Michael G Hartley
*Assistant Examiner*—Nabila G Ebrahim
(74) *Attorney, Agent, or Firm*—Chernoff, Vilhauer, McClung & Stenzel

(57) ABSTRACT

A solubility-improved drug form is combined with a concentration-enhancing polymer in a sufficient amount so that the combination provides substantially enhanced drug concentration in a use environment relative to a control comprising the same amount of the same drug form without the concentration-enhancing polymer.

10 Claims, No Drawings

FOREIGN PATENT DOCUMENTS

| | | | |
|---|---|---|---|
| EP | 0796846 | | 7/1997 |
| EP | 0801060 | | 10/1997 |
| EP | 0818197 | | 1/1998 |
| EP | 0818448 | | 1/1998 |
| EP | 0852140 | | 7/1998 |
| EP | 0901786 | | 3/1999 |
| EP | 1027886 | * | 2/2000 |
| EP | 0992496 | | 4/2000 |
| EP | 1020439 | | 7/2000 |
| EP | 1027885 | | 8/2000 |
| EP | 1027886 | | 8/2000 |
| EP | 1027887 | | 8/2000 |
| EP | 1160330 | | 12/2001 |
| GB | 2305665 | | 4/1997 |
| JP | 10287662 | | 10/1998 |
| WO | WO8300809 | | 3/1983 |
| WO | WO9839299 | | 9/1998 |
| WO | WO9914174 | | 3/1999 |
| WO | WO9914204 | | 3/1999 |
| WO | WO9914215 | | 3/1999 |
| WO | WO 9940061 A2 | * | 8/1999 |
| WO | WO9941237 | | 8/1999 |
| WO | WO0017164 | | 3/2000 |
| WO | WO 00/18724 | * | 4/2000 |
| WO | WO0018721 | | 4/2000 |
| WO | WO0018723 | | 4/2000 |
| WO | WO0018724 | | 4/2000 |
| WO | WO-00/38725 | * | 7/2000 |
| WO | WO0072825 | | 12/2000 |
| WO | WO0147495 | | 7/2001 |
| WO | WO0168055 | | 9/2001 |
| WO | WO0168092 | | 9/2001 |
| WO | WO02056878 | | 7/2002 |

* cited by examiner

PHARMACEUTICAL COMPOSITIONS COMPRISING DRUG AND CONCENTRATION-ENHANCING POLYMERS

This application claims the benefit of priority of provisional Patent Application Ser. No. 60/300,314 filed Jun. 22, 2001.

BACKGROUND OF THE INVENTION

Generally, the invention relates to pharmaceutical compositions of drugs and concentration-enhancing polymers which increase the drug concentration in a use environment and thus increase bioavailability.

Low-solubility drugs often show poor bioavailability or irregular absorption, the degree of irregularity being affected by factors such as dose level, fed state of the patient, and form of the drug. Increasing the bioavailability of low-solubility drugs has been the subject of much research. Increasing bioavailability hinges on improving the concentration of the drug in solution to improve absorption.

It is known that many low-solubility drugs can be formulated so as to increase the maximum concentration of the drug that will dissolve in an aqueous solution in in vitro tests. One such approach is to grind the drug down to less than 400 nm to form so-called nanoparticles. The nanoparticles contain a discrete phase of a drug with a surface modifier adsorbed to the surface. When such a drug in a nanoparticle form is initially administered to an environment of use, such as in gastric fluid, the nanoparticle form of the drug may lead to increased bioavailability. See U.S. Pat. No. 5,145,684, herein incorporated by reference.

Another drug delivery technology used to increase concentration of a drug in a use environment is to incorporate the drug into particles of a water-swellable but insoluble crosslinked polymer, contacting this composition with a solvent, in gaseous or liquid form, which is able to swell the polymer, and then drying the product under vacuum. See U.S. Pat. No. 5,569,469, incorporated herein by reference in its entirety.

Yet another drug delivery technology converts the bulk crystalline drug into an amorphous nanoparticle. Essentially, a suspension of drug in solvent is fed into a chamber, where it is rapidly mixed with another solvent. The drug substance suspension is converted into a molecular solution. The admixture of an aqueous solution of a polymer induces precipitation of the drug. The polymer keeps the drug substance particles in their nanoparticulate state and prevents them from aggregation or growth. Water redispersable dry powders can be obtained from the nanosized dispersion by conventional methods. See U.S. Pat. No. 6,197,349 also incorporated by reference.

Another drug delivery technology of increasing dissolution rate of drug in a use environment is through incorporating the drug in a nanosuspension. See U.S. Pat. No. 5,858,410, herein incorporated by reference. A nanosuspension is a suspension of nanosized (typically 10 nm to 1000 nm) particles of at least one active therapeutic.

U.S. Pat. No. 6,177,103, herein incorporated by reference, discloses a process for preparing stabilized suspensions of water insoluble drugs with an average particle size of 50 nm to about 2000 nm. The suspensions are prepared by rapid expansion of a solution of the drug, surface modifier and a liquefied gas (e.g., a supercritical fluid) into an aqueous medium. The aqueous suspension may also be homogenized using a high-pressure homogenizer. See also U.S. Pat. No. 5,858,410 also incorporated by reference.

U.S. Pat. No. 5,560,932, herein incorporated by reference, discloses a process for preparing extremely small particles with average particle diameters of less than 400 nm by homogeneous nucleation and precipitation in the presence of a surface modifier.

Stabilizing the amorphous form of a drug by spray-drying the drug in the presence of a stabilizer to inhibit crystal growth is also known to increase solubility of low solubility drugs. See U.S. Pat. Nos. 4,769,236 and 4,610,875, both of which are herein incorporated by reference.

U.S. Pat. Nos. 5,851,275 and 5,686,133, herein incorporated by reference, disclose another drug delivery technology for increasing the dissolution rate of poorly soluble drugs by coating them with a combination of gelatin and lecithin.

In all of the above cases, the methods often provide an increase in dissolution rate and/or a temporary increase in the solubility of the drug in a use environment.

Increasing drug solubilization by using combinations of drug and polymer has been described. For example, Martin et al., U.S. Pat. No. 4,344,934 mixed poorly soluble drugs with polymers such as hydroxypropyl methyl cellulose (HPMC) and added an aqueous surfactant solution to the drug-polymer mixture. While this results in improved dissolution, there is only slight enhancement of drug concentration relative to the equilibrium concentration. Piergiorgio et al., U.S. Pat. No. 4,880,623 used solvent processing to co-precipitate nifedipine with PEG and adsorbed this onto polymers such as HPMC, or onto other excipients. While increased drug bioavailability in a controlled release dosage form, relative to the commercial product nifedipine. ADALAT AR, was observed, no direct comparison was made between coprecipitated and noncoprecipitated drug forms. Uedo et al., U.S. Pat. No. 5,093,372 mixed the sparingly-soluble drug exifone with polymers such as HPMC to increase bioavailability. However, the results were reported to be unique for exifone formulations, and the exifone was not in a solubility-improved form.

Usui, et al., *Inhibitory Effects of Water-soluble Polymers on Precipitation of RS*-8359, Int'l J. of Pharmaceutics 154 (1997) 59-66, discloses the use of three polymers, namely hydroxy propyl methyl cellulose, hydroxy propyl cellulose, and polyvinylpyrrolidone to inhibit precipitation of the low-solubility drug RS-8359. The drug and polymer were dissolved in a mixture of 0.5 N HCl and methanol, and then added to a phosphate buffer solution. Usui et al. observed that the particular polymers inhibited crystallization of the drug.

Nevertheless, what is still needed is a composition comprising a low-solubility drug that provides enhanced concentration of the drug in aqueous solution and/or that enhances the bioavailability of the drug. These needs and others that will become apparent to one of ordinary skill in the art are met by the present invention, which is summarized and described in detail below.

SUMMARY OF THE INVENTION

The invention relates to compositions comprising a combination of a drug in a solubility-improved form and at least one concentration-enhancing polymer that enhances the concentration of the drug in a use environment relative to control compositions that are free from the concentration-enhancing polymer. The terms "solubility-improved" and "solubility-improved drug form" as employed herein refer to a form of the drug that has increased solubility or dissolution rate relative to the least soluble form of the drug known. Thus, the term implies that a less soluble or more slowing dissolving form of the drug exists and is either known or has been determined, i.e., known, for example, from the scientific or patent literature, or determined by or otherwise known to the investigator. The drug in the solubility-improved form provides a dissolved drug concentration in a use environment that exceeds, at least temporarily, the equilibrium concentration of the drug in the use environment. By "equilibrium concentration" is meant the dissolved drug concentration provided by the lowest solubility form of the drug alone, either crystalline or amorphous, in the use environment. In other words, the solubility-improved form is capable of achieving, at least temporarily, a supersaturated concentration of said drug in said use environment. Where the lowest solubility form of the drug provides a drug concentration that decreases slowly with respect to time in the use environment, it may be difficult to establish the lowest dissolved drug value that would represent the equilibrium concentration of the drug. In such cases, the equilibrium concentration of drug may be taken as the dissolved drug concentration in the use environment 20 hours after introduction of the drug to the use environment. A solubility-improved drug form also includes formulations that increase the rate of dissolution of the drug, leading to an initially higher concentration of drug in solution, at least temporarily, compared with the drug in its lowest solubility form.

A solubility-improved drug form may consist of a highly soluble form of the drug alone, may be a composition comprising a highly soluble form of the drug plus inert excipients, or may be a composition comprising the drug in a poorly or highly soluble form and one or more excipients which have the effect of increasing the solubility of the drug, regardless of the length of time for which the solubility is increased. Examples of "solubility-improved drug forms" include but are not limited to: (1) drug in microparticulate form; (2) drug in nanoparticulate form; (3) absorbed drug; (4) drug in a nanosuspension; (5) a supercooled melt of drug; (6) cyclodextrin/drug form; (7) softgel form; (8) gelatin form, (9) self-emulsifying form; and (10) three-phase drug form. (The drug in the solubility-improved form is . . . sometimes referred to herein as simply "drug form.")

An object of the invention is to provide a pharmaceutically acceptable composition comprising (a) a drug in a solubility-improved form; and (b) a concentration-enhancing polymer combined with the drug in a sufficient amount so that the composition provides, after introduction to a use environment, a dissolution area under the concentration versus time curve ("AUC"), for any period of at least 90 minutes between the time of introduction into the use environment and about 270 minutes following introduction to the use environment that is at least 1.25-fold the corresponding AUC provided by a control composition, wherein the control composition is an equivalent quantity of the drug in the same solubility-improved form alone, but free from a concentration enhancing polymer.

Yet another object of the invention is to provide a pharmaceutically acceptable composition comprising (a) a drug in a solubility-improved form; and (b) a concentration-enhancing polymer combined with the drug in a sufficient amount so that the composition provides, after introduction to a use environment, a relative bioavailability of at least 1.25 relative to a control composition of an equivalent quantity of the drug in the same solubility-improved form alone but free from a concentration-enhancing polymer.

A method is also provided of administering a drug comprising co-administering: (a) a drug in a solubility-improved form; and (b) a concentration-enhancing polymer; wherein the concentration-enhancing polymer is co-administered with the drug in a sufficient amount so that, after introduction to a use environment, a dissolution area under the concentration versus time curve in the use environment for any period of at least 90 minutes between the time of introduction into the use environment and about 270 minutes following introduction to the use environment that is at least 1.25-fold the corresponding area under the curve provided by a control composition; and wherein the control composition is an equivalent quantity of the drug in the same solubility-improved form alone, but free from the concentration-enhancing polymer.

Also provided by the invention is a method of administering a drug comprising co-administering to a patient in need of the drug (a) a drug in a solubility-improved form; and (b) a concentration-enhancing polymer; wherein the concentration-enhancing polymer is co-administered with the drug in a sufficient amount so that, after introduction to a use environment, a relative bioavailability is provided of at least 1.25 relative to a control composition, and wherein the control composition is an equivalent quantity of the drug in the same solubility-improved form alone, but free from the concentration-enhancing polymer.

The various aspects of the present invention have one or more of the following advantages.

The solubility-improved drug form, when administered to a use environment, provides an initial concentration of drug that exceeds the equilibrium concentration of drug, while the concentration-enhancing polymer retards the rate at which the initially enhanced drug concentration falls to the equilibrium concentration. In addition, because in some cases the drug form may dissolve at a rate that is slow relative to the rate that the drug converts to a less soluble form in the absence of the polymer, the presence of the polymer often allows the drug to achieve a higher concentration than that obtained in the absence of the polymer. The result is that the compositions of the present invention provide an improved dissolution area-under-the-curve ("AUC") that is greater than that provided by the solubility-improved form of the drug alone. While not required to be within the scope of the present invention, in some aspects, the drug form provides a maximum drug concentration that exceeds the maximum drug concentration achieved by the drug in the solubility-improved form alone. Nevertheless, the advantages of the invention may be obtained by merely retarding the rate at which the enhanced drug concentration falls to the equilibrium concentration, even without increasing the maximum drug concentration relative to the drug form alone.

Improving the dissolution AUC has the consequence that the compositions of the present invention may also provide enhanced bioavailability of the drug by increasing the concentration of drug that remains dissolved in the use environment, particularly in the GI tract. Improving the concentration of the drug in solution allows higher blood levels to be achieved, in some cases enabling an effective level to be reached or in other cases, allowing effective blood levels to be reached at lower drug dosage levels, which in turn decreases the amount of drug that must be dosed, reduces the blood level variability, and also decreases the size of the dosage form depending on the amount of polymer needed. Accordingly, the compositions of the present invention enable the effective use of drugs having low aqueous solubility which otherwise do not have a sufficiently high bioavailability, to be effective, and also enhance bioavailability to reduce the required dose.

Furthermore, because the compositions of the present invention provide for a higher drug concentration in the use environment, and because once a high drug concentration is achieved the concentration tends to remain high due to inhibition of precipitation or crystallization of the drug, they reduce the adverse effects of chemical species present in the use environment such as chloride or hydrogen ions or bile salts on the absorption of drug. Thus, in cases where the use environment is the GI tract, the compositions of the present invention will show less variability on the fed/fast state of the human or animal.

It is known that the solubility-improved drug forms described below are formulated to provide an initially enhanced aqueous concentration of the drug relative to the equilibrium concentration of the lowest-solubility form of the drug. However, in the absence of the concentration-enhancing polymer, the initially enhanced drug concentration can often quickly decrease, approaching the equilibrium concentration of the drug as the drug precipitates or crystallizes from solution, thereby limiting drug absorption.

The key to the present invention was the recognition by the inventors that the initially enhanced concentration of the drug in solution provided by a drug form could be maintained, and in some cases enhanced, by retarding precipitation, crystallization, or conversion of the drug to lower solubility forms through the use of a concentration-enhancing polymer. Thus, without implying any particular mechanism of action, it is believed that the concentration-enhancing polymers of this invention may be viewed as acting as crystallization or precipitation inhibitors. Surprisingly, this may be accomplished by simply combining the concentration-enhancing polymer with the drug form. Alternatively, the concentration-enhancing polymer can be coated onto drug-containing tablets or beads or even administered separately but to the same use environment as the drug form and still function to maintain for a substantial time period a greater than equilibrium drug concentration and, in turn, a higher bioavailability.

The drug form and concentration-enhancing polymer may be "simple physical mixtures" when they are combined using conventional mixing techniques such as combining and physically stirring dry components together or mixing by dry- or wet-granulating. Thus, a simple physical mixture of the drug form and concentration-enhancing polymer means that in the mixture, the drug form substantially retains its properties, such as a melting point or glass transition temperature, that match those properties of the drug in the solubility-improved form alone. The concentration-enhancing polymer may also be incorporated into the drug form.

The drug form and the concentration-enhancing polymer can also be combined via co-administration of the two components to a use environment. By co-administration is meant that the drug form is administered separately from, but within the same general time frame, as the concentration-enhancing polymer. For example, the drug form can be administered in its own dosage form that is taken at approximately the same time as the concentration-enhancing polymer, which is in a separate dosage form. The time difference between administration of the drug form and the concentration-enhancing polymer is such that they come into physical contact in the use environment. When they are not co-administered at the same time it is generally preferable to administer the concentration-enhancing polymer prior to administration of the drug form.

The various aspects and embodiments of the invention may be described as follows.

In a first aspect, the invention relates to a composition comprising:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer wherein said concentration-enhancing polymer is present in a sufficient amount so that said composition provides, after introduction to said use environment, a maximum concentration of said drug in said use environment that is at least 1.25-fold a maximum concentration of said drug provided by a control composition, wherein said control composition is an equivalent quantity of said drug in said solubility-improved form alone.

In a second aspect, the invention relates to a composition comprising:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer;

wherein said concentration-enhancing polymer is present in a sufficient amount so that said composition provides, after introduction to a use environment, a dissolution area under the concentration versus time curve for any period of at least 90 minutes between the time of introduction into the use environment and about 270 minutes following introduction to the use environment that is at least 1.25-fold the corresponding area under the curve provided by a control composition, wherein said control composition is an equivalent quantity of said drug in said solubility-improved form alone.

In a third aspect, the invention relates to a composition comprising:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer;

wherein said concentration-enhancing polymer is present in a sufficient amount so that said composition provides, after introduction to said use environment, a relative bioavailability of at least 1.25 relative to a control composition, wherein said control composition is an equivalent quantity of said drug in said solubility-improved form alone.

In further independent embodiments of the first, second and third aspects of the invention, the solubility-improved drug form is selected from the group consisting of drug in microparticulate form, drug in nanoparticulate form, absorbed drug, drug in a nanosuspension, a supercooled melt of drug, cyclodextrin/drug form, softgel form, gelatin form, self-emulsifying form, and three-phase drug form.

In further independent embodiments of the first, second and third aspects of the invention, the drug is in nanoparticulate form. The nanoparticulate form of the drug may comprise particles of 10% to 99.9% by weight of a crystalline drug substance having a solubility in water of less than 10 mg/ml, said drug substance having an effective average particle size of less than about 400 nm. In one embodiment, nanoparticulate form of the drug consists essentially of 10% to 99.9% by weight of a crystalline drug substance having a solubility in water of less than 10 mg/mL, said drug substance having a non-crosslinked surface modifier adsorbed on the surface thereof in an amount of 0.1 to 90% by weight and sufficient to maintain an effective average particle size of less than about 400 nm.

In further independent embodiments of the first, second and third aspects of the invention, the drug is selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, antiatherosclerotic agents, glycogen phosphorylase inhibitors, cholesterol ester transfer protein inhibitors and immune suppressants.

In further independent embodiments of the first, second and third aspects of the invention, the drug is a glycogen phosphorylase inhibitor selected from the group consisting of [R-(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide.

In even further independent embodiments of the first, second and third aspects of the invention, the drug is a cholesterol ester transfer protein inhibitor selected from the group consisting of [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester; or a compound which is [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester; or a compound which is [2R,4S]4-[(3,5-Bis-trifluoromethyl-benzyl)-methoxycarbonyl-amino]-2-ethyl-6-trifluoromethyl-3,4-dihydro-2H-quinoline-1-carboxylic acid isopropyl ester In even further independent embodiments of the first, second and third aspects of the invention, the use environment is in vivo. In these embodiments, the use environment my be selected from the group consisting of the GI tract, subdermal, intranasal, buccal, intrathecal, ocular, intraaural, subcutaneous space, vaginal tract, pulmonary tract, arterial and venous blood vessels, and intramuscular tissue of an animal.

In further independent embodiments of the first and second aspects of the invention, the use environment is in vitro.

In further independent embodiments of the first and second aspects of the invention, the concentration-enhancing polymer has a hydrophobic portion and a hydrophilic portion.

In further independent embodiments of the first, second and thirds aspects of the invention, the concentration-enhancing polymer is a ionizable cellulosic polymer. In these embodiments, the polymer may be selected from the group consisting of hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, ethyl carboxymethyl cellulose, carboxymethyl cellulose, carboxymethyl ethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

In further independent embodiments of the first, second and third aspects of the invention, the polymer is a non-ionizable cellulosic polymer. In these embodiments, the polymer may be selected from the group consisting of hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

In further independent embodiments of the first, second and third aspects of the invention, the polymer is an ionizable, non-cellulosic polymer. In these embodiments, the polymer may be selected from the group consisting of carboxylic acid functionalized polymethacrylates, carboxylic acid functionalized polyacrylates, amine-functionalized polyacrylates, amine-fuctionalized polyacrylates and polymethacrylates, proteins, and carboxylic acid functionalized starches.

In further, independent embodiments of the first, second and third aspects of the invention, the polymer is a non-ionizable, non-cellulosic polymer. In these embodiment, the polymer may be selected from the group consisting of vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alky- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; and polyethylene polyvinyl alcohol copolymers and polyoxyethylene-polyoxypropylene block copolymers.

In further independent embodiments of the first, second and third aspects of the invention, the concentration-enhancing polymer is a neutralized acidic polymer.

In further independent embodiments of the first, second and third aspects of the invention, the solubility-improved form is a cyclodextrin/drug form. In these embodiments, the drug may be ziprasidone.

In a fourth aspect, the invention relates to a method of administering a low-solubility drug comprising co-administering:

(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and (b) a concentration-enhancing polymer;

wherein said concentration-enhancing polymer is co-administered with said drug in a sufficient amount, so that after introduction to said use environment, a maximum concentration of said drug in said use environment is provided that is at least 1.25-fold a maximum concentration of said drug provided by a control composition, wherein said control composition is an equivalent quantity of said drug in said solubility-improved form alone.

In a fifth aspect, the invention relates to a method of administering a low-solubility drug comprising co-administering:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer;

wherein said concentration-enhancing polymer is co-administered with said drug in a sufficient amount so that, after introduction to said environment, a dissolution area under the concentration versus time curve for any period of at least 90 minutes between the time of introduction into the use environment and about 270 minutes following introduction to the use environment is provided that is at least 1.25-fold the corresponding area under the curve provided by a control composition;

and wherein said control composition is an equivalent quantity of said drug in said solubility-improved form alone.

In a sixth aspect, the invention relates to a method of administering a low-solubility drug comprising co-administering:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer;

wherein said concentration-enhancing polymer is co-administered with said drug in a sufficient amount so that, after introduction to said use environment, a relative bioavailability is provided that is at least 1.25-fold that of a control composition, wherein said control composition is an equivalent quantity of said drug in said solubility-improved form alone.

In further independent embodiments of the fourth, fifth and sixth aspects of the invention, the solubility-improved drug form is selected from the group consisting of in nanoparticulate form, absorbed drug, drug in a nanosuspension, a supercooled melt of drug, cyclodextrin/drug form, softgel form, self-emulsifying form, and three-phase drug form.

In further independent embodiment of the fourth, fifth, and sixth aspects of the invention, the drug is in nanoparticulate form. The nanoparticulate form of the drug may comprise particles of 10% to 99.9% by weight of a crystalline drug substance having a solubility in water of less than 10 mg/ml, said drug substance having an effective average particle size of less than about 400 nm. In one embodiment, nanoparticulate form of the drug consists essentially of 10% to 99.9% by weight of a crystalline drug substance having a solubility in water of less than 10 mg/mL, said drug substance having a non-crosslinked surface modified adsorbed on the surface thereof in an amount of 0.1 to 90% by weight and sufficient to maintain an effective particle size of less than about 400 nm.

In further independent embodiments of the fourth, fifth and sixth aspects of the invention, the drug may be selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, antiatherosclerotic agents, glycogen phosphorylase inhibitors, and cholesterol ester transfer protein inhibitors.

In further independent embodiments of the fourth, fifth and sixth aspects of the invention, the drug is a glycogen phosphorylase inhibitor selected from the group consisting of [R-(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide.

In further independent embodiments of the fourth, fifth and sixth aspects of the invention, the drug is a cholesterol ester transfer protein inhibitor selected from the group consisting of [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester; or a compound which is [2R,4S]4-[acetyl-(3,5-bis-trifluoromethyl-benzyl)amino]-2-ethyl-6-trifluoromethyl-3,4-dihydro-2H-quinoline-1-carboxylic acid isopropyl ester; or a compound which is [2R,4S] 4-[(3,5-Bis-trifluoromethyl-benzyl)methoxycarbonyl-amino]-2-ethyl-6-trifluoromethyl-3,4-dihydro-2H-quinoline-1-carboxylic acid isopropyl ester.

In further independent embodiments of the fourth, fifth and sixth aspects of the invention, the use environment is in vivo. In these embodiments, the use environment may be selected from the group consisting of the GI tract, subdermal, intranasal, buccal, intrathecal, ocular, intraaural, subcutaneous space, vaginal tract, pulmonary tract, arterial and venous blood vessels, and intramuscular tissue of an animal.

In further embodiments of the fourth and fifth aspects of the invention, the use environment is in vitro.

In further independent embodiments of the fourth, fifth and sixth embodiments of the invention, the concentration-enhancing polymer has a hydrophobic portion and a hydrophilic portion.

In further independent embodiments of the fourth, fifth and sixth embodiments of the invention, the concentration-enhancing polymer is a ionizable cellulosic polymer. In these embodiments, the polymer may be selected from the group consisting of hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, ethyl carboxymethyl cellulose, carboxymethyl cellulose, carboxymethyl ethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

In further independent embodiments of the fourth, fifth and sixth embodiments of the invention, the polymer is a non-ionizable cellulosic polymer. In these embodiments, the polymer may be selected from the group consisting of hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

In further independent embodiments of the fourth, fifth and sixth embodiments of the invention, the polymer is an ionizable, non-cellulosic polymer.

In these embodiments, the polymer may be selected from the group consisting of carboxylic acid functionalized polymethacrylates, carboxylic acid functionalized polyacrylates, amine-functionalized polyacrylates, amine-fuctionalized polyacrylates and polymethacrylates, proteins, and carboxylic acid functionalized starches.

In further independent embodiments of the fourth, fifth and sixth embodiments of the invention, the polymer is a non-ionizable, non-cellulosic polymer. In these embodiments, the polymer may be selected from the group consisting of vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alky- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; and polyethylene polyvinyl alcohol copolymers and polyoxyethylene-polyoxypropylene block copolymers.

In further independent embodiments of the fourth, fifth and sixth aspects of the invention, the concentration-enhancing polymer is a neutralized acidic polymer.

In further independent embodiments of the fourth, fifth and sixth aspects of the invention, the drug and said polymer are administered at about the same time. In these embodiments, the polymer and said drug may optionally be administered together. Alternativley, in these embodiments, the polymer and said drug may optionally be administered separately.

The foregoing and other objectives, features, and advantages of the invention will be more readily understood upon consideration of the following detailed description of the invention.

DETAILED DESCRIPTION OF THE INVENTION

The pharmaceutical compositions of the present invention comprise a combination of a solubility-improved form of drug and at least one concentration-enhancing polymer that enhances the concentration of the drug in a use environment relative to control compositions that are free from the concentration-enhancing polymer. Examples of solubility-improved drug forms are: (1) drug in microparticulate form; (2) drug in hanoparticulate form; (3) absorbed drug; (4) drug in a nanosuspension; (5) a supercooled melt of drug; (6) cyclodextrin/drug form; (7) softgel form; (8) gelatin form, (9) self-emulsifying form; and (10) three-phase drug form. Suitable drugs, methods to form the solubility-improved drug forms, concentration-enhancing polymers, as well as methods for preparing the compositions, and methods for coadministration are discussed in detail below.

The Drug

The present invention is useful with any drug capable of being formulated in one of the above solubility-improved drug forms. The term "drug" is conventional, denoting a compound having beneficial prophylactic and/or therapeutic properties when administered to an animal, especially humans. The drug does not need to be sparingly soluble in order to benefit from this invention, although sparingly soluble drugs represent a preferred class for use with the invention. Even a drug that nonetheless exhibits appreciable solubility in the desired environment of use can benefit from the increased solubility/bioavailability made possible by this invention if the addition of the concentration-enhancing polymer can reduce the size of the dose needed for therapeutic efficacy or increase the rate of drug absorption in cases where a rapid onset of the drug's effectiveness is desired.

The present invention finds particular utility when the drug is a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. The invention finds greater utility as the solubility of the drug decreases. Thus, compositions of the present invention are preferred for low-solubility drugs having a solubility of less than 10 mg/mL, more preferred for low-solubility drugs having a solubility of less than 1 mg/mL, and even more preferred for low-solubility drugs having a solubility of less than 0.1 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and the dose is in mg. Thus, a dose-to-aqueous-solubility ratio may be calculated by dividing the dose (in mg) by the solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein inhibitors.

Each named drug should be understood to include the neutral form of the drug, pharmaceutically acceptable salts, as well as prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin and atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4', 6'-trimethylphenoxy)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R-(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein (CETP) inhibitors include [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]4-[(3,5-Bis-trifluoromethyl-benzyl)-methoxycarbonyl-amino]-2-ethyl-6-trifluoromethyl-3,4-dihydro-2H-quinoline-1-carboxylic acid isopropyl ester.

The invention is not limited by any particular structure or group of CETP inhibitors. Rather, the invention has general applicability to CETP inhibitors as a class, the class tending to be composed of compounds having low solubility. Compounds which may be the subject of the invention may be found in a number of patents and published applications, including DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; EP 992496; and EP 987251, all of which are hereby incorporated by reference in their entireties for all purposes.

The invention is useful for CETP inhibitors that have sufficiently low aqueous solubility, low bioavailability or slow rate of absorption such that it is desirable to increase their concentration in an aqueous environment of use. Therefore, anytime one finds it desirable to raise the aqueous concentration of the CETP inhibitor in a use environment, the invention will find utility. The CETP inhibitor is "substantial water-insoluble" which means that the CETP inhibitor has a minimum aqueous solubility of less than about 0.01 mg/mL (or 10 µg/ml) at any physiologically relevant pH (e.g., pH 1-8) and at about 22° C. (Unless otherwise specified, reference to aqueous solubility herein and in the claims is determined at about 22° C.) Compositions of the present invention find greater utility as the solubility of the CETP inhibitors decreases, and thus are preferred for CETP inhibitors with solubilities less than about 2 µg/mL, and even more preferred for CETP inhibitors with solubilities less than about 0.5 µg/mL. Many CETP inhibitors have even lower solubilities (some even less than 0.1 µg/mL), and require dramatic concentration enhancement to be sufficiently bioavailable upon oral dosing for effective plasma concentrations to be reached at practical doses.

In general, it may be said that the CETP inhibitor has a dose-to-aqueous solubility ratio greater than about 100 mL, where the solubility (mg/mL) is the minimum value observed in any physiologically relevant aqueous solution (e.g., those with pH values from 1 to 8) including USP simulated gastric and intestinal buffers, and dose is in mg. Compositions of the present invention, as mentioned above, find greater utility as the solubility of the CETP inhibitor decreases and the dose increases. Thus, the compositions are preferred as the dose-to-solubility ratio increases, and thus are preferred for dose-to-solubility ratios greater than 1000 mL, and more preferred for dose-to-solubility ratios greater than about 5000 ml. The dose-to-solubility ratio may be determined by dividing the dose (in mg) by the aqueous solubility (in mg/ml).

Oral delivery of many CETP inhibitors is particularly difficult because their aqueous solubility is usually extremely low, typically being less than 2 μg/ml, often being less than 0.1 μg/ml. Such low solubilities are a direct consequence of the particular structural characteristics of species that bind to CETP and thus act as CETP inhibitors. This low solubility is primarily due to the hydrophobic nature of CETP inhibitors. Clog P, defined as the base 10 logarithm of the ratio of the drug solubility in octanol to the drug solubility in water, is a widely accepted measure of hydrophobicity. In general, Clog P values for CETP inhibitors are greater than 4 and are often greater than 5 to 7. Thus, the hydrophobic and insoluble nature of CETP inhibitors as a class pose a particular challenge for oral delivery. Achieving therapeutic drug levels in the blood by oral dosing of practical quantities of drug generally requires a large enhancement in drug concentrations in the gastrointestinal fluid and a resulting large enhancement in bioavailability. Such enhancements in drug concentration in gastrointestsinal fluid typically need to be at least about 10-fold and often at least about 50-fold or even at least about 200-fold to achieve desired blood levels. Surprisingly, the formulations of the present invention have proven to have the required large enhancements in drug concentration and bioavailability.

In contrast to conventional wisdom, the relative degree of enhancement in aqueous concentration and bioavailability generally improves for CETP inhibitors as solubility decreases and hydrophobocity increases. In fact, the inventors have recognized a subclass of these CETP inhibitors that are essentially aqueous insoluble, highly hydrophobic, and are characterized by a set of physical properties. This subclass exhibits dramatic enhancements in aqueous concentration and bioavailability when formulated using the compositions of the present invention.

The first property of this subclass of essentially insoluble, hydrophobic CETP inhibitors is extremely low aqueous solubility. By extremely low aqueous solubility is meant that the minimum aqueous solubility at physiologically relevant pH (pH of 1 to 8) is less than about 10 μg/ml and preferably less than about 1 μg/ml.

A second property is a very high does-to-solubility ratio. Extremely low solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic CETP inhibitors is a very high dose (in mg) to solubility (in mg/ml) ratio (ml). By "very high dose-to-solubility ratio" is meant that the dose-to-solubility ratio has a value of at least 1000 ml, and preferably at least 5,000 ml, and more preferably at least 10,000 ml.

A third property of this subclass of essentially insoluble, hydrophobic CETP inhibitors is that they are extremely hydrophobic. By extremely hydrophobic is meant that the Clog P value of the drug, has a value of at least 4.0, preferably a value of at least 5.0, and more preferably a value of at least 5.5.

A fourth property of this subclass of essentially insoluble CETP inhibitors is that they have a low melting point. Generally, drugs of this subclass will have a melting point of about 150° C. or less, and preferably about 140° C. or less.

Primarily, as a consequence of some or all of these four properties, CETP inhibitors of this subclass typically have very low absolute bioavailabilities. Specifically, the absolute bioavailibility of drugs in this subclass when dosed orally in their undispersed state is less than about 10% and more often less than about 5%.

Turning now to the chemical structures of specific CETP inhibitors, one class of CETP inhibitors that finds utility with the present invention consists of oxy substituted 4-carboxyamino-2-methyl-1,2,3,4-tetrahydroquinolines having the Formula I

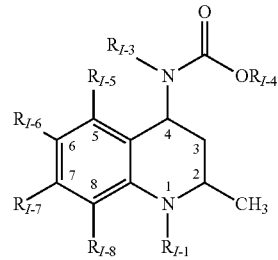

Formula I and pharmaceutically acceptable salts, enantiomers, or stereoisomers of said compounds;

wherein $R_{I-1}$ is hydrogen, $Y_I$, $W_I$—$X_I$, $W_I$—$Y_I$;

wherein $W_I$ is a carbonyl, thiocarbonyl, sulfinyl or sulfonyl;

$X_I$ is —O—$Y_I$, —S—$Y_I$, —N(H)—$Y_I$ or —N—$(Y_I)_2$;

wherein $Y_I$ for each occurrence is independently $Z_I$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_I$;

wherein $Z_I$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_I$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino, said $(C_1-C_6)$ alkyl substituent is also optionally substituted with from one to nine fluorines;

$R_{I-3}$ is hydrogen or $Q_I$;

wherein $Q_I$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_I$;

wherein $V_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_I$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carbamoyl, mono-N- or di-N,N-$(C_1-C_6)$ alkylcarbamoyl, carboxyl, $(C_1-C_6)$alkyloxycarbonyl, mono-N- or di-N,N-$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino, said $(C_1-C_6)$alkyl or $(C_2-C_6)$alkenyl substituents are also optionally substituted with from one to nine fluorines;

$R_{I-4}$ is $Q_{I-1}$ or $V_{I-1}$ wherein $Q_{I-1}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{I-1}$;

wherein $V_{I-1}$, is a partially saturated, fully saturated or fully unsaturated three to six membered ring optionally having one to two heteroatoms selected independently from oxygen, sulfur and nitrogen;

wherein said $V_{I-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N- or di-N,N-$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{I-3}$ must contain $V_I$ or $R_{I-4}$ must contain $V_{I-1}$; and $R_{I-5}$, $R_{I-6}$, $R_{I-7}$ and $R_{I-8}$ are each independently hydrogen, hydroxy or oxy wherein said oxy is substituted with $T_I$ or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_I$;

wherein $T_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_I$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$ alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$ alkyl substituent is also optionally substituted with from one to nine fluorines.

Compounds of Formula I and their methods of manufacture are disclosed in commonly assigned U.S. Pat. No. 6,140,342, U.S. Pat. No. 6,362,198, and European Patent publication 987251, all of which are incorporated herein by reference in their entireties for all purposes.

In a preferred embodiment, the CETP inhibitor is selected from one of the following compounds of Formula I:

[2R,4S]4-[(3,5-dichloro-benzyl)-methoxycarbonyl-amino]-6,7-dimethoxy-2-methyl-3,4-dihydro-2H-quinoline-1-carboxylic acid ethyl ester;

[2R,4S]4-[(3,5-dinitro-benzyl)-methoxycarbonyl-amino]-6,7-dimethoxy-2-methyl-3,4-dihydro-2H-quinoline-1-carboxylic acid ethyl ester;

[2R,4S]4-[(2,6-dichloro-pyridin-4-ylmethyl)-methoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6-methoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-7-methoxy-2-methyl-3,4-dihydro-2H-quinoline-1-carboxylic acid ethyl ester,

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid isopropyl ester;

[2R,4S]4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid 2,2,2-trifluoroethylester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid propyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid tert-butyl ester;

[2R,4S]4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester,

[2R,4S](3,5-bis-trifluoromethyl-benzyl)-(1-butyryl-6,7-dimethoxy-2-methyl-1,2,3,4-tetrahydro-quinolin-4-yl)-carbamic acid methyl ester;

[2R,4S](3,5-bis-trifluoromethyl-benzyl)-(1-butyl-6,7-dimethoxy-2-methyl-1,2,3,4-tetrahydro-quinolin-4-yl)-carbamic acid methyl ester; and

[2R,4S](3,5-bis-trifluoromethyl-benzyl)-[1-(2-ethyl-butyl)-6,7-dimethoxy-2-methyl-1,2,3,4-tetrahydro-quinolin-4-yl]-carbamic acid methyl ester, hydrochloride.

Another class of CETP inhibitors that finds utility with the present invention consists of 4-carboxyamino-2-methyl-1,2,3,4,-tetrahydroquinolines, having the Formula II

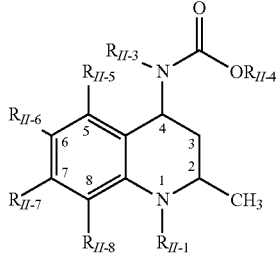

Formula II and pharmaceutically acceptable salts, enantiomers, or stereoisomers of said compounds;

wherein $R_{II-1}$ is hydrogen, $Y_{II}$, $W_{II}-X_{II}$, $W_{II}-Y_{II}$;

wherein $W_{II}$ is a carbonyl, thiocarbonyl, sulfinyl or sulfonyl;

$X_{II}$ is $-O-Y_{II}$, $-S-Y_{II}$, $-N(H)-Y_{II}$, or $-N-(Y_{II})_2$;

wherein $Y_{II}$ for each occurrence is independently $Z_{II}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{II}$;

$Z_{II}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{II}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$alkyl is also optionally substituted with from one to nine fluorines;

$R_{II-3}$ is hydrogen or $Q_{II-1}$;

wherein $Q_{II-1}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II}$;

wherein $V_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{II}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N- or di-N,N-$(C_1-C_6)$ alkylcarboxamoyl, carboxy, $(C_1-C_6)$alkyloxycarbonyl, mono-N- or di-N,N-$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino or said $(C_1-C_6)$alkyl or $(C_2-C_6)$alkenyl substituents are optionally substituted with from one to nine fluorines;

$R_{II-4}$ is $Q_{II-1}$ or $V_{II-1}$;

wherein $Q_{II-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II-1}$;

wherein $V_{II-1}$ is a partially saturated, fully saturated or fully unsaturated three to six membered ring optionally having one to two heteroatoms selected independently from oxygen, sulfur and nitrogen;

wherein said $V_{II-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N- or di-N,N-$(C_1-C_6)$alkylamino wherein said $(C_1-C_6)$alkyl substituent is optionally mono-substituted with oxo, said $(C_1-C_6)$alkyl substituent is optionally substituted with from one to nine fluorines;

wherein either $R_{II-3}$ must contain $V_{II}$ or $R_{II-4}$ must contain $V_{II-1}$; and $R_{II-5}$, $R_{II-6}$, $R_{II-7}$ and $R_{II-8}$ are each independently hydrogen, a bond, nitro or halo wherein said bond is substituted with $T_{II}$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{II}$;

wherein $T_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{II}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$ alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$ alkyl substituent is also optionally substituted with from one to nine fluorines;

provided that at least one of substituents $R_{II-5}$, $R_{II-6}$, $R_{II-7}$ and $R_{II-8}$ is not hydrogen and is not linked to the quinoline moiety through oxy.

Compounds of Formula II and their methods of manufacture are disclosed in commonly assigned U.S. Pat. No. 6,147,090, U.S. patent application Ser. No. 09/671,400 filed Sep. 27, 2000, and PCT Publication No. WO00/17166, all of which are incorporated herein by reference in their entireties for all purposes.

In a preferred embodiment, the CETP inhibitor is selected from one of the following compounds of Formula II:

[2R,4S]4-[(3,5-Bis-trifluoromethyl-benzyl)-methoxycarbonyl-amino]-2-methyl-7-trifluoromethyl-3,4-dihydro-2H-quinoline-1-carboxylic acid ethyl ester;

[2R,4S]4-[(3,5-Bis-trifluoromethyl-benzyl)-methoxycarbonyl-amino]-7-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2,6,7-trimethyl-3,4-dihydro-2H-quinoline-1-carboxylic acid ethyl ester;

[2R,4S]4-[(3,5-Bis-trifluoromethyl-benzyl)-methoxycarbonyl-amino]-6,7-diethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-ethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2-methyl-6-trifluoromethyl-3,4-dihydro-2H-quinoline-1-carboxylic acid ethyl ester; and

[2R,4S]4-[(3,5-bis-trifluoromethyl-benzyl)-methoxycarbonyl-amino]-2-methyl-6-trifluoromethyl-3,4-dihydro-2H-quinoline-1-carboxylic acid isopropyl ester.

Another class of CETP inhibitors that finds utility with the present invention consists of annulated 4-carboxyamino-2-methyl-1,2,3,4,-tetrahydroquinolines, having the Formula III Formula III

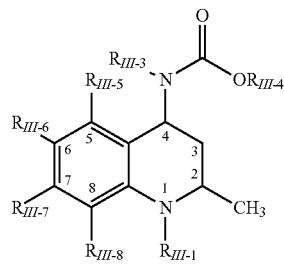

and pharmaceutically acceptable salts, enantiomers, or stereoisomers of said compounds;

wherein $R_{III-1}$ is hydrogen, $Y_{III}$, $W_{III}$—$X_{III}$, $W_{III}$—$Y_{III}$;

wherein $W_{III}$ is a carbonyl, thiocarbonyl, sulfinyl or sulfonyl;

$X_{III}$ is —O—$Y_{III}$, —S—$Y_{III}$, —N(H)—$Y_{III}$ or —N—$(Y_{III})_2$;

$Y_{III}$ for each occurrence is independently $Z_{III}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{III}$;

wherein $Z_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{III}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$alkyl optionally substituted with from one to nine fluorines;

$R_{III-3}$ is hydrogen or $Q_{III}$;

wherein $Q_{III}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III}$;

wherein $V_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{III}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N- or di-N,N-$(C_1-C_6)$ alkylcarboxamoyl, carboxy, $(C_1-C_6)$alkyloxycarbonyl, mono-N- or di-N,N-$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-$ $C_6$)alkylamino or said ($C_1$-$C_6$)alkyl or ($C_2$-$C_6$)alkenyl are optionally substituted with from one to nine fluorines;

$R_{III-4}$ is $Q_{III-1}$ or $V_{III-1}$;

wherein $Q_{III-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III-1}$;

wherein $V_{III-1}$ is a partially saturated, fully saturated or fully unsaturated three to six membered ring optionally having one to two heteroatoms selected independently from oxygen, sulfur and nitrogen;

wherein said $V_{III-1}$ substituent is optionally mono-, di-, tri-, or tetra-substituted independently with halo, ($C_1$-$C_6$)alkyl, ($C_1$-$C_6$)alkoxy, amino, nitro, cyano, ($C_1$-$C_6$)alkyloxycarbonyl, mono-N- or di-N,N-($C_1$-$C_6$)alkylamino wherein said ($C_1$-$C_6$)alkyl substituent is optionally mono-substituted with oxo, said ($C_1$-$C_6$)alkyl substituent optionally having from one to nine fluorines;

wherein either $R_{III-3}$ must contain $V_{III}$ or $R_{III-4}$ must contain $V_{III-1}$; and $R_{III-5}$ and $R_{III-6}$, or $R_{III-6}$ and $R_{III-7}$, and/or $R_{III-7}$ and $R_{III-8}$ are taken together and form at least one four to eight membered ring that is partially saturated or fully unsaturated optionally having one to three heteroatoms independently selected from nitrogen, sulfur and oxygen;

wherein said ring or rings formed by $R_{III-5}$ and $R_{III-6}$, or $R_{III-6}$ and $R_{III-7}$, and/or $R_{III-7}$ and $R_{III-8}$ are optionally mono-, di- or tri-substituted independently with halo, ($C_1$-$C_6$)alkyl, ($C_1$-$C_4$)alkylsulfonyl, ($C_2$-$C_6$)alkenyl, hydroxy, ($C_1$-$C_6$) alkoxy, ($C_1$-$C_4$)alkylthio, amino, nitro, cyano, oxo, carboxy, ($C_1$-$C_6$)alkyloxycarbonyl, mono-N- or di-N,N-($C_1$-$C_6$)alkylamino wherein said ($C_1$-$C_6$)alkyl substituent is optionally mono-, di- or tri-substituted independently with hydroxy, ($C_1$-$C_6$)alkoxy, ($C_1$-$C_4$)alkylthio, amino, nitro, cyano, oxo, carboxy, ($C_1$-$C_6$)alkyloxycarbonyl, mono-N- or di-N,N-($C_1$-$C_6$)alkylamino, said ($C_1$-$C_6$)alkyl substituent optionally having from one to nine fluorines;

provided that the $R_{III-5}$, $R_{III-6}$, $R_{III-7}$ and/or $R_{III-8}$, as the case may be, that do not form at least one ring are each independently hydrogen, halo, ($C_1$-$C_6$)alkoxy or ($C_1$-$C_6$) alkyl, said ($C_1$-$C_6$)alkyl optionally having from one to nine fluorines.

Compounds of Formula III and their methods of manufacture are disclosed in commonly assigned U.S. Pat. No. 6,147,089, U.S. Pat. No. 6,310,075, and European Patent Application No. 99307240.4 filed Sep. 14, 1999, all of which are incorporated herein by reference in their entireties for all purposes.

In a preferred embodiment, the CETP inhibitor is selected from one of the following compounds of Formula III:

[2R,4S]4-[(3,5-bis-trifluoromethyl-benzyl)-methoxycarbonyl-amino]-2-methyl-2,3,4,6,7,8-hexahydro-cyclopenta[g]quinoline-1-carboxylic acid ethyl ester;

[6R,8S]8-[(3,5-bis-trifluoromethyl-benzyl)-methoxycarbonyl-amino]-6-methyl-3,6,7,8-tetrahydro-1H-2-thia-5-aza-cyclopenta[b]naphthalene-5-carboxylic acid ethyl ester;

[6R,8S]8-[(3,5-bis-trifluoromethyl-benzyl)-methoxycarbonyl-amino]-6-methyl-3,6,7,8-tetrahydro-2H-furo[2,3-g]quinoline-5-carboxylic acid ethyl ester;

[2R,4S]4-[(3,5-bis-trifluoromethyl-benzyl)-methoxycarbonyl-amino]-2-methyl-3,4,6,8-tetrahydro-2H-furo[3,4-g]quinoline-1-carboxylic acid ethyl ester;

[2R,4S]4-[(3,5-bis-trifluoromethyl-benzyl)-methoxycarbonyl-amino]-2-methyl-3,4,6,7,8,9-hexahydro-2H-benzo[g]quinoline-1-carboxylic acid propyl ester;

[7R,9S]9-[(3,5-bis-trifluoromethyl-benzyl)-methoxycarbonyl-amino]-7-methyl-1,2,3,7,8,9-hexahydro-6-aza-cyclopenta[a]naphthalene-6-carboxylic acid ethyl ester; and

[6S,8R]6-[(3,5-bis-trifluoromethyl-benzyl)-methoxycarbonyl-amino]-8-methyl-1,2,3,6,7,8-hexahydro-9-aza-cyclopenta[a]naphthalene-9-carboxylic acid ethyl ester.

Another class of CETP inhibitors that finds utility with the present invention consists of 4-carboxyamino-2-substituted-1,2,3,4,-tetrahydroquinolines, having the Formula IV Formula IV

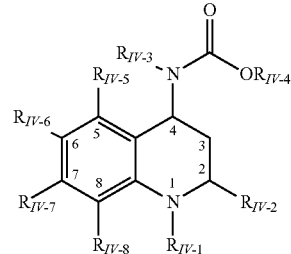

and pharmaceutically acceptable salts, enantiomers, or stereoisomers of said compounds;

wherein $R_{IV-1}$ is hydrogen, $Y_{IV}$, $W_{IV}$—$X_{IV}$ or $W_{IV}$—$Y_{IV}$;

wherein $W_{IV}$ is a carbonyl, thiocarbonyl, sulfinyl or sulfonyl;

$X_{IV}$ is —O—$Y_{IV}$, —S—$Y_{IV}$, —N(H)—$Y_{IV}$ or —N—$(Y_{IV})_2$;

wherein $Y_{IV}$ for each occurrence is independently $Z_{IV}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{IV}$;

wherein $Z_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{IV}$ substituent is optionally mono-, di- or tri-substituted independently with halo, ($C_2$-$C_6$)alkenyl, ($C_1$-$C_6$) alkyl, hydroxy, ($C_1$-$C_6$)alkoxy, ($C_1$-$C_4$)alkylthio, amino, nitro, cyano, oxo, carboxy, ($C_1$-$C_6$)alkyloxycarbonyl, mono-N- or di-N,N-($C_1$-$C_6$)alkylamino wherein said ($C_1$-$C_6$)alkyl substituent is optionally mono-, di- or tri-substituted independently with halo, hydroxy, ($C_1$-$C_6$)alkoxy, ($C_1$-$C_4$)alkylthio, amino, nitro, cyano, oxo, carboxy, ($C_1$-$C_6$)alkyloxycarbonyl, mono-N- or di-N,N-($C_1$-$C_6$)alkylamino, said ($C_1$-$C_6$)alkyl substituent is also optionally substituted with from one to nine fluorines;

$R_{IV-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{IV-2}$ is a partially saturated, fully saturated or fully unsaturated three to seven membered ring optionally having one to two heteroatoms selected independently from oxygen, sulfur and nitrogen, wherein said $R_{IV-2}$ ring is optionally attached through $(C_1-C_4)$alkyl;

wherein said $R_{IV-2}$ ring is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, oxo or $(C_1-C_6)$alkyloxycarbonyl;

with the proviso that $R_{IV-2}$ is not methyl;

$R_{IV-3}$ is hydrogen or $Q_{IV}$;

wherein $Q_{IV}$ is a fully saturated, partially unsaturated or fully unsaturated one to six membered straight or branched carbon chain wherein the carbons other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV}$;

wherein $V_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{IV}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N- or di-N,N-$(C_1-C_6)$ alkylcarboxamoyl, carboxy, $(C_1-C_6)$alkyloxycarbonyl, mono-N- or di-N,N-$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$alkyl or $(C_2-C_6)$alkenyl substituents are also optionally substituted with from one to nine fluorines;

$R_{IV-4}$ is $Q_{IV-1}$ or $V_{IV-1}$;

wherein $Q_{IV-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV-1}$;

wherein $V_{IV-1}$ is a partially saturated, fully saturated or fully unsaturated three to six membered ring optionally having one to two heteroatoms selected independently from oxygen, sulfur and nitrogen;

wherein said $V_{IV-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N- or di-N,N-$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{IV-3}$ must contain $V_{IV}$ or $R_{IV-4}$ must contain $V_{IV-1}$;

$R_{IV-5}$, $R_{IV-6}$, $R_{IV-7}$ and $R_{IV-8}$ are each independently hydrogen, a bond, nitro or halo wherein said bond is substituted with $T_{IV}$ or a partially saturated, fully saturated or fully unsaturated $(C_1-C_{12})$ straight or branched carbon chain wherein carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{IV}$;

wherein $T_{IV}$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{IV}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$ alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$ alkyl substituent is also optionally substituted with from one to nine fluorines; and wherein $R_{IV-5}$ and $R_{IV-6}$, or $R_{IV-6}$ and $R_{IV-7}$, and/or $R_{IV-7}$ and $R_{IV-8}$ may also be taken together and can form at least one four to eight membered ring that is partially saturated or fully unsaturated optionally having one to three heteroatoms independently selected from nitrogen, sulfur and oxygen;

wherein said ring or rings formed by $R_{IV-5}$ and $R_{IV-6}$, or $R_{IV-6}$ and $R_{IV-7}$, and/or $R_{IV-7}$ and $R_{IV-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$alkyl substituent is also optionally substituted with from one to nine fluorines;

with the proviso that when $R_{IV-2}$ is carboxyl or $(C_1-C_4)$alkylcarboxyl, then $R_{IV-1}$ is not hydrogen.

Compounds of Formula IV and their methods of manufacture are disclosed in commonly assigned U.S. Pat. No. 6,197,786, U.S. application Ser. No. 09/685,3000 filed Oct. 10, 2000, and PCT Publication No. WO 00/17164, all of which are incorporated herein by reference in their entireties for all purposes.

In a preferred embodiment, the CETP inhibitor is selected from one of the following compounds of Formula IV:
[2S,4S]4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;
[2S,4S]4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;
[2S,4S]2-cyclopropyl-4-[(3,5-dichloro-benzyl)-methoxycarbonyl-amino]-6-trifluoromethyl-3,4-dihydro-2H-quinoline-1-carboxylic acid isopropyl ester;
[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;
[2R,4R]4-[(3,5-bis-trifluoromethyl-benzyl)-methoxycarbonyl-amino]-2-cyclopropyl-6-trifluoromethyl-3,4-dihydro-2H-quinaline-1-carboxylic acid isopropyl ester;
[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;
[2S,4S]4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;
[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;
[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;
[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;
[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;
[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;
[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and
[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester.

Another class of CETP inhibitors that finds utility with the present invention consists of 4-amino substituted-2-substituted-1,2,3,4,-tetrahydroquinolines, having the Formula V

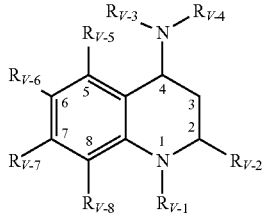

Formula V and pharmaceutically acceptable salts, enantiomers, or stereoisomers of said compounds;
wherein $R_{V-1}$ is $Y_V$, $W_V$—$X_V$ or $W_V$—$Y_V$;
wherein $W_V$ is a carbonyl, thiocarbonyl, sulfinyl or sulfonyl;
$X_V$ is —O—$Y_V$, —S—$Y_V$, —N(H)—$Y_V$ or —N—$(Y_V)_2$;
wherein $Y_V$ for each occurrence is independently $Z_V$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_V$;
wherein $Z_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;
wherein said $Z_V$ substituent is optionally mono-, di- or tri-substituted independently with halo, $(C_2$-$C_6)$alkenyl, $(C_1$-$C_6)$ alkyl, hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N- or di-N,N-$(C_1$-$C_6)$alkylamino wherein said $(C_1$-$C_6)$alkyl substituent is optionally mono-, di- or tri-substituted independently with halo, hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N- or di-N,N-$(C_1$-$C_6)$alkylamino, said $(C_1$-$C_6)$alkyl substituent is also optionally substituted with from one to nine fluorines;
$R_{V-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{V-2}$ is a partially saturated, fully saturated or fully unsaturated three to seven membered ring optionally having one to two heteroatoms selected independently from oxygen, sulfur and nitrogen, wherein said $R_{V-2}$ ring is optionally attached through $(C_1$-$C_4)$alkyl;
wherein said $R_{V-2}$ ring is optionally mono-, di- or tri-substituted independently with halo, $(C_2$-$C_6)$alkenyl, $(C_1$-$C_6)$ alkyl, hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N- or di-N,N-$(C_1$-$C_6)$alkylamino wherein said $(C_1$-$C_6)$alkyl substituent is optionally mono-, di- or tri-substituted independently with halo, hydroxy, $(C_1$-$C_6)$alkoxy, $(C_1$-$C_4)$alkylthio, oxo or $(C_1$-$C_6)$alkyloxycarbonyl;
$R_{V-3}$ is hydrogen or $Q_V$;
wherein $Q_V$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_V$;

wherein $V_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_V$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N- or di-N,N-$(C_1-C_6)$ alkylcarboxamoyl, carboxy, $(C_1-C_6)$alkyloxycarbonyl, mono-N- or di-N,N-$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$alkyl or $(C_2-C_6)$alkenyl substituents are also optionally substituted with from one to nine fluorines;

$R_{V-4}$ is cyano, formyl, $W_{V-1}Q_{V-1}$, $W_{V-1}V_{V-1}$, $(C_1-C_4)$alkyleneV$_{V-1}$ or $V_{V-2}$;

wherein $W_{V-1}$ is carbonyl, thiocarbonyl, SO or $SO_2$, wherein $Q_{V-1}$ a fully saturated, partially unsaturated or fully unsaturated one to six membered straight or branched carbon chain wherein the carbons may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{V-1}$;

wherein $V_{V-1}$ is a partially saturated, fully saturated or fully unsaturated three to six membered ring optionally having one to two heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{V-1}$ substituent is optionally mono-, di-, tri-, or tetra-substituted independently with halo, $(C_1-C_6)$alkyl, $(C_1-C_6)$alkoxy, hydroxy, oxo, amino, nitro, cyano, $(C_1-C_6)$alkyloxycarbonyl, mono-N- or di-N,N-$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein $V_{V-2}$ is a partially saturated, fully saturated or fully unsaturated five to seven membered ring containing one to four heteroatoms selected independently from oxygen, sulfur and nitrogen;

wherein said $V_{V-2}$ substituent is optionally mono-, di- or tri-substituted independently with halo, $(C_1-C_2)$alkyl, $(C_1-C_2)$alkoxy, hydroxy, or oxo wherein said $(C_1-C_2)$alkyl optionally has from one to five fluorines; and wherein $R_{V-4}$ does not include oxycarbonyl linked directly to the $C^4$ nitrogen;

wherein either $R_{V-3}$ must contain $V_V$ or $R_{V-4}$ must contain $V_{V-1}$;

$R_{V-5}$, $R_{V-6}$, $R_{V-7}$ and $R_{V-8}$ are independently hydrogen, a bond, nitro or halo wherein said bond is substituted with $T_V$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen, wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_V$;

wherein $T_V$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_V$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$ alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$ alkyl substituent also optionally has from one to nine fluorines;

wherein $R_{V-5}$ and $R_{V-6}$, or $R_{V-6}$ and $R_{V-7}$, and/or $R_{V-7}$ and $R_{V-8}$ may also be taken together and can form at least one ring that is a partially saturated or fully unsaturated four to eight membered ring optionally having one to three heteroatoms independently selected from nitrogen, sulfur and oxygen;

wherein said rings formed by $R_{V-5}$ and $R_{V-6}$, or $R_{V-6}$ and $R_{V-7}$, and/or $R_{V-7}$ and $R_{V-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$alkyl substituent also optionally has from one to nine fluorines.

Compounds of Formula V and their methods of manufacture are disclosed in commonly assigned U.S. Pat. No. 6,140,343, U.S. patent application Ser. No. 09/671,221 filed Sep. 27, 2000, and PCT Publication No. WO 00/17165, all of which are incorporated herein by reference in their entireties for all purposes.

In a preferred embodiment, the CETP inhibitor is selected from one of the following compounds of Formula V:

[2S,4S]4-[(3,5-bis-trifluoromethyl-benzyl)-formyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-formyl-amino]-2-cyclopropyl-6-trifluoromethyl-3,4-dihydro-2H-quinoline-1-carboxylic acid propyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid tert-butyl ester;

[2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester;

[2R,4S]4-[acetyl-(3,5-bis-trifluoromethyl-benzyl)-amino]-2-methyl-6-trifluoromethyl-3,4-dihydro-2H-quinoline-1-carboxylic acid ethyl ester;
[2S,4S]4-[1-(3,5-bis-trifluoromethyl-benzyl)-ureido]-2-cyclopropyl-6-trifluoromethyl-3,4-dihydro-2H-quinoline-1-carboxylic acid isopropyl ester;
[2R,4S]4-[acetyl-(3,5-bis-trifluoromethyl-benzyl)-amino]-2-ethyl-6-trifluoromethyl-3,4-dihydro-2H-quinoline-1-carboxylic acid ethyl ester;
[2S,4S]4-[acetyl-(3,5-bis-trifluoromethyl-benzyl)-amino]-2-methoxymethyl-6-trifluoromethyl-3,4-dihydro-2H-quinoline-1-carboxylic acid isopropyl ester;
[2S,4S]4-[acetyl-(3,5-bis-trifluoromethyl-benzyl)-amino]-2-cyclopropyl-6-trifluoromethyl-3,4-dihydro-2H-quinoline-1-carboxylic acid propyl ester;
[2S,4S]4-[acetyl-(3,5-bis-trifluoromethyl-benzyl)-amino]-2-cyclopropyl-6-trifluoromethyl-3,4-dihydro-2H-quinoline-1-carboxylic acid ethyl ester;
[2R,4S]4-[(3,5-bis-trifluoromethyl-benzyl)-formyl-amino]-2-ethyl-6-trifluoromethyl-3,4-dihydro-2H-quinoline-1-carboxylic acid isopropyl ester;
[2R,4S]4-[(3,5-bis-trifluoromethyl-benzyl)-formyl-amino]-2-methyl-6-trifluoromethyl-3,4-dihydro-2H-quinoline-1-carboxylic acid ethyl ester;
[2S,4S]4-[acetyl-(3,5-bis-trifluoromethyl-benzyl)-amino]-2-cyclopropyl-6-trifluoromethyl-3,4-dihydro-2H-quinoline-1-carboxylic acid isopropyl ester;
[2R,4S]4-[(3,5-bis-trifluoromethyl-benzyl)-formyl-amino]-2-ethyl-6-trifluoromethyl-3,4-dihydro-2H-quinoline-1-carboxylic acid ethyl ester;
[2S,4S]4-[(3,5-bis-trifluoromethyl-benzyl)-formyl-amino]-2-cyclopropyl-6-trifluoromethyl-3,4-dihydro-2H-quinoline-1-carboxylic acid ethyl ester;
[2R,4S]4-[(3,5-bis-trifluoromethyl-benzyl)-formyl-amino]-2-methyl-6-trifluoromethyl-3,4-dihydro-2H-quinoline-1-carboxylic acid isopropyl ester; and
[2R,4S]4-[acetyl-(3,5-bis-trifluoromethyl-benzyl)-amino]-2-methyl-6-trifluoromethyl-3,4-dihydro-2H-quinoline-1-carboxylic acid isopropyl ester.

Another class of CETP inhibitors that finds utility with the present invention consists of cycloalkano-pyridines having the Formula VI

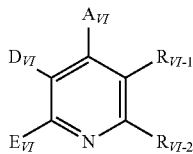

Formula VI and pharmaceutically acceptable salts, enantiomers, or stereoisomers of said compounds;
in which
$A_{VI}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$BNR_{VI-3}R_{VI-4}$, wherein
$R_{VI-3}$ and $R_{VI-4}$ are identical or different and denote a hydrogen, phenyl or a straight-chain or branched alkyl containing up to 6 carbon atoms,
$D_{VI}$ denotes an aryl containing 6 to 10 carbon atoms, which is optionally substituted with a phenyl, nitro, halogen, trifluoromethyl or trifluoromethoxy, or a radical according to the formula $R_{VI-5}$-$L_{VI}$-,

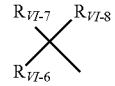

or $R_{VI-9}$-$T_{VI}$-$V_{VI}$—$X_{VI}$, wherein
$R_{VI-5}$, $R_{VI-6}$ and $R_{VI-9}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteoatoms from the series of S, N and/or O, and/or in the form of a group according to the formula $BOR_{VI-10}$, —$SR_{VI-11}$, —$SO_2R_{VI-12}$ or $BNR_{VI-13}R_{VI-14}$, wherein
$R_{VI-10}$, $R_{VI-11}$ and $R_{VI-12}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms,
$R_{VI-13}$ and $R_{VI-14}$ are identical or different and have the meaning of $R_{VI-3}$ and $R_{VI-4}$ given above, or
$R_{VI-5}$ and/or $R_{VI-6}$ denote a radical according to the formula

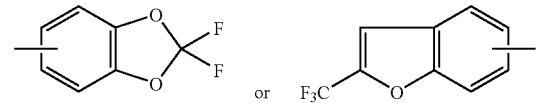

$R_{VI-7}$ denotes a hydrogen or halogen, and
$R_{VI-8}$ denotes a hydrogen, halogen, azido, trifluoromethyl, hydroxyl, trifluoromethoxy, a straight-chain or branched alkoxy or alkyl containing up to 6 carbon atoms each, or a radical according to the formula

—$NR_{VI-15}R_{VI-16}$, wherein
$R_{VI-15}$ and $R_{VI-16}$ are identical or different and have the meaning of $R_{VI-3}$ and $R_{VI-4}$ given above, or
$R_{VI-7}$ and $R_{VI-8}$ together form a radical according to the formula =O or =$NR_{VI-17}$, wherein
$R_{VI-17}$ denotes a hydrogen or a straight-chain or branched alkyl, alkoxy or acyl containing up to 6 carbon atoms each,
$L_{VI}$ denotes a straight-chain or branched alkylene or alkenylene chain containing up to 8 carbon atoms each, which are optionally substituted with up to two hydroxyl groups,
$T_{VI}$ and $X_{VI}$ are identical or different and denote a straight-chain or branched alkylene chain containing up to 8 carbon atoms, or
$T_{VI}$ or $X_{VI}$ denotes a bond, $V_{VI}$ denotes an oxygen or sulfur atom or an $BNR_{VI-18}$ group, wherein $R_{VI-18}$ denotes a hydrogen or a straight-chain or branched alkyl containing up to 6 carbon atoms or a phenyl, $E_{VI}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl, $R_{VI-1}$ and $R_{VI-2}$ together form a straight-chain or branched alkylene chain containing up to 7 carbon atoms, which must be substituted with a carbonyl group and/or a radical according to the formula

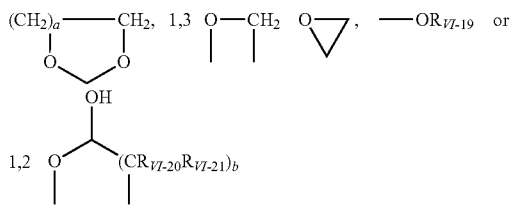

wherein a and b are identical or different and denote a number equaling 1, 2 or 3, $R_{VI-19}$ denotes a hydrogen atom, a cycloalkyl containing 3 to 7 carbon atoms, a straight-chain or branched silylalkyl containing up to 8 carbon atoms, or a straight-chain or branched alkyl containing up to 8 carbon atoms, which is optionally substituted with a hydroxyl, a straight-chain or a branched alkoxy containing up to 6 carbon atoms or a phenyl, which may in turn be substituted with a halogen, nitro, trifluoromethyl, trifluoromethoxy or phenyl or tetrazole-substituted phenyl, and an alkyl that is optionally substituted with a group according to the formula $BOR_{VI-22}$, wherein $R_{VI-22}$ denotes a straight-chain or branched acyl containing up to 4 carbon atoms or benzyl, or $R_{VI-19}$ denotes a straight-chain or branched acyl containing up to 20 carbon atoms or benzoyl, which is optionally substituted with a halogen, trifluoromethyl, nitro or trifluoromethoxy, or a straight-chain or branched fluoroacyl containing up to 8 carbon atoms, $R_{VI-20}$ and $R_{VI-21}$ are identical or different and denote a hydrogen, phenyl or a straight-chain or branched alkyl containing up to 6 carbon atoms, or $R_{VI-20}$ and $R_{VI-21}$ together form a 3- to 6-membered carbobocyclic ring, and a the carbocyclic rings formed are optionally substituted, optionally also geminally, with up to six identical or different substituents in the form of trifluoromethyl, hydroxyl, nitrile, halogen, carboxyl, nitro, azido, cyano, cycloalkyl or cycloalkyloxy containing 3 to 7 carbon atoms each, a straight-chain or branched alkoxycarbonyl, alkoxy or alkylthio containing up to 6 carbon atoms each, or a straight-chain or branched alkyl containing up to 6 carbon atoms, which is in turn substituted with up to two identical or different substituents in the form of a hydroxyl, benzyloxy, trifluoromethyl, benzoyl, a straight-chain or branched alkoxy, oxyacyl or carboxyl containing up to 4 carbon atoms each and/or a phenyl, which may in turn be substituted with a halogen, trifluoromethyl or trifluoromethoxy, and/or the carbobocyclic rings formed are optionally substituted, also geminally, with up to five identical or different substituents in the form of a phenyl, benzoyl, thiophenyl or sulfonylbenzyl, which in turn are optionally substituted with a halogen, trifluoromethyl, trifluoromethoxy or nitro, and/or optionally in the form of a radical according to the formula

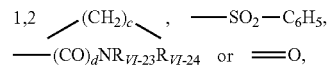

wherein c is a number equaling 1, 2, 3 or 4, d is a number equaling 0 or 1, $R_{VI-23}$ and $R_{VI-24}$ are identical or different and denote a hydrogen, cycloalkyl containing 3 to 6 carbon atoms, a straight-chain or branched alkyl containing up to 6 carbon atoms, benzyl or phenyl, which is optionally substituted with up to two identical or different substituents in the form of halogen, trifluoromethyl, cyano, phenyl or nitro, and/or the carbocyclic rings formed are optionally substituted with a spiro-linked radical according to the formula

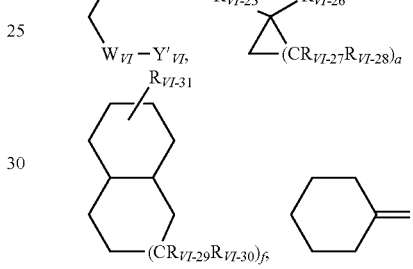

wherein $W_{VI}$ denotes either an oxygen atom or a sulfur atom, $Y_{VI}$ and $Y={VI}$ together form a 2- to 6-membered straight-chain or branched alkylene chain, e is a number equaling 1, 2, 3, 4, 5, 6 or 7, f is a number equaling 1 or 2, $R_{VI-25}$, $R_{VI-26}$, $R_{VI-27}$, $R_{VI-28}$, $R_{VI-29}$, $R_{VI-30}$ and $R_{VI-31}$ are identical or different and denote a hydrogen, trifluoromethyl, phenyl, halogen or a straight-chain or branched alkyl or alkoxy containing up to 6 carbon atoms each, or $R_{VI-25}$ and $R_{VI-26}$ or $R_{VI-27}$ and $R_{VI-28}$ each together denote a straight-chain or branched alkyl chain containing up to 6 carbon atoms or $R_{VI-25}$ and $R_{VI-26}$ or $R_{VI-27}$ and $R_{VI-28}$ each together form a radical according to the formula

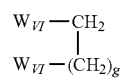

wherein $W_{VI}$ has the meaning given above, g is a number equaling 1, 2, 3, 4, 5, 6 or 7, $R_{VI-32}$ and $R_{VI-33}$ together form a 3- to 7-membered heterocycle, which contains an oxygen or sulfur atom or a group according to the formula SO, $SO_2$ or $BNR_{VI-34}$, wherein $R_{VI-34}$ denotes a hydrogen atom, a phenyl, benzyl, or a straight-chain or branched alkyl containing up to 4 carbon atoms, and salts and N oxides thereof, with the exception of 5(6H)-quinolones, 3-benzoyl-7,8-dihydro-2,7,7-trimethyl-4-phenyl.

Compounds of Formula VI and their methods of manufacture are disclosed in European Patent Application No. EP 818448 A1, U.S. Pat. No. 6,207,671 and U.S. Pat. No. 6,069,148, all of which are incorporated herein by reference in their entireties for all purposes.

In a preferred embodiment, the CETP inhibitor is selected from one of the following compounds of Formula VI:

2-cyclopentyl-4-(4-fluorophenyl)-7,7-dimethyl-3-(4-trifluoromethylbenzoyl)-4,6,7,8-tetrahydro-1H-quinolin-5-one;

2-cyclopentyl-4-(4-fluorophenyl)-7,7-dimethyl-3-(4-trifluoromethylbenzoyl)-7,8-dihydro-6H-quinolin-5-one;

[2-cyclopentyl-4-(4-fluorophenyl)-5-hydroxy-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol;

5-(t-butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline; and 2-cyclopentyl-4-(4-fluorophenyl)-3-[fluoro-(4-trifluoromethylphenyl)-methyl]-7,7-dimethyl-5,6,7,8-tetrahydroquinolin-5-ol.

Another class of CETP inhibitors that finds utility with the present invention consists of substituted-pyridines having the Formula VII Formula VII $$\begin{array}{c} R_{VII\text{-}4} \\ R_{VII\text{-}5} \quad\quad R_{VII\text{-}3} \\ R_{VII\text{-}6} \quad N \quad R_{VII\text{-}2} \end{array}$$

or a pharmaceutically acceptable salt or tautomer thereof, wherein $R_{VII\text{-}2}$ and $R_{VII\text{-}6}$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_{VII\text{-}2}$ and $R_{VII\text{-}6}$ is fluorinated alkyl, chlorofluorinated alkyl or alkoxyalkyl;

$R_{VII\text{-}3}$ is selected from the group consisting of hydroxy, amido, arylcarbonyl, heteroarylcarbonyl, hydroxymethyl —CHO, —$CO_2R_{VII\text{-}7}$, wherein $R_{VII\text{-}7}$ is selected from the group consisting of hydrogen, alkyl and cyanoalkyl; and $$\begin{array}{c} R_{VII\text{-}15a} \\ | \\ -C-R_{VII\text{-}16a} \\ | \\ H \end{array}$$

wherein $R_{VII\text{-}15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{VII\text{-}16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_{VII\text{-}4}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, hetereoarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclythioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, arylheteroarylamino, trialkylsilyl, trialkenylsilyl, triarylsilyl, —CO(O)N($R_{VII\text{-}8a}R_{VII\text{-}8b}$), wherein $R_{VII\text{-}8a}$ and $R_{VII\text{-}8b}$ are independently selected from the group consisting of alkyl, alkenyl, alkynyl, aryl, heteroaryl and heterocyclyl, —$SO_2R_{VII\text{-}9}$, wherein $R_{VII\text{-}9}$ is selected from the group consisting of hydroxy, alkyl, alkenyl, alkynyl, aryl, heteroaryl and heterocyclyl, —OP(O)(OR$_{VII\text{-}10a}$)(OR$_{VII\text{-}10b}$), wherein $R_{VII\text{-}10a}$ and $R_{VII\text{-}10b}$ are independently selected from the group consisting of hydrogen, hydroxy, alkyl, alkenyl, alkynyl, aryl, heteroaryl and heterocyclyl, and —OP(S) (OR$_{VII\text{-}11a}$)(OR$_{VII\text{-}11b}$), wherein $R_{VII\text{-}11a}$ and $R_{VII\text{-}11b}$ are independently selected from the group consisting of alkyl, alkenyl, alkynyl, aryl, heteroaryl and heterocyclyl;

$R_{VII\text{-}5}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxyalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl, —$CO_2R_{VII\text{-}14}$, wherein $R_{VII\text{-}14}$ is selected from the group consisting of alkyl, alkenyl, alkynyl, aryl, heteroaryl and heterocyclyl;

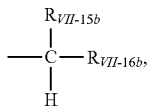

wherein $R_{VII-15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and $R_{VII-16b}$ is selected form the group consisting of alkyl, alkenyl, alkynyl, aryl, heteroaryl, heterocyclyl, arylalkoxy, and trialkylsilyloxy;

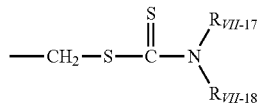

wherein $R_{VII-17}$ and $R_{VII-18}$ are independently selected from the group consisting of alkyl, cycloalkyl, alkenyl, alkynyl, aryl, heteroaryl and heterocyclyl;

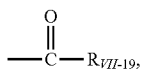

wherein $R_{VII-19}$ is selected from the group consisting of alkyl, cycloalkyl, alkenyl, alkynyl, aryl, heteroaryl, heterocyclyl, —$SR_{VII-20}$, —$OR_{VII-21}$, and $BR_{VII-22}CO_2R_{VII-23}$, wherein $R_{VII-20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, $R_{VII-21}$ is selected from the group consisting of alkyl, alkenyl, alkynyl, aryl, heteroaryl, and heterocyclyl, $R_{VII-22}$ is selected from the group consisting of alkylene or arylene, and $R_{VII-23}$ is selected from the group consisting of alkyl, alkenyl, alkynyl, aryl, heteroaryl, and heterocyclyl;

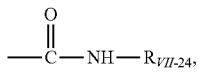

wherein $R_{VII-24}$ is selected from the group consisting of hydrogen, alkyl, cycloalkyl, alkenyl, alkynyl, aryl, heteroaryl, heterocyclyl, aralkyl, aralkenyl, and aralkynyl;

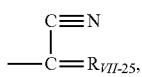

wherein $R_{VII-25}$ is heterocyclylidenyl;

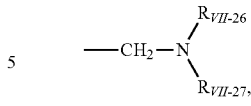

wherein $R_{VII-26}$ and $R_{VII-27}$ are independently selected from the group consisting of hydrogen, alkyl, cycloalkyl, alkenyl, alkynyl, aryl, heteroaryl, and heterocyclyl;

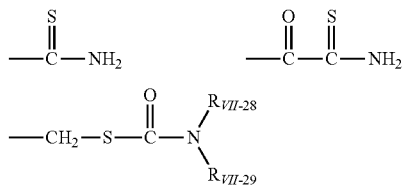

wherein $R_{VII-28}$ and $R_{VII-29}$ are independently selected from the group consisting of hydrogen, alkyl, cycloalkyl, alkenyl, alkynyl, aryl, heteroaryl, and heterocyclyl;

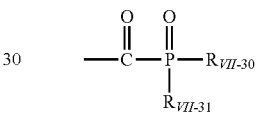

wherein $R_{VII-30}$ and $R_{VII-31}$ are independently alkoxy, alkenoxy, alkynoxy, aryloxy, heteroaryloxy, and heterocyclyloxy; and

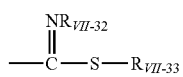

wherein $R_{VII-32}$ and $R_{VII-33}$ are independently selected from the group consisting of hydrogen, alkyl, cycloalkyl, alkenyl, alkynyl, aryl, heteroaryl, and heterocyclyl;

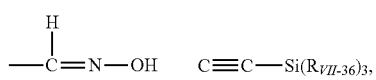

wherein $R_{VII-36}$ is selected from the group consisting of alkyl, alkenyl, aryl, heteroaryl and heterocyclyl;

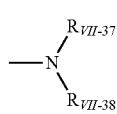

wherein $R_{VII-37}$ and $R_{VII-38}$ are independently selected from the group consisting of hydrogen, alkyl, cycloalkyl, alkenyl, alkynyl, aryl, heteroaryl, and heterocyclyl;

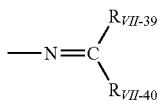

wherein $R_{VII-39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{VII-40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

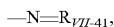

wherein $R_{VII-41}$ is heterocyclylidenyl;

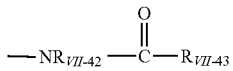

wherein $R_{VII-42}$ is selected from the group consisting of hydrogen, alkyl, alkenyl, alkynyl, aryl, heteroaryl, and heterocyclyl, and $R_{VII-43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

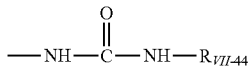

wherein $R_{VII-44}$ is selected from the group consisting of hydrogen, alkyl, cycloalkyl, alkenyl, alkynyl, aryl, heteroaryl and heterocyclyl;

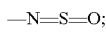

wherein $R_{VII-45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl,

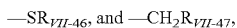

wherein $R_{VII-46}$ is selected from the group consisting of alkyl, alkenyl, alkynyl, aryl, heteroaryl and heterocyclyl, and $R_{VII-47}$ is selected from the group consisting of hydrogen, alkyl, alkenyl, alkynyl, aryl, heteroaryl and heterocyclyl; and

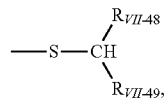

wherein $R_{VII-48}$ is selected from the group consisting of hydrogen, alkyl, cycloalkyl, alkenyl, alkynyl, aryl, heteroaryl and heterocyclyl, and $R_{VII-49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

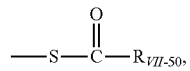

wherein $R_{VII-50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

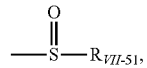

wherein $R_{VII-51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and

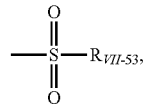

wherein $R_{VII-53}$ is selected from the group consisting of alkyl, alkenyl, alkynyl, aryl, heteroaryl and heterocyclyl;

provided that when $R_{VII-5}$ is selected from the group consisting of heterocyclylalkyl and heterocyclylalkenyl, the heterocyclyl radical of the corresponding heterocyclylalkyl or heterocyclylalkenyl is other than δ-lactone; and provided that when $R_{VII-4}$ is aryl, heteroaryl or heterocyclyl, and one of $R_{VII-2}$ and $R_{VII-6}$ is trifluoromethyl, then the other of $R_{VII-2}$ and $R_{VII-6}$ is difluoromethyl.

Compounds of Formula VII and their methods of manufacture are disclosed in PCT Publication No. WO 9941237-A1, which is incorporated herein by reference in its entirety for all purposes.

In a preferred embodiment, the CETP inhibitor of Formula VII is dimethyl 5,5-dithiobis[2-difluoromethyl-4-(2-methylpropyl)-6-(trifluoromethyl)-3-pyridine-carboxylate].

Another class of CETP inhibitors that finds utility with the present invention consists of substituted biphenyls having the Formula VIII

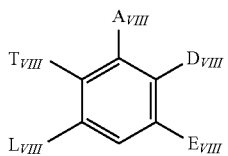

Formula VIII or a pharmaceutically acceptable salt, enantiomers, or stereoisomers thereof, in which $A_{VIII}$ stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-1}R_{VIII-2}$, wherein $R_{VIII-1}$ and $R_{VIII-2}$ are identical or different and denote hydrogen, phenyl, or straight-chain or branched alkyl with up to 6 carbon atoms, $D_{VIII}$ stands for straight-chain or branched alkyl with up to 8 carbon atoms, which is substituted by hydroxy, $E_{VIII}$ and $L_{VIII}$ are either identical or different and stand for straight-chain or branched alkyl with up to 8 carbon atoms, which is optionally substituted by cycloalkyl with 3 to 8 carbon atoms, or stands for cycloalkyl with 3 to 8 carbon atoms, or $E_{VIII}$ has the above-mentioned meaning and $L_{VIII}$ in this case stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-3}R_{VIII-4}$, wherein $R_{VIII-3}$ and $R_{VIII-4}$ are identical or different and have the meaning given above for $R_{VIII-1}$ and $R_{VIII-2}$, or $E_{VIII}$ stands for straight-chain or branched alkyl with up to 8 carbon atoms, or stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-5}R_{VIII-6}$, wherein $R_{VIII-5}$ and $R_{VIII-6}$ are identical or different and have the meaning given above for $R_{VIII-1}$ and $R_{VIII-2}$, and $L_{VIII}$ in this case stands for straight-chain or branched alkoxy with up to 8 carbon atoms or for cycloalkyloxy with 3 to 8 carbon atoms, $T_{VIII}$ stands for a radical of the formula $R_{VIII-7}$—$X_{VIII}$— or

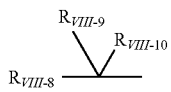

wherein $R_{VIII-7}$ and $R_{VIII-8}$ are identical or different and denote cycloalkyl with 3 to 8 carbon atoms, or aryl with 6 to 10 carbon atoms, or denote a 5- to 7-member aromatic, optionally benzo-condensed, heterocyclic compound with up to 3 heteroatoms from the series S, N and/or O, which are optionally substituted up to 3 times in an identical manner or differently by trifluoromethyl, trifluoromethoxy, halogen, hydroxy, carboxyl, by straight-chain or branched alkyl, acyl, alkoxy, or alkoxycarbonyl with up to 6 carbon atoms each, or by phenyl, phenoxy, or thiophenyl, which can in turn be substituted by halogen, trifluoromethyl, or trifluoromethoxy, and/or the rings are substituted by a group of the formula —$NR_{VIII-11}R_{VIII-12}$, wherein $R_{VIII-11}$ and $R_{VIII-12}$ are identical or different and have the meaning given above for $R_{VIII-1}$ and $R_{VII-2}$, $X_{VIII}$ denotes a straight or branched alkyl chain or alkenyl chain with 2 to 10 carbon atoms each, which are optionally substituted up to 2 times by hydroxy, $R_{VIII-9}$ denotes hydrogen, and $R_{VIII-10}$ denotes hydrogen, halogen, azido, trifluoromethyl, hydroxy, mercapto, trifluoromethoxy, straight-chain or branched alkoxy with up to 5 carbon atoms, or a radical of the formula —$NR_{VIII-13}R_{VIII-14}$, wherein $R_{VIII-13}$ and $R_{VIII-14}$ are identical or different and have the meaning given above for $R_{VIII-1}$ and $R_{VIII-2}$, or $R_{VIII-9}$ and $R_{VIII-10}$ form a carbonyl group together with the carbon atom.

Compounds of Formula VIII are disclosed in PCT Publication No. WO 9804528, which is incorporated herein by reference in its entirety for all purposes.

Another class of CETP inhibitors that finds utility with the present invention consists of substituted 1,2,4-triazoles having the Formula IX

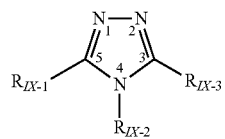

Formula IX or a pharmaceutically acceptable salt or tautomer thereof;

wherein $R_{IX-1}$ is selected from higher alkyl, higher alkenyl, higher alkynyl, aryl, aralkyl, aryloxyalkyl, alkoxyalkyl, alkylthioalkyl, arylthioalkyl, and cycloalkylalkyl;

wherein $R_{IX-2}$ is selected from aryl, heteroaryl, cycloalkyl, and cycloalkenyl, wherein $R_{IX-2}$ is optionally substituted at a substitutable position with one or more radicals independently selected from alkyl, haloalkyl, alkylthio, alkylsulfinyl, alkylsulfonyl, alkoxy, halo, aryloxy, aralkyloxy, aryl, aralkyl, aminosulfonyl, amino, monoalkylamino and dialkylamino; and wherein $R_{IX-3}$ is selected from hydrido, —SH and halo; provided $R_{IX-2}$ cannot be phenyl or 4-methylphenyl when $R_{IX-1}$ is higher alkyl and when $R_{IX-3}$ is BSH.

Compounds of Formula IX and their methods of manufacture are disclosed in PCT Publication No. WO 9914204, which is incorporated herein by reference in its entirety for all purposes.

In a preferred embodiment, the CETP inhibitor is selected from the following compounds of Formula IX:

2,4-dihydro-4-(3-methoxyphenyl)-5-tridecyl-3H-1,2,4-triazole-3-thione;
2,4-dihydro-4-(2-fluorophenyl)-5-tridecyl-3H-1,2,4-triazole-3-thione;
2,4-dihydro-4-(2-methylphenyl)-5-tridecyl-3H-1,2,4-triazole-3-thione;
2,4-dihydro-4-(3-chlorophenyl)-5-tridecyl-3H-1,2,4-triazole-3-thione;
2,4-dihydro-4-(2-methoxyphenyl)-5-tridecyl-3H-1,2,4-triazole-3-thione;
2,4-dihydro-4-(3-methylphenyl)-5-tridecyl-3H-1,2,4-triazole-3-thione;
4-cyclohexyl-2,4-dihydro-5-tridecyl-3H-1,2,4-triazole-3-thione;
2,4-dihydro-4-(3-pyridyl)-5-tridecyl-3H-1,2,4-triazole-3-thione;
2,4-dihydro-4-(2-ethoxyphenyl)-5-tridecyl-3H-1,2,4-triazole-3-thione;
2,4-dihydro-4-(2,6-dimethylphenyl)-5-tridecyl-3H-1,2,4-triazole-3-thione;
2,4-dihydro-4-(4-phenoxyphenyl)-5-tridecyl-3H-1,2,4-triazole-3-thione;
4-(1,3-benzodioxol-5-yl)-2,4-dihydro-5-tridecyl-3H-1,2,4-triazole-3-thione;
4-(2-chlorophenyl)-2,4-dihydro-5-tridecyl-3H-1,2,4-triazole-3-thione;
2,4-dihydro-4-(4-methoxyphenyl)-5-tridecyl-3H-1,2,4-triazole-3-thione;
2,4-dihydro-5-tridecyl-4-(3-trifluoromethylphenyl)-3H-1,2,4-triazole-3-thione;
2,4-dihydro-5-tridecyl-4-(3-fluorophenyl)-3H-1,2,4-triazole-3-thione;
4-(3-chloro-4-methylphenyl)-2,4-dihydro-5-tridecyl-3H-1,2,4-triazole-3-thione;
2,4-dihydro-4-(2-methylthiophenyl)-5-tridecyl-3H-1,2,4-triazole-3-thione;
4-(4-benzyloxyphenyl)-2,4-dihydro-5-tridecyl-3H-1,2,4-triazole-3-thione;
2,4-dihydro-4-(2-naphthyl)-5-tridecyl-3H-1,2,4-triazole-3-thione;
2,4-dihydro-5-tridecyl-4-(4-trifluoromethylphenyl)-3H-1,2,4-triazole-3-thione;
2,4-dihydro-4-(1-naphthyl)-5-tridecyl-3H-1,2,4-triazole-3-thione;
2,4-dihydro-4-(3-methylthiophenyl)-5-tridecyl-3H-1,2,4-triazole-3-thione;
2,4-dihydro-4-(4-methylthiophenyl)-5-tridecyl-3H-1,2,4-triazole-3-thione;
2,4-dihydro-4-(3,4-dimethoxyphenyl)-5-tridecyl-3H-1,2,4-triazole-3-thione;
2,4-dihydro-4-(2,5-dimethoxyphenyl)-5-tridecyl-3H-1,2,4-triazole-3-thione;
2,4-dihydro-4-(2-methoxy-5-chlorophenyl)-5-tridecyl-3H-1,2,4-triazole-3-thione;
4-(4-aminosulfonylphenyl)-2,4-dihydro-5-tridecyl-3H-1,2,4-triazole-3-thione;
2,4-dihydro-5-dodecyl-4-(3-methoxyphenyl)-3H-1,2,4-triazole-3-thione;
2,4-dihydro-4-(3-methoxyphenyl)-5-tetradecyl-3H-1,2,4-triazole-3-thione;
2,4-dihydro-4-(3-methoxyphenyl)-5-undecyl-3H-1,2,4-triazole-3-thione; and
2,4-dihydro-(4-methoxyphenyl)-5-pentadecyl-3H-1,2,4-triazole-3-thione.

Another class of CETP inhibitors that finds utility with the present invention consists of hetero-tetrahydroquinolines having the Formula X

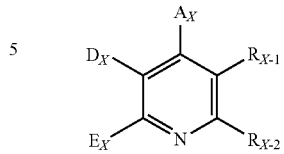

Formula X and pharmaceutically acceptable salts, enantiomers, or stereoisomers or N-oxides of said compounds;
in which $A_X$ represents cycloalkyl with 3 to 8 carbon atoms or a 5 to 7-membered, saturated, partially saturated or unsaturated, optionally benzo-condensed heterocyclic ring containing up to 3 heteroatoms from the series comprising S, N and/or O, that in case of a saturated heterocyclic ring. is bonded to a nitrogen function, optionally bridged over it, and in which the aromatic systems mentioned above are optionally substituted up to 5-times in an identical or different substituents in the form of halogen, nitro, hydroxy, trifluoromethyl, trifluoromethoxy or by a straight-chain or branched alkyl, acyl, hydroxyalkyl or alkoxy each having up to 7 carbon atoms or by a group of the formula $BNR_{X-3}R_{X-4}$,
in which $R_{X-3}$ and $R_{X-4}$ are identical or different and denote hydrogen, phenyl or straight-chain or branched alkyl having up to 6 carbon atoms,
or $A_X$ represents a radical of the formula

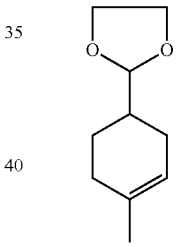

$D_X$ represents an aryl having 6 to 10 carbon atoms, that is optionally substituted by phenyl, nitro, halogen, trifluormethyl or trifluormethoxy, or it represents a radical of the formula

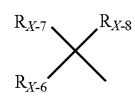

$R_{X-5}$-$L_X$, or $R_{X-9}$—$T_X$—$V_X$—$X_X$ in which $R_{X-5}$, $R_{X-6}$ and $R_{X-9}$ independently of one another denote cycloalkyl having 3 to 6 carbon atoms, or an aryl having 6 to 10 carbon atoms or a 5- to 7-membered aromatic, optionally benzo-condensed saturated or unsaturated, mono-, bi-, or tricyclic heterocyclic ring from the series consisting of S, N and/or O, in which the rings are substituted, optionally, in case of the nitrogen containing aromatic rings via the N function, with up to 5 identical or different substituents in the form of halogen, trifluoromethyl, nitro, hydroxy, cyano, carbonyl, trifluoromethoxy, straight straight-chain or branched acyl, alkyl, alkylthio, alkylalkoxy, alkoxy, or alkoxycarbonyl each having up to 6 carbon atoms, by aryl or trifluoromethyl-substituted aryl each having 6 to 10 carbon atoms or by an, optionally benzo-condensed, aromatic 5- to 7-membered heterocyclic ring having up to 3 heteroatoms from the series consisting of S, N, and/or O, and/or substituted by a group of the formula $BOR_{X-10}$, $-SR_{X-11}$, $SO_2R_{X-12}$ or $BNR_{X-13}R_{X-14}$, in which $R_{X-10}$, $R_{X-11}$ and $R_{X-12}$ independently from each other denote aryl having 6 to 10 carbon atoms, which is in turn substituted with up to 2 identical or different substituents in the form of phenyl, halogen or a straight-chain or branched alkyl having up to 6 carbon atoms, $R_{X-13}$ and $R_{X-14}$ are identical or different and have the meaning of $R_{X-3}$ and $R_{X-4}$ indicated above, or $R_{X-5}$ and/or $R_{X-6}$ denote a radical of the formula

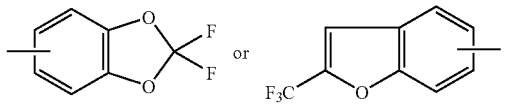

$R_{X-7}$ denotes hydrogen or halogen, and $R_{X-8}$ denotes hydrogen, halogen, azido, trifluoromethyl, hydroxy, trifluoromethoxy, straight-chain or branched alkoxy or alkyl having up to 6 carbon atoms or a radical of the formula $BNR_{X-15}R_{X-16}$, in which $R_{X-15}$ and $R_{X-16}$ are identical or different and have the meaning of $R_{X-3}$ and $R_{X-4}$ indicated above, or $R_{X-7}$ and $R_{X-8}$ together form a radical of the formula $=O$ or $=NR_{X-17}$, in which $R_{X-17}$ denotes hydrogen or straight chain or branched alkyl, alkoxy or acyl having up to 6 carbon atoms, $L_X$ denotes a straight chain or branched alkylene or alkenylene chain having up to 8 carbon atoms, that are optionally substituted with up to 2 hydroxy groups, $T_X$ and $X_X$ are identical or different and denote a straight chain or branched alkylene chain with up to 8 carbon atoms or $T_X$ or $X_X$ denotes a bond, $V_X$ represents an oxygen or sulfur atom or an $BNR_{X-18}$-group, in which $R_{X-18}$ denotes hydrogen or straight chain or branched alkyl with up to 6 carbon atoms or phenyl, $E_X$ represents cycloalkyl with 3 to 8 carbon atoms, or straight chain or branched alkyl with up to 8 carbon atoms, that is optionally substituted by cycloalkyl with 3 to 8 carbon atoms or hydroxy, or represents a phenyl, that is optionally substituted by halogen or trifluoromethyl, $R_{X-1}$ and $R_{X-2}$ together form a straight-chain or branched alkylene chain with up to 7 carbon atoms, that must be substituted by carbonyl group and/or by a radical with the formula

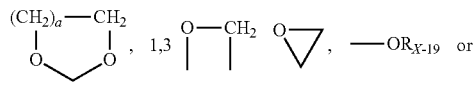

-continued

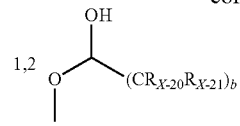

in which a and b are identical or different and denote a number equaling 1, 2, or 3, $R_{X-19}$ denotes hydrogen, cycloalkyl with 3 up to 7 carbon atoms, straight chain or branched silylalkyl with up to 8 carbon atoms or straight chain or branched alkyl with up to 8 carbon atoms, that are optionally substituted by hydroxyl, straight chain or branched alkoxy with up to 6 carbon atoms or by phenyl, which in turn might be substituted by halogen, nitro, trifluormethyl, trifluoromethoxy or by phenyl or by tetrazole-substituted phenyl, and alkyl, optionally be substituted by a group with the formula $BOR_{X-22}$, in which $R_{X-22}$ denotes a straight chain or branched acyl with up to 4 carbon atoms or benzyl, or $R_{X-19}$ denotes straight chain or branched acyl with up to 20 carbon atoms or benzoyl, that is optionally substituted by halogen, trifluoromethyl, nitro or trifluoromethoxy, or it denotes straight chain or branched fluoroacyl with up to 8 carbon atoms and 9 fluorine atoms, $R_{X-20}$ and $R_{X-21}$ are identical or different and denote hydrogen, phenyl or straight chain or branched alkyl with up to 6 carbon atoms, or $R_{X-20}$ and $R_{X-21}$ together form a 3- to 6-membered carbocyclic ring, and the carbocyclic rings formed are optionally substituted, optionally also geminally, with up to six identical or different substituents in the form of triflouromethyl, hydroxy, nitrile, halogen, carboxyl, nitro, azido, cyano, cycloalkyl or cycloalkyloxy with 3 to 7 carbon atoms each, by straight chain or branched alkoxycarbonyl, alkoxy or alkylthio with up to 6 carbon atoms each or by straight chain or branched alkyl with up to 6 carbon atoms, which in turn is substituted with up to 2 identically or differently by hydroxyl, benzyloxy, trifluoromethyl, benzoyl, straight chain or branched alkoxy, oxyacyl or carbonyl with up to 4 carbon atoms each and/or phenyl, which may in turn be substituted with a halogen, trifuoromethyl or trifluoromethoxy, and/or the formed carbocyclic rings are optionally substituted, also geminally, with up to 5 identical or different substituents in the form of phenyl, benzoyl, thiophenyl or sulfonylbenzyl, which in turn are optionally substituted by halogen, trifluoromethyl, trifluoromethoxy or nitro, and/or optionally are substituted by a radical with the formula

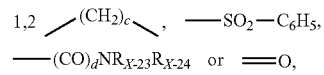

in which c denotes a number equaling 1, 2, 3, or 4, d denotes a number equaling 0 or 1, $R_{X-23}$ and $R_{X-24}$ are identical or different and denote hydrogen, cycloalkyl with 3 to 6 carbon atoms, straight chain or branched alkyl with up to 6 carbon atoms, benzyl or phenyl, that is optionally substituted with up to 2 identically or differently by halogen, trifluoromethyl, cyano, phenyl or nitro, and/or the formed carbocyclic rings are substituted optionally by a spiro-linked radical with the formula

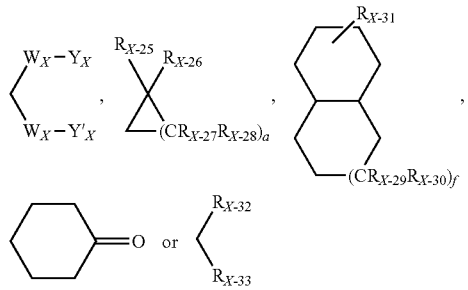

in which
$W_X$ denotes either an oxygen or a sulfur atom
$Y_X$ and $Y'_X$ together form a 2 to 6 membered straight chain or branched alkylene chain,
e denotes a number equaling 1, 2, 3, 4, 5, 6, or 7,
f denotes a number equaling 1 or 2,
$R_{X-25}$, $R_{X-26}$, $R_{X-27}$, $R_{X-28}$, $R_{X-29}$, $R_{X-30}$ and $R_{X-31}$ are identical or different and denote hydrogen, trifluoromethyl, phenyl, halogen or straight chain or branched alkyl or alkoxy with up to 6 carbon atoms each,
or
$R_{X-25}$ and $R_{X-26}$ or $R_{X-27}$ and $R_{X-28}$ respectively form together a straight chain or branched alkyl chain with up to 6 carbon atoms,
or
$R_{X-25}$ and $R_{X-26}$ or $R_{X-27}$ and $R_{X-28}$ each together form a radical with the formula

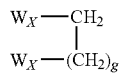

in which
$W_X$ has the meaning given above,
g denotes a number equaling 1, 2, 3, 4, 5, 6, or 7,
$R_{X-32}$ and $R_{X-33}$ form together a 3- to 7-membered heterocycle, which contains an oxygen or sulfur atom or a group with the formula SO, $SO_2$ or $—NR_{X-34}$,
in which
$R_{X-34}$ denotes hydrogen, phenyl, benzyl or straight or branched alkyl with up to 4 carbon atoms.

Compounds of Formula X and their methods of manufacture are disclosed in PCT Publication No. WO 9914215, which is incorporated herein by reference in its entirety for all purposes.

In a preferred embodiment, the CETP inhibitor is selected from the following compounds of Formula X:
2-cyclopentyl-5-hydroxy-7,7-dimethyl-4-(3-thienyl)-3-(4-trifluoromethylbenxoyl)-5,6,7,8-tetrahydroquinoline;
2-cyclopentyl-3-[fluoro-(4-trifluoromethylphenyl)methyl]-5-hydroxy-7,7-dimethyl-4-(3-thienyl)-5,6,7,8-tetrahydroquinoline; and
2-cyclopentyl-5-hydroxy-7,7-dimethyl-4-(3-thienyl)-3-(trifluoromethylbenxyl)-5,6,7,8-tetrahydroquinoline.

Another class of CETP inhibitors that finds utility with the present invention consists of substituted tetrahydro naphthalines and analogous compound having the Formula XI

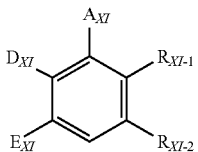

and stereoisomers, stereoisomer mixtures, and salts thereof, in which
$A_{XI}$ stands for cycloalkyl with 3 to 8 carbon atoms, or stands for aryl with 6 to 10 carbon atoms, or stands for a 5- to 7-membered, saturated, partially unsaturated or unsaturated, possibly benzocondensated, heterocycle with up to 4 heteroatoms from the series S, N and/or O, where aryl and the heterocyclic ring systems mentioned above are substituted up to 5-fold, identical or different, by cyano, halogen, nitro, carboxyl, hydroxy, trifluoromethyl, trifluoro-methoxy, or by straight-chain or branched alkyl, acyl, hydroxyalkyl, alkylthio, alkoxycarbonyl, oxyalkoxycarbonyl or alkoxy each with up to 7 carbon atoms, or by a group of the formula $$—NR_{XI-3}R_{XI-4},$$

in which
$R_{XI-3}$ and $R_{XI-4}$ are identical or different and denote hydrogen, phenyl, or straight-chain or branched alkyl with up to 6 carbon atoms
$D_{XI}$ stands for a radical of the formula $$R_{XI-5}\text{-}L_{XI},$$

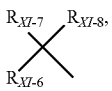

or $$R_{XI-9}—T_{XI}—V_{XI}—X_{XI}—,$$

in which
$R_{XI-5}$, $R_{XI-6}$ and $R_{XI-9}$, independent of each other, denote cycloalkyl with 3 to 6 carbon atoms, or denote aryl with 6 to 10 carbon atoms, or denote a 5- to 7-membered, possibly benzocondensated, saturated or unsaturated, mono-, bi- or tricyclic heterocycle with up to 4 heteroatoms of the series S, N and/or O, where the cycles are possibly substitutedCin the case of the nitrogen-containing rings also via the N-function-Cup to 5-fold, identical or different, by halogen, trifluoromethyl. nitro, hydroxy, cyano, carboxyl, trifluoromethoxy, straight-chain or branched acyl, alkyl, alkylthio, alkylalkoxy, alkoxy or alkoxycarbonyl with up to 6 carbon atoms each. by aryl or trifluoromethyl substituted aryl with 6 to 10 carbon atoms each, or by a possibly benzocondensated aromatic 5- to 7-membered heterocycle with up to 3 heteroatoms of the series S, N and/or O, and/or are substituted by a group of the formula $$—OR_{XI-10}, —SR_{XI-11}, —SO_2R_{XI-12} \text{ or } —NR_{XI-13}R_{XI-14},$$

in which
$R_{XI-10}$, $R_{XI-11}$ and $R_{XI-12}$, independent of each other, denote aryl with 6 to 10 carbon atoms, which itself is substituted up to 2-fold, identical or different, by phenyl, halogen. or by straight-chain or branched alkyl with up to 6 carbon atoms, $R_{XI-13}$ and $R_{XI-14}$ are identical or different and have the meaning given above for $R_{XI-3}$ and $R_{XI-4}$,
or
$R_{XI-5}$ and/or $R_{XI-6}$ denote a radical of the formula

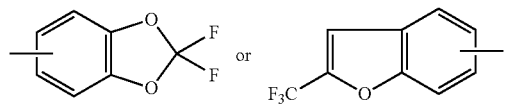

$R_{XI-7}$ denotes hydrogen, halogen or methyl,
and
$R_{XI-8}$ denotes hydrogen, halogen, azido, trifluoromethyl, hydroxy, trifluoromethoxy, straight-chain or branched alkoxy or alkyl with up to 6 carbon atoms each, or a radical of the formula —$NR_{XI-15}R_{XI-16}$,
in which
$R_{XI-15}$ and $R_{XI-16}$ are identical or different and have the meaning given above for $R_{XI-3}$ and $R_{XI-4}$,
or
$R_{XI-7}$ and $R_{XI-8}$ together form a radical of the formula =O or =$NR_{XI-17}$, in which
$R_{XI-17}$ denotes hydrogen or straight-chain or branched alkyl, alkoxy or acyl with up to 6 carbon atoms each,
$L_{XI}$ denotes a straight-chain or branched alkylene- or alkenylene chain with up to 8 carbon atoms each, which is possibly substituted up to 2-fold by hydroxy,
$T_{XI}$ and $X_{XI}$ are identical or different and denote a straight-chain or branched alkylene chain with up to 8 carbon atoms,
or
$T_{XI}$ and $X_{XI}$ denotes a bond,
$V_{XI}$ stands for an oxygen- or sulfur atom or for an —$NR_{XI-18}$ group,
in which
$R_{XI-18}$ denotes hydrogen or straight-chain or branched alkyl with up to 6 carbon atoms, or phenyl,
$E_{XI}$ stands for cycloalkyl with 3 to 8 carbon atoms, or stands for straight-chain or branched alkyl with up to 8 carbon atoms, which is possibly substituted by cycloalkyl with 3 to 8 carbon atoms or hydroxy, or stands for phenyl, which is possibly substituted by halogen or trifluoromethyl,
$R_{XI-1}$ and $R_{XI-2}$ together form a straight-chain or branched alkylene chain with up to 7 carbon atoms, which must be substituted by a carbonyl group and/or by a radical of the formula

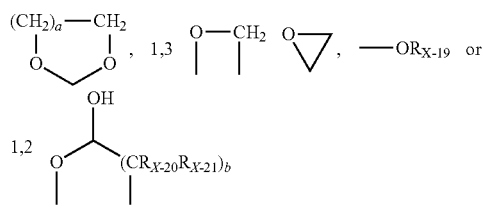

in which
a and b are identical or different and denote a number 1, 2 or 3
$R_{XI-19}$ denotes hydrogen, cycloalkyl with 3 to 7 carbon atoms, straight-chain or branched silylalkyl with up to 8 carbon atoms, or straight-chain or branched alkyl with up to 8 carbon atoms, which is possibly substituted by hydroxy, straight-chain or branched alkoxy with up to 6 carbon atoms, or by phenyl, which itself can be substituted by halogen, nitro, trifluoromethyl, trifluoromethoxy or by phenyl substituted by phenyl or tetrazol, and alkyl is possibly substituted by a group of the formula —$OR_{XI-22}$,
in which
$R_{XI-22}$ denotes straight-chain or branched acyl with up to 4 carbon atoms, or benzyl,
or
$R_{XI-19}$ denotes straight-chain or branched acyl with up to 20 carbon atoms or benzoyl, which is possibly substituted by halogen, trifluoromethyl, nitro or trifluoromethoxy, or denotes straight-chain or branched fluoroacyl with up to 8 carbon atoms and 9 fluorine atoms,
$R_{XI-20}$ and $R_{XI-21}$ are identical or different, denoting hydrogen, phenyl or straight-chain or branched alkyl with up to 6 carbon atoms,
or
$R_{XI-20}$ and $R_{XI-21}$ together form a 3- to 6-membered carbocycle, and, possibly also geminally, the alkylene chain formed by $R_{XI-1}$ and $R_{XI-2}$, is possibly substituted up to 6-fold, identical or different, by trifluoromethyl, hydroxy, nitrile, halogen, carboxyl, nitro, azido, cyano, cycloalkyl or cycloalkyloxy with 3 to 7 carbon atoms each, by straight-chain or branched alkoxycarbonyl, alkoxy or alkoxythio with up to 6 carbon atoms each, or by straight-chain or branched alkyl with up to 6 carbon atoms, which itself is substituted up to 2-fold,
identical or different. by hydroxyl, benzyloxy, trifluoromethyl, benzoyl, straight-chain or branched alkoxy, oxyacyl or carboxyl with up to 4 carbon atoms each, and/or phenyl which itself can be substituted by halogen, trifluoromethyl or trifluoromethoxy, and/or the alkylene chain formed by $R_{XI-1}$ and $R_{XI-2}$ is substituted, also geminally, possibly up to 5-fold, identical or different, by phenyl, benzoyl, thiophenyl or sulfobenzyl which themselves are possibly substituted by halogen, trifluoromethyl, trifluoromethoxy or nitro, and/or the alkylene chain formed by $R_{XI-1}$ and $R_{XI-2}$ is possibly substituted by a radical of the formula

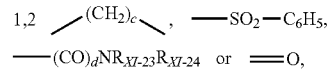

in which
c denotes a number 1, 2, 3 or 4,
d denotes a number 0 or 1,
$R_{XI-23}$ and $R_{XI-24}$ are identical or different and denote hydrogen, cycloalkyl with 3 to 6 carbon atoms, straight-chain or branched alkyl with up to 6 carbon atoms, benzyl or phenyl, which is possibly substituted up to 2-fold. identical or different, by halogen, trifluoromethyl, cyano, phenyl or nitro, and/or the alkylene chain formed by $R_{XI-1}$ and $R_{XI-2}$ is possibly substituted by a spiro-jointed radical of the formula

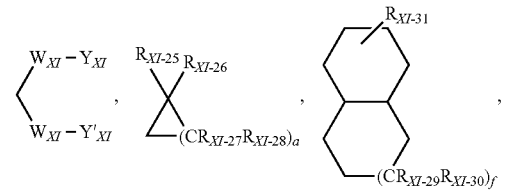

-continued

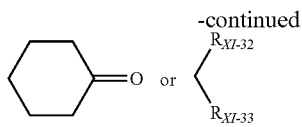

in which
W$_{XI}$ denotes either an oxygen or a sulfur atom,
Y$_{XI}$ and Y'$_{XI}$ together form a 2- to 6-membered straight-chain or branched alkylene chain,
e is a number 1, 2, 3, 4, 5, 6 or 7,
f denotes a number 1 or 2,
R$_{XI-25}$, R$_{XI-26}$, R$_{XI-27}$, R$_{XI-28}$, R$_{XI-29}$, R$_{XI-30}$ and R$_{XI-31}$ are identical or different and denote hydrogen, trifluoromethyl, phenyl, halogen, or straight-chain or branched alkyl or alkoxy with up to 6 carbon atoms each,
or
R$_{XI-25}$ and R$_{XI-26}$ or R$_{XI-27}$ and R$_{XI-28}$ together form a straight-chain or branched alkyl chain with up to 6 carbon atoms,
or
R$_{XI-25}$ and R$_{XI-26}$ or R$_{XI-27}$ and R$_{XI-28}$ together form a radical of the formula

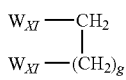

in which
W$_{XI}$ has the meaning given above,
g is a number 1, 2, 3, 4, 5, 6 or 7,
R$_{XI-32}$ and R$_{XI-33}$ together form a 3- to 7-membered heterocycle that contains an oxygen- or sulfur atom or a group of the formula SO, SO$_2$ or —NR$_{XI-34}$,
in which
R$_{XI-34}$ denotes hydrogen, phenyl, benzyl, or straight-chain or branched alkyl with up to 4 carbon atoms.

Compounds of Formula XI and their methods of manufacture are disclosed in PCT Publication No. WO 9914174, which is incorporated herein by reference in its entirety for all purposes.

Another class of CETP inhibitors that finds utility with the present invention consists of 2-aryl-substituted pyridines having the Formula (XII)

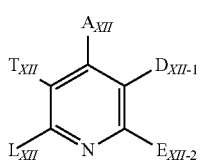

Formula XII or pharmaceutically acceptable salts, enantiomers, or stereoisomers of said compounds,
in which
A$_{XII}$ and E$_{XII}$ are identical or different and stand for aryl with 6 to 10 carbon atoms which is possibly substituted, up to 5-fold identical or different, by halogen, hydroxy, trifluoromethyl, trifluoromethoxy, nitro or by straight-chain or branched alkyl, acyl, hydroxy alkyl or alkoxy with up to 7 carbon atoms each, or by a group of the formula —NR$_{XII-1}$R$_{XII-2}$ where
R$_{XII-1}$ and R$_{XII-2}$ are identical or different and are meant to be hydrogen, phenyl or straight-chain or branched alkyl with up to 6 carbon atoms,
D$_{XII}$ stands for straight-chain or branched alkyl with up to 8 carbon atoms, which is substituted by hydroxy,
L$_{XII}$ stands for cycloalkyl with 3 to 8 carbon atoms or for straight-chain or branched alkyl with up to 8 carbon atoms, which is possibly substituted by cycloalkyl with 3 to 8 carbon atoms, or by hydroxy,
T$_{XII}$ stands for a radical of the formula R$_{XII-3}$—X$_{XII}$— or

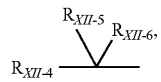

where
R$_{XII-3}$ and R$_{XII-4}$ are identical or different and are meant to be cycloalkyl with 3 to 8 carbon atoms, or aryl with 6 to 10 carbon atoms, or a 5- to 7-membered aromatic, possibly benzocondensated heterocycle with up to 3 heteroatoms from the series S, N and/or O, which are possibly substituted. up to 3-fold identical or different, by trifluoromethyl, trifluoromethoxy, halogen, hydroxy, carboxyl, nitro, by straight-chain or branched alkyl, acyl, alkoxy or alkoxycarbonyl with up to 6 carbon atoms each, or by phenyl, phenoxy or phenylthio which in turn can be substituted by halogen, trifluoromethyl or trifluoromethoxy, and/or where the cycles are possibly substituted by a group of the formula —NR$_{XII-7}$R$_{XII-8}$,
where
R$_{XII-7}$ and R$_{XII-8}$ are identical or different and have the meaning of R$_{XII-1}$ and R$_{XII-2}$ given above,
X$_{XII}$ is a straight-chain or branched alkyl or alkenyl with 2 to 10 carbon atoms each, possibly substituted up to 2-fold by hydroxy or halogen,
R$_{XII-5}$ stands for hydrogen,
and
R$_{XII-6}$ means to be hydrogen, halogen, mercapto, azido, trifluoromethyl, hydroxy, trifluoromethoxy, straight-chain or branched alkoxy with up to 5 carbon atoms, or a radical of the formula BNR$_{XII-1}$R$_{XII-10}$,
where
R$_{XII-9}$ and R$_{XII-10}$ are identical or different and have the meaning of R$_{XII-1}$ and R$_{XII-2}$ given above,
or
R$_{XII-5}$ and R$_{XII-6}$, together with the carbon atom, form a carbonyl group.

Compounds of Formula XII and their methods of manufacture are disclosed in EP 796846-A1, U.S. Pat. No. 6,127,383 and U.S. Pat. No. 5,925,645, all of which are incorporated herein by reference in their entireties for all purposes.

In a preferred embodiment, the CETP inhibitor is selected from the following compounds of Formula XII:
4,6-bis-(p-fluorophenyl)-2-isopropyl-3-[(p-trifluoromethylphenyl)-(fluoro)methyl]-5-(1-hydroxyethyl)pyridine;
2,4-bis-(4-fluorophenyl)-6-isopropyl-5-[4-(trifluoromethylphenyl)-fluoromethyl]-3-hydroxymethyl)pyridine; and
2,4-bis-(4-fluorophenyl)-6-isopropyl-5-[2-(3-trifluoromethylphenyl)vinyl]-3-hydroxymethyl)pyridine.

Another class of CETP inhibitors that finds utility with the present invention consists of compounds having the Formula (XIII)

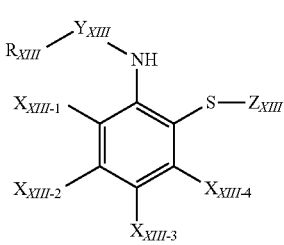

Formula XIII

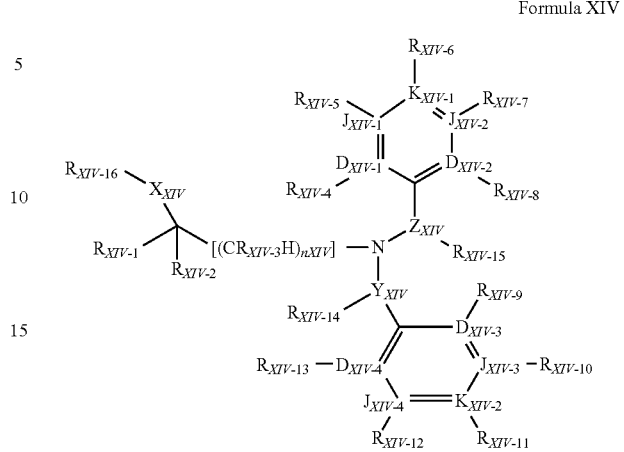

Formula XIV or pharmaceutically acceptable salts, enantiomers, stereoisomers, hydrates, or solvates of said compounds, in which $R_{XIII-1}$ is a straight chain or branched $C_{1-10}$ alkyl; straight chain or branched $C_{2-10}$ alkenyl; halogenated $C_{1-4}$ lower alkyl; $C_{3-10}$ cycloalkyl that may be substituted; $C_{5-8}$ cycloalkenyl that may be substituted; $C_{3-10}$ cycloalkyl $C_{1-10}$ alkyl that may be substituted; aryl that may be substituted; aralkyl that may be substituted; or a 5- or 6-membered heterocyclic group having 1 to 3 nitrogen atoms, oxygen atoms or sulfur atoms that may be substituted, $X_{XIII-1}$, $X_{XIII-2}$, $X_{XIII-3}$, $X_{XIII-4}$ may be the same or different and are a hydrogen atom; halogen atom; $C_{1-4}$ lower alkyl; halogenated $C_{1-4}$ lower alkyl; $C_{1-4}$ lower alkoxy; cyano group; nitro group; acyl; or aryl, respectively;

$Y_{XIII}$ is —CO—; or $BSO_2$—; and $Z_{XIII}$ is a hydrogen atom; or mercapto protective group.

Compounds of Formula XIII and their methods of manufacture are disclosed in PCT Publication No. WO 98/35937, which is incorporated herein by reference in its entirety for all purposes.

In a preferred embodiment, the CETP inhibitor is selected from the following compounds of Formula XIII:

N,N'-(dithiodi-2,1-phenylene)bis[2,2-dimethyl-propanamide];

N,N'-(dithiodi-2,1-phenylene)bis[1-methyl-cyclohexanecarboxamide];

N,N'-(dithiodi-2,1-phenylene)bis[1-(3-methylbutyl)-cyclopentanecarboxamide];

N,N'-(dithiodi-2,1-phenylene)bis[1-(3-methylbutyl)-cyclohexanecarboxamide];

N,N'-(dithiodi-2,1-phenylene)bis[1-(2-ethylbutyl)-cyclohexanecarboxamide];

N,N'-(dithiodi-2,1-phenylene)bis-tricyclo[3.3.1.1$^{3,7}$]decane-1-carboxamide;

propanethioic acid, 2-methyl-,S-[2[[[1-(2-ethylbutyl)cyclohexyl]carbonyl]amino]phenyl]ester;

propanethioic acid, 2,2-dimethyl-, S-[2-[[[1-(2-ethylbutyl)cyclohexyl]carbonyl]amino]phenyl]ester; and ethanethioic acid, S-[2-[[[1-(2-ethylbutyl)cyclohexyl]carbonyl]amino]phenyl]ester.

Another class of CETP inhibitors that finds utility with the present invention consists of polycyclic aryl and heteroaryl tertiary-heteroalkylamines having the Formula XIV and pharmaceutically acceptable forms thereof, wherein:

$n_{XIV}$ is an integer selected from 0 through 5;

$R_{XIV-1}$ is selected from the group consisting of haloalkyl, haloalkenyl, haloalkoxyalkyl, and haloalkenyloxyalkyl;

$X_{XIV}$ is selected from the group consisting of O, H, F, S, S(O), NH, N(OH), N(alkyl), and N(alkoxy);

$R_{XIV-16}$ is selected from the group consisting of hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, dialkoxyphosphonoalkyl, trialkylsilyl, and a spacer selected from the group consisting of a covalent single bond and a linear spacer moiety having from 1 through 4 contiguous atoms linked to the point of bonding of an aromatic substituent selected from the group consisting of $R_{XIV-4}$, $R_{XIV-8}$, $R_{XIV-9}$, and $R_{XIV-13}$ to form a heterocyclyl ring having from 5 through 10 contiguous members with the provisos that said spacer moiety is other than a covalent single bond when $R_{XIV-2}$ is alkyl and there is no $R_{XIV-16}$ wherein X is H or F;

$D_{XIV-1}$, $D_{XIV-2}$, $J_{XIV-1}$, $J_{XIV-2}$ and $K_{XIV-1}$ are independently selected from the group consisting of C, N, O, S and a covalent bond with the provisos that no more than one of $D_{XIV-1}$, $D_{XIV-2}$, $J_{XIV-1}$, $J_{XIV-2}$ and $K_{XIV-1}$ is a covalent bond, no more than one of $D_{XIV-1}$, $D_{XIV-2}$, $J_{XIV-1}$, $J_{XIV-2}$ and $K_{XIV-1}$ is O, no more than one of $D_{XIV-1}$, $D_{XIV-2}$, $J_{XIV-1}$, $J_{XIV-2}$ and $K_{XIV-1}$ is S, one of $D_{XIV-1}$, $D_{XIV-2}$, $J_{XIV-1}$, $J_{XIV-2}$ and $K_{XIV-1}$ must be a covalent bond when two of $D_{XIV-1}$, $D_{XIV-2}$, $J_{XIV-1}$, $J_{XIV-2}$ and $K_{XIV-1}$ are O and S, and no more than four of $D_{XIV-1}$, $D_{XIV-2}$, $J_{XIV-1}$, $J_{XIV-2}$ and $K_{XIV-1}$ are N;

$D_{XIV-3}$, $D_{XIV-4}$, $J_{XIV-3}$, $J_{XIV-4}$ and $K_{XIV-2}$ are independently selected from the group consisting of C, N, O, S and a covalent bond with the provisos that no more than one of $D_{XIV-3}$, $D_{XIV-4}$, $J_{XIV-3}$, $J_{XIV-4}$ and $K_{XIV-2}$ is a covalent bond, no more than one of $D_{XIV-3}$, $D_{XIV-4}$, $J_{XIV-3}$, $J_{XIV-4}$ and $K_{XIV-2}$ is O, no more than one of $D_{XIV-3}$, $D_{XIV-4}$, $J_{XIV-3}$, $J_{XIV-4}$ and $K_{XIV-2}$ is S, one of $D_{XIV-3}$, $D_{XIV-4}$, $J_{XIV-3}$, $J_{XIV-4}$ and $K_{XIV-2}$ must be a covalent bond when two of $D_{XIV-3}$, $D_{XIV-4}$, $J_{XIV-3}$, $J_{XIV-4}$ and $K_{XIV-2}$ are O and S, and no more than four of $D_{XIV-3}$, $D_{XIV-4}$, $J_{XIV-3}$, $J_{XIV-4}$ and $K_{XIV-2}$ and $K_{XIV-2}$ are N;

$R_{XIV-2}$ is independently selected from the group consisting of hydrido, hydroxy, hydroxyalkyl, amino, aminoalkyl, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, aloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$R_{XIV-2}$ and $R_{XIV-3}$ are taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

$R_{XIV-3}$ is selected from the group consisting of hydrido, hydroxy, halo, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$Y_{XIV}$ is selected from a group consisting of a covalent single bond, $(C(R_{XIV-14})_2)_{qXIV}$ wherein $_{qXIV}$ is an integer selected from 1 and 2 and $(CH(R_{XIV-14}))_{gXIV}$—$W_{XIV}$—$(CH(R_{XIV-14}))_{pXIV}$ wherein $_{gXIV}$ and $_{pXIV}$ are integers independently selected from 0 and 1;

$R_{XIV-14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-9}$ and $R_{XIV-13}$ to form a ring selected from the group consisting of a cycloalkenyl ring having from 5 through 8 contiguous members and a heterocyclyl ring having from 5 through 8 contiguous members and a spacer selected from a moiety having a chain length of 2 to 5 atoms connected to the point of bonding selected from the group consisting of $R_{XIV-4}$ and $R_{XIV-8}$ to form a heterocyclyl having from 5 through 8 contiguous members with the proviso that, when $Y_{XIV}$ is a covalent bond, an $R_{XIV-14}$ substituent is not attached to $Y_{XIV}$;

$R_{XIV-14}$ and $R_{XIV-14}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-14}$ and $R_{XIV-14}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$W_{XIV}$ is selected from the group consisting of O, C(O), C(S), C(O)N($R_{XIV-14}$), C(S)N($R_{XIV-14}$), ($R_{XIV-14}$)NC(O), ($R_{XIV-14}$)NC(S), S, S(O), S(O)$_2$, S(O)$_2$N($R_{XIV-14}$), ($R_{XIV-14}$)NS(O)$_2$, and N($R_{XIV-14}$) with the proviso that $R_{XIV-14}$ is selected from other than halo and cyano;

$Z_{XIV}$ is independently selected from a group consisting of a covalent single bond, $(C(R_{XIV-15})_2)_{qXIV-2}$ wherein $_{qXIV-2}$ is an integer selected from 1 and 2, $(CH(R_{XIV-15}))_{jXIV}$—W—$(CH(R_{XIV-15}))_{kXIV}$ wherein $_{jXIV}$ and $_{kXIV}$ are integers independently selected from 0 and 1 with the proviso that, when $Z_{XIV}$ is a covalent single bond, an $R_{XIV-15}$ substituent is not attached to $Z_{XIV}$;

$R_{XIV-15}$ is independently selected, when $Z_{XIV}$ is (C($R_{XIV-15}$)$_2$)$_{qXIV}$ wherein $_{qXIV}$ is an integer selected from 1 and 2, from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_{XIV-9}$ and $R_{XIV-13}$ to form a heterocyclyl having from 5 through 8 contiguous members;

$R_{XIV-15}$ and $R_{XIV-15}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-15}$ and $R_{XIV-15}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$R_{XIV-15}$ is independently selected, when $Z_{XIV}$ is (CH($R_{XIV-15}$))$_{jXIV}$—W—(CH($R_{XIV-15}$))$_{kXIV}$ wherein $_{jXIV}$ and $_{kXIV}$ are integers independently selected from 0 and 1, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, halocycloalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_{XIV-9}$ and $R_{XIV-13}$ to form a heterocyclyl ring having from 5 through 8 contiguous members;

$R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsufonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl; haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that there are one to five non-hydrido ring substituents $R_{XIV\text{-}4}$, $R_{XIV\text{-}5}$, $R_{XIV\text{-}6}$, $R_{XIV\text{-}7}$, and $R_{XIV\text{-}8}$ present, that there are one to five non-hydrido ring substituents $R_{XIV\text{-}9}$, $R_{XIV\text{-}10}$, $R_{XIV\text{-}11}$, $R_{XIV\text{-}12}$, and $R_{XIV\text{-}13}$ present, and $R_{XIV\text{-}4}$, $R_{XIV\text{-}5}$, $R_{XIV\text{-}6}$, $R_{XIV\text{-}7}$, $R_{XIV\text{-}8}$, $R_{XIV\text{-}9}$, $R_{XIV\text{-}10}$, $R_{XIV\text{-}11}$, $R_{XIV\text{-}12}$, and $R_{XIV\text{-}13}$ are each independently selected to maintain the tetravalent nature of carbon, trivalent nature of nitrogen, the divalent nature of sulfur, and the divalent nature of oxygen;

$R_{XIV\text{-}4}$ and $R_{XIV\text{-}5}$, $R_{XIV\text{-}5}$ and $R_{XIV\text{-}6}$, $R_{XIV\text{-}6}$ and $R_{XIV\text{-}7}$, $R_{XIV\text{-}7}$ and $R_{XIV\text{-}8}$, $R_{XIV\text{-}8}$ and $R_{XIV\text{-}9}$, $R_{XIV\text{-}9}$ and $R_{XIV\text{-}10}$, $R_{XIV\text{-}10}$ and $R_{XIV\text{-}11}$, $R_{XIV\text{-}11}$ and $R_{XIV\text{-}12}$, and $R_{XIV\text{-}12}$ and $R_{XIV\text{-}13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XIV\text{-}4}$ and $R_{XIV\text{-}5}$, $R_{XIV\text{-}5}$ and $R_{XIV\text{-}6}$, $R_{XIV\text{-}6}$ and $R_{XIV\text{-}7}$, and $R_{XIV\text{-}7}$ and $R_{XIV\text{-}8}$ are used at the same time and that no more than one of the group consisting of spacer pairs $R_{XIV\text{-}9}$ and $R_{XIV\text{-}10}$, $R_{XIV\text{-}10}$ and $R_{XIV\text{-}11}$, $R_{XIV\text{-}11}$ and $R_{XIV\text{-}12}$, and $R_{XIV\text{-}12}$ and $R_{XIV\text{-}13}$ are used at the same time;

$R_{XIV\text{-}4}$ and $R_{XIV\text{-}9}$, $R_{XIV\text{-}4}$ and $R_{XIV\text{-}13}$, $R_{XIV\text{-}8}$ and $R_{XIV\text{-}9}$, and $R_{XIV\text{-}8}$ and $R_{XIV\text{-}13}$ are independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XIV\text{-}4}$ and $R_{XIV\text{-}9}$, $R_{XIV\text{-}4}$ and $R_{XIV\text{-}13}$, $R_{XIV\text{-}8}$ and $R_{XIV\text{-}9}$, and $R_{XIV\text{-}8}$ and $R_{XIV\text{-}13}$ is used at the same time.

Compounds of Formula XIV and their methods of manufacture are disclosed in PCT Publication No. WO 00/18721, which is incorporated herein by reference in its entirety for all purposes.

In a preferred embodiment, the CETP inhibitor is selected from the following compounds of Formula XIV:

3-[[3-(3-trifluoromethoxyphenoxy)phenyl][[3-(1,1,2,2-tetrafluoroethoxy)-phenyl]methyl]amino]-1,1,1-trifluoro-2-propanol;

3-[[3-(3-isopropylphenoxy)phenyl][[3-(1,1,2,2-tetrafluoroethoxy)phenyl]-methyl]amino]-1,1,1-trifluoro-2-propanol;

3-[[3-(3-cyclopropylphenoxy)phenyl][[3-(1,1,2,2-tetrafluoroethoxy)phenyl]-methyl]amino]-1,1,1-trifluoro-2-propanol;

3-[[3-(3-(2-furyl)phenoxy)phenyl][[3-(1,1,2,2-tetrafluoroethoxy)phenyl]-methyl]amino]1,1,1-trifluoro-2-propanol;

3-[[3-(2,3-dichlorophenoxy)phenyl][[3-(1,1,2,2-tetrafluoroethoxy)phenyl]-methyl]amino]-1,1,1-trifluoro-2-propanol;

3-[[3-(4-fluorophenoxy)phenyl][[3-(1,1,2,2-tetrafluoroethoxy)phenyl]-methyl]amino]-1,1,1-trifluoro-2-propanol;

3-[[3-(4-methlylphenoxy)phenyl][[3-(1,1,2,2-tetrafluoroethoxy)phenyl]-methyl]amino]-1,1,1-trifluoro-2-propanol;

3-[[3-(2-fluoro-5-bromophenoxy)phenyl][[3-(1,1,2,2-tetrafluoroethoxy)phenyl]-methyl]amino]-1,1,1-trifluoro-2-propanol;

3-[[3-(4-chloro-3-ethylphenoxy)phenyl][[3-(1,1,2,2-tetrafluoroethoxy)phenyl]-methyl]amino]-1,1,1-trifluoro-2-propanol;

3-[[3-[3-(1,1,2,2-tetrafluoroethoxy)phenoxy]phenyl][[3-(1,1,2,2-tetrafluoroethoxy)phenyl]methyl]amino]-1,1,1-trifluoro-2-propanol;

3-[[3-[3-(pentafluoroethyl)phenoxy]phenyl][[3-(1,1,2,2-tetrafluoroethoxy)-phenyl]methyl]amino]-1,1,1-trifluoro-2-propanol;

3-[[3-(3,5-dimethylphenoxy)phenyl][[3-(1,1,2,2-tetrafluoroethoxy)phenyl]-methyl]amino]-1,1,1-trifluoro-2-propanol;

3-[[3-(3-ethylphenoxy)phenyl][[3-(1,1,2,2-tetrafluoroethoxy)phenyl]-methyl]amino]-1,1,1-trifluoro-2-propanol;

3-[[3-(3-t-butylphenoxy)phenyl][[3-(1,1,2,2-tetrafluoroethoxy)phenyl]-methyl]amino]1,1,1-trifluoro-2-propanol;

3-[[3-(3-methylphenoxy)phenyl][[3-(1,1,2,2-tetrafluoroethoxy)phenyl]-methyl]amino]-1,1,1-trifluoro-2-propanol;

3-[[3-(5,6,7,8-tetrahydro-2-naphthoxy)phenyl][[3-(1,1,2,2-tetrafluoroethoxy)phenyl]methyl]amino]-1,1,1-trifluoro-2-propanol;

3-[[3-(phenoxy)phenyl][[3-(1,1,2,2-tetrafluoroethoxy)phenyl]methyl]amino]-1,1,1-trifluoro-2-propanol;

3-[[3-[3-(N,N-dimethylamino)phenoxy]phenyl][[3-(1,1,2,2-tetrafluoroethoxy)phenyl]methyl]amino]-1,1,1-trifluoro-2-propanol;

3-[[[3-(1,1,2,2-tetrafluoroethoxy)phenyl]methyl][3-[[3-(trifluoromethoxy)phenyl]methoxy]phenyl]amino]-1,1,1-trifluoro-2-propanol;

3-[[[3-(1,1,2,2-tetrafluoroethoxy)phenyl]methyl][3-[[3-(trifluoromethyl)phenyl]methoxy]phenyl]amino]-1,1,1-trifluoro-2-propanol;

3-[[[3-(1,1,2,2-tetrafluoroethoxy)phenyl]methyl][3-[[3,5-dimethylphenyl]-methoxy]phenyl]amino]-1,1,1-trifluoro-2-propanol;

3-[[[3-(1,1,2,2-tetrafluoroethoxy)phenyl]methyl][3-[[3-(trifluoromethylthio)phenyl]methoxy]phenyl]amino]-1,1,1-trifluoro-2-propanol;

3-[[[3-(1,1,2,2-tetrafluoroethoxy)phenyl]methyl][3-[[3,5-difluorophenyl]-methoxy]phenyl]amino]-1,1,1-trifluoro-2-propanol;

3-[[[3-(1,1,2,2-tetrafluoroethoxy)phenyl]methyl][3-[cyclohexylmethoxy]-phenyl]amino]-1,1,1-trifluoro-2-propanol;

3-[[3-(2-difluoromethoxy-4-pyridyloxy)phenyl][[3-(1,1,2,2-tetrafluoroethoxy)phenyl]methyl]amino]-1,1,1-trifluoro-2-propanol;

3-[[3-(2-trifluoromethyl-4-pyridyloxy)phenyl][[3-(1,1,2,2-tetrafluoroethoxy)phenyl]methyl]amino]-1,1,1-trifluoro-2-propanol;

3-[[3-(3-difluoromethoxyphenoxy)phenyl][[3-(1,1,2,2-tetrafluoroethoxy)phenyl]methyl]amino]-1,1,1-trifluoro-2-propanol;

3-[[[3-(3-trifluoromethylthio)phenoxy]phenyl][[3-(1,1,2,2-tetrafluoroethoxy)phenyl]methyl]amino]-1,1,1-trifluoro-2-propanol;

3-[[3-(4-chloro-3-trifluoromethylphenoxy)phenyl][[3-(1,1,2,2-tetrafluoroethoxy)-phenyl]methyl]amino]-1,1,1-trifluoro-2-propanol;
3-[[3-(3-trifluoromethoxyphenoxy)phenyl][[3-(pentafluoroethymethyl]amino]-1,1,1-trifluoro-2-propanol;
3-[[3-(3-isopropylphenoxy)phenyl][[3-(pentafluoroethyl)phenyl]methyl]-amino]-1,1,1-trifluoro-2-propanol;
3-[[3-(3-cyclopropylphenoxy)phenyl][[3-(pentafluoroethyl)phenyl]methyl]-amino]-1,1,1-trifluoro-2-propanol;
3-[[3-(3-(2-furyl)phenoxy)phenyl][[3-(pentafluoroethyl)phenyl]methyl]amino]-1,1,1-trifluoro-2-propanol;
3-[[3-(2,3-dichlorophenoxy)phenyl][[3-(pentafluoroethyl)phenyl]methyl]-amino]-1,1,1-trifluoro-2-propanol;
3-[[3-(4-fluorophenoxy)phenyl][[3-(pentafluoroethyl)phenyl]methyl]amino]-1,1,1-trifluoro-2-propanol;
3-[[3-(4-methylphenoxy)phenyl][[3-(pentafluoroethyl)phenyl]methyl]amino]-1,1,1-trifluoro-2-propanol;
3-[[3-(2-fluoro-5-bromophenoxy)phenyl][[3-(pentafluoroethyl)phenyl]methyl-amino]-1,1,1-trifluoro-2-propanol;
3-[[3-(4-chloro-3-ethylphenoxy)phenyl][[3-(pentafluoroethyl)phenyl]methyl]-amino]-1,1,1-trifluoro-2-propanol;
3-[[3-[3-(1,1,2,2-tetrafluoroethoxy)phenoxy]phenyl][[3-(pentafluoroethyl)-phenyl]methyl]amino]-1,1,1-trifluoro-2-propanol;
3-[[3-[3-(pentafluoroethyl)phenoxy]phenyl][[3-(pentafluoroethyl)phenyl]-methyl]amino]-1,1,1-trifluoro-2-propanol;
3-[[3-(3,5-dimethylphenoxy)phenyl][[3-(pentafluoroethyl)phenyl]methyl]-amino]-1,1,1-trifluoro-2-propanol;
3-[[3-(3-ethylphenoxy)phenyl][[3-(pentafluoroethyl)phenyl]methyl]amino]-1,1,1-trifluoro-2-propanol;
3-[[3-(3-t-butylphenoxy)phenyl][[3-(pentafluoroethyl)phenyl]methyl]amino]-1,1,1-trifluoro-2-propanol;
3-[[3-(3-methylphenoxy)phenyl][[3-pentafluoroethyl)phenyl]methyl]amino]-1,1,1-trifluoro-2-propanol;
3-[[3-(5,6,7,8-tetrahydro-2-naphthoxy)phenyl][[3-(pentafluoroethyl)phenyl]-methyl]amino]-1,1,1-trifluoro-2-propanol;
3-[[3-(phenoxy)phenyl][[3-(pentafluoroethyl)phenyl]methyl]amino]-1,1,1-trifluoro-2-propanol;
3-[[3-[3-(N,N-dimethylamino)phenoxy]phenyl][[3-(pentafluoroethyl)phenyl]-methyl]amino]-1,1,1-trifluoro-2-propanol;
3-[[[3-(pentafluoroethyl)phenyl]methyl][3-[[3-(trifluoromethoxy)phenyl]-methoxy]phenyl]amino]-1,1,1-trifluoro-2-propanol;
3-[[[3-(pentafluoroethyl)phenyl]methyl][3-[[3-(trifluoromethyl)phenyl]-methoxy]phenyl]amino]-1,1,1-trifluoro-2-propanol;
3-[[[3-(pentafluoroethyl)phenyl]methyl][3-[[3,5-dimethylphenyl]methoxy]-phenyl]amino]-1,1,1-trifluoro-2-propanol;
3-[[[3-(pentafluoroethyl)phenyl]methyl][3-[[3-(trifluoromethylthio)phenyl]-methoxy]phenyl]amino]-1,1,1-trifluoro-2-propanol;
3-[[[3-(pentafluoroethyl)phenyl]methyl][3-[[3,5-difluorophenyl]methoxy]-phenyl]amino]-1,1,1-trifluoro-2-propanol;
3-[[[3-(pentafluoroethyl)phenyl]methyl][3-[cyclohexylmethoxy]phenyl]-amino]-1,1,1-trifluoro-2-propanol;
3-[[3-(2-difuoromethoxy-4-pyridyloxy)phenyl][[3-(pentafluoroethyl)phenyl]-methyl]amino]-1,1,1-trifluoro-2-propanol;
3-[[3-(2-trifluoromethyl-4-pyridyloxy)phenyl][[3-(pentafluoroethyl)phenyl]-methyl]amino]-1,1,1-trifluoro-2-propanol;
3-[[3-(3-difluoromethoxyphenoxy)phenyl][[3-(pentafluoroethyl)phenyl]-methyl]amino]-1,1,1-trifluoro-2-propanol;
3-[[[3-(3-trifluoromethylthio)phenoxy]phenyl][[3-(pentafluoroethyl)phenyl]-methyl]amino]-1,1,1-trifluoro-2-propanol;
3-[[3-(4-chloro-3-trifluoromethylphenoxy)phenyl][[3-(pentafluoroethyl)phenyl]methyl]amino]-1,1,1-trifluoro-2-propanol;
3-[[3-(3-trifluoromethoxyphenoxy)phenyl][[3-(heptafluoropropyl)phenyl]-methyl]amino]-1,1,1-trifluoro-2-propanol;
3-[[3-(3-isopropylphenoxy)phenyl][[3-(heptafluoropropyl)phenyl]methyl]amino]-1,1,1-trifluoro-2-propanol;
3-[[3-(3-cyclopropylphenoxy)phenyl][[3-(heptafluoropropyl)phenyl]methyl]amino]-1,1,1-trifluoro-2-propanol;
3-[[3-(3-(2-furyl)phenoxy)phenyl][[3-(heptafluoropropyl)phenyl]methyl]amino]-1,1,1-trifluoro-2-propanol;
3-[[3-(2,3-dichlorophenoxy)phenyl][[3-(heptafluoropropyl)phenyl]methyl]amino]-1,1,1-trifluoro-2-propanol;
3-[[3-(4-fluorophenoxy)phenyl][[3-(heptafluoropropyl)phenyl]methyl]amino]1,1,1-trifluoro-2-propanol;
3-[[3-(4-methylphenoxy)phenyl][[3-(heptafluoropropyl)phenyl]methyl]amino]-1,1,1-trifluoro-2-propanol;
3-[[3-(2-fluoro-5-bromophenoxy)phenyl][[3-(heptafluoropropyl)phenyl]methyl]amino]-1,1,1-trifluoro-2-propanol;
3-[[3-(4-chloro-3-ethylphenoxy)phenyl][[3-(heptafluoropropyl)phenyl]methyl]-amino]-1,1,1-trifluoro-2-propanol;
3-[[3-[3-(1,1,2,2-tetrafluoroethoxy)phenoxy]phenyl][[3-(heptafluoropropyl)-phenyl]methyl]amino]-1,1,1-trifluoro-2-propanol;
3-[[3-[3-(pentafluoroethyl)phenoxy]phenyl][[3-(heptafluoropropyl)phenyl]-methyl]amino]-1,1,1-trifluoro-2-propanol;
3-[[3-(3,5-dimethylphenoxy)phenyl][[3-(heptafluoropropyl)phenyl]methyl]amino]-1,1,1-trifluoro-2-propanol;
3-[[3-(3-ethylphenoxy)phenyl][[3-(heptafluoropropyl)phenyl]methyl]amino]-1,1,1-trifluoro-2-propanol;
3-[[3-(3-t-butylphenoxy)phenyl][[3-(heptafluoropropyl)phenyl]methyl]amino]-1,1,1-trifluoro-2-propanol;
3-[[3-(3-methylphenoxy)phenyl][[3-(heptafluoropropyl)phenyl]methyl]amino]-1,1,1-trifluoro-2-propanol;
3-[[3-(5,6,7,8-tetrahydro-2-naphthoxy)phenyl][[3-(heptafluoropropyl)phenyl]-methyl]amino]-1,1,1-trifluoro-2-propanol;
3-[[3-(phenoxy)phenyl][[3-(heptafluoropropyl)phenyl]methyl]amino]-1,1,1-trifluoro-2-propanol;
3-[[3-[3-(N,N-dimethylamino)phenoxy]phenyl][[3-(heptafluoropropyl)phenyl]-methyl]amino]-1,1,1-trifluoro-2-propanol;
3-[[[3-(heptafluoropropyl)phenyl]methyl][3-[[3-(trifluoromethoxy)phenyl]-methoxy]phenyl]amino]-1,1,1-trifluoro-2-propanol;
3-[[[3-(heptafluoropropyl)phenyl]methyl][3-[[3-(trifluoromethyl)phenyl]-methoxy]phenyl]amino]-1,1,1-trifluoro-2-propanol;
3-[[[3-(heptafluoropropyl)phenyl]methyl][3-[[3,5-dimethylphenyl]methoxy]-phenyl]amino]-1,1,1-trifluoro-2-propanol;
3-[[[3-(heptafluoropropyl)phenyl]methyl][3-[[3-(trifluoromethylthio)phenyl]-methoxy]phenyl]amino]-1,1,1-trifluoro-2-propanol;
3-[[[3-(heptafluoropropyl)phenyl]methyl][3-[[3,5-difluorophenyl]methoxy]-phenyl]amino]-1,1,1-trifluoro-2-propanol;
3-[[[3-(heptafluoropropyl)phenyl]methyl][3-[cyclohexylmethoxy]phenyl]-amino]-1,1,1-trifluoro-2-propanol;

3-[[3-(2-difluoromethoxy-4-pyridyloxy)phenyl][[3-(heptafluoropropyl)phenyl]-methyl]amino]-1,1,1-trifluoro-2-propanol;

3-[[3-(2-trifluoromethyl-4-pyridyloxy)phenyl][[3-(heptafluoropropyl)phenyl]-methyl]amino]-1,1,1-trifluoro-2-propanol;

3-[[3-(3-difluoromethoxyphenoxy)phenyl][[3-(heptafluoropropyl)phenyl]-methyl]amino]-1,1,1-trifluoro-2-propanol;

3-[[[3-(3-trifluoromethylthio)phenoxy]phenyl][[3-(heptafluoropropyl)phenyl]-methyl]amino]-1,1,1-trifluoro-2-propanol;

3-[[3-(4-chloro-3-trifluoromethylphenoxy)phenyl][[3-(heptafluoropropyl)phenyl]-methyl]amino]-1,1,1-trifluoro-2-propanol;

3-[[3-(3-trifluoromethoxyphenoxy)phenyl][[2-fluoro-5-(trifluoromethyl)phenyl]-methyl]amino]-1,1,1-trifluoro-2-propanol;

3-[[3-(3-isopropylphenoxy)phenyl][[2-fluoro-5-(trifluoromethyl)phenyl]-methyl]amino]-1,1,1-trifluoro-2-propanol;

3-[[3-(3-cyclopropylphenoxy)phenyl][[2-fluoro-5-(trifluoromethyl)phenyl]-methyl]amino]-1,1,1-trifluoro-2-propanol;

3-[[3-(3-(2-furyl)phenoxy)phenyl][[2-fluoro-5-(trifluoromethyl)phenyl]-methyl]amino]-1,1,1-trifluoro-2-propanol;

3-[[3-(2,3-dichlorophenoxy)phenyl][[2-fluoro-5-(trifluoromethyl)phenyl]-methyl]amino]-1,1,1-trifluoro-2-propanol;

3-[[3-(4-fluorophenoxy)phenyl][[2-fluoro-5-(trifluoromethyl)phenyl]-methyl]amino]-1,1,1-trifluoro-2-propanol;

3-[[3-(4-methylphenoxy)phenyl][[2-fluoro-5-(trifluoromethyl)phenyl]-methyl]amino]-1,1,1-trifluoro-2-propanol;

3-[[3-(2-fluoro-5-bromophenoxy)phenyl][[2-fluoro-5-(trifluoromethyl)phenyl]methyl]amino]-1,1,1-trifluoro-2-propanol;

3-[[3-(4-chloro-3-ethylphenoxy)phenyl][[2-fluoro-5-(trifluoromethyl)phenyl]methyl]amino]-1,1,1-trifluoro-2-propanol;

3-[[3-[3-(1,1,2,2-tetrafluoroethoxy)phenoxy]phenyl][[2-fluoro-5-(trifluoromethyl)phenyl]methyl]amino]-1,1,1-trifluoro-2-propanol;

3-[[3-[3-(pentafluoroethyl)phenoxy]phenyl][[2-fluoro-5-(trifluoromethyl)phenyl]-methyl]amino]-1,1,1-trifluoro-2-propanol;

3-[[3-(3,5-dimethylphenoxy)phenyl][[2-fluoro-5-(trifluoromethyl)phenyl]-methyl]amino]-1,1,1-trifluoro-2-propanol;

3-[[3-(3-ethylphenoxy)phenyl][[2-fluoro-5-(trifluoromethyl)phenyl]methyl]-amino]-1,1,1-trifluoro-2-propanol;

3-[[3-(3-t-butylphenoxy)phenyl][[2-fluoro-5-(trifluoromethyl)phenyl]methyl]-amino]-1,1,1-trifluoro-2-propanol;

3-[[3-(3-methylphenoxy)phenyl][[2-fluoro-5-(trifluoromethyl)phenyl]methyl]-amino]-1,1,1-trifluoro-2-propanol;

3-[[3-(5,6,7,8-tetrahydro-2-naphthoxy)phenyl][[2-fluoro-5-(trifluoromethyl)-phenyl]methyl]amino]-1,1,1-trifluoro-2-propanol;

3-[[3-(phenoxy)phenyl][[2-fluoro-5-(trifluoromethyl)phenyl]methyl]amino]-1,1,1-trifluoro-2-propanol;

3-[[3-[3-(N,N-dimethylamino)phenoxy]phenyl][[2-fluoro-5-(trifluoromethyl)-phenyl]methyl]amino]-1,1,1-trifluoro-2-propanol;

3-[[[2-fluoro-5-(trifluoromethyl)phenyl]methyl][3-[[3-(trifluoromethoxy)phenyl]methoxy]phenyl]amino]-1,1,1-trifluoro-2-propanol;

3-[[[2-fluoro-5-(trifluoromethyl)phenyl]methyl][3-[[3-(trifluoromethyl)phenyl]methoxy]phenyl]amino]-1,1,1-trifluoro-2-propanol;

3-[[[2-fluoro-5-(trifluoromethyl)phenyl]methyl][3-[[3,5-dimethylphenyl]-methoxy]phenyl]amino]-1,1,1-trifluoro-2-propanol;

3-[[[2-fluoro-5-(trifluoromethyl)phenyl]methyl][3-[[3-(trifluoromethylthio)-phenyl]methoxy]phenyl]amino]-1,1,1-trifluoro-2-propanol;

3-[[[2-fluoro-5-(trifluoromethyl)phenyl]methyl][3-[[3,5-difluorophenyl]-methoxy]phenyl]amino]-1,1,1-trifluoro-2-propanol;

3-[[[2-fluoro-5-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-5-(trifluoromethyl)-phenyl]methyl]amino]-1,1,1-trifluoro-2-propanol;

3-[[3-(2-trifluoromethyl-4-pyridyloxy)phenyl][[2-fluoro-5-(trifluoromethyl)-phenyl]methyl]amino]-1,1,1-trifluoro-2-propanol;

3-[[3-(3-difluoromethoxyphenoxy)phenyl][[2-fluoro-5-(trifluoromethyl)phenyl]methyl]amino]-1,1,1-trifluoro-2-propanol;

3-[[[3-(3-trifluoromethylthio)phenoxy]phenyl][[2-fluoro-5-(trifluoromethyl)phenyl]methyl]amino]-1,1,1-trifluoro-2-propanol;

3-[[3-(4-chloro-3-trifluoromethylphenoxy)phenyl][[2-fluoro-5-(trifluoromethyl)phenyl]methyl]amino]-1,1,1-trifluoro-2-propanol;

3-[[3-(3-trifluoromethoxyphenoxy)phenyl][[2-fluoro-4-(trifluoromethyl)phenyl]methyl]amino]-1,1,1-trifluoro-2-propanol;

3-[[3-(3-isopropylphenoxy)phenyl][[2-fluoro-4-(trifluoromethyl)phenyl]-methyl]amino]-1,1,1-trifluoro-2-propanol;

3-[[3-(3-cyclopropylphenoxy)phenyl][[2-fluoro-4-(trifluoromethyl)phenyl]-methyl]amino]-1,1,1-trifluoro-2-propanol;

3-[[3-(3-(2-furyl)phenoxy)phenyl][[2-fluoro-4-(trifluoromethyl)phenyl]-methyl]amino]-1,1,1-trifluoro-2-propanol;

3-[[3-(2,3-dichlorophenoxy)phenyl][[2-fluoro-4-(trifluoromethyl)phenyl]-methyl]amino]-1,1,1-trifluoro-2-propanol;

3-[[3-(4-fluorophenoxy)phenyl][[2-fluoro-4-(trifluoromethyl)phenyl]-methyl]amino]-1,1,1-trifluoro-2-propanol;

3-[[3-(4-methylphenoxy)phenyl][[2-fluoro-4-(trifluoromethyl)phenyl]-methyl]amino]-1,1,1-trifluoro-2-propanol;

3-[[3-(2-fluoro-5-bromophenoxy)phenyl][[2-fluoro-4-(trifluoromethyl)phenyl]methyl]amino]-1,1,1-trifluoro-2-propanol;

3-[[3-(4-chloro-3-ethylphenoxy)phenyl][[2-fluoro-4-(trifluoromethyl)phenyl]methyl]amino]-1,1,1-trifluoro-2-propanol;

3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;

3-[[3-[3-(pentafluoroethyl)phenoxy]phenyl][[2-fluoro-4-(trifluoromethyl)phenyl]methyl]amino]-1,1,1-trifluoro-2-propanol;

3-[[3-(3,5-dimethylphenoxy)phenyl][[2-fluoro-4-(trifluoromethyl)phenyl]-methyl]amino]-1,1,1-trifluoro-2-propanol;

3-[[3-(3-ethylphenoxy)phenyl][[2-fluoro-4-(trifluoromethyl)phenyl]methyl]-amino]-1,1,1-trifluoro-2-propanol;

3-[[3-(3-t-butylphenoxy)phenyl][[2-fluoro-4-(trifluoromethyl)phenyl]methyl]-amino]-1,1,1-trifluoro-2-propanol;

3-[[3-(3-methylphenoxy)phenyl][[2-fluoro-4-(trifluoromethyl)phenyl]methyl]-amino]-1,1,1-trifluoro-2-propanol;

3-[[3-(5,6,7,8-tetrahydro-2-naphthoxy)phenyl][[2-fluoro-4-(trifluoromethyl)phenyl]methyl]amino]-1,1,1-trifluoro-2-propanol;

3-[[3-(phenoxy)phenyl][[2-fluoro-4-(trifluoromethyl)phenyl]methyl]amino]-1,1,1-trifluoro-2-propanol;

3-[[3-[3-(N,N-dimethylamino)phenoxy]phenyl][[2-fluoro-4-(trifluoromethyl)-phenyl]methyl]amino]-1,1,1-trifluoro-2-propanol;

3-[[[2-fluoro-4-(trifluoromethyl)phenyl]methyl][3-[[3-(trifluoromethoxy)phenyl]methoxy]phenyl]amino]-1,1,1-trifluoro-2-propanol;

3-[[[2-fluoro-4-(trifluoromethyl)phenyl]methyl][3-[[3-(trifluoromethyl)phenyl]methoxy]phenyl]amino]-1,1,1-trifluoro-2-propanol;

3-[[[2-fluoro-4-(trifluoromethyl)phenyl]methyl][3-[[3,5-dimethylphenyl]-methoxy]phenyl]amino]-1,1,1-trifluoro-2-propanol;

3-[[[2-fluoro-4-(trifluoromethyl)phenyl]methyl][3-[[3-(trifluoromethylthio)-phenyl]methoxy]phenyl]amino]-1,1,1-trifluoro-2-propanol;

3-[[[2-fluoro-4-(trifluoromethyl)phenyl]methyl][3-[[3,5-difluorophenyl]-methoxy]phenyl]amino]-1,1,1-trifluoro-2-propanol;

3-[[[2-fluoro-4-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-4-(trifluoromethyl)-phenyl]methyl]amino]-1,1,1-trifluoro-2-propanol;

3-[[3-(2-trifluoromethyl-4-pyridyloxy)phenyl][[2-fluoro-4-(trifluoromethyl)-phenyl]methyl]amino]-1,1,1-trifluoro-2-propanol;

3-[[3-(3-difluoromethoxyphenoxy)phenyl][[2-fluoro-4-(trifluoromethyl)phenyl]methyl]amino]-1,1,1-trifluoro-2-propanol;

3-[[[3-(3-trifluoromethylthio)phenoxy]phenyl][[2-fluoro-4-(trifluoromethyl)-phenyl]methyl]amino]-1,1,1-trifluoro-2-propanol; and 3-[[3-(4-chloro-3-trifluoromethylphenoxy)phenyl][[2-fluoro-4-(trifluoromethyl)phenyl]methyl]amino]-1,1,1-trifluoro-2-propanol.

Another class of CETP inhibitors that finds utility with the present invention consists of substituted N-Aliphatic-N-Aromatic tertiary-Heteroalkylamines having the Formula XV

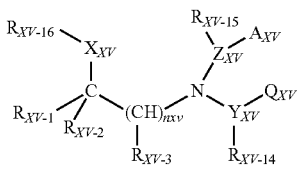

Formula XV and pharmaceutically acceptable forms thereof, wherein:

$n_{XV}$ is an integer selected from 1 through 2;

$A_{XV}$ and $Q_{XV}$ are independently selected from the group consisting of —CH$_2$(CR$_{XV-37}$R$_{XV-38}$)$_{vXV}$—(CR$_{XV-33}$R$_{XV-34}$)$_{uXV}$-T$_{XV}$-(CR$_{XV-35}$R$_{XV-36}$)$_{wXV}$-H,

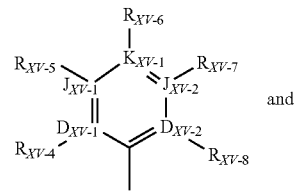

AQ-1

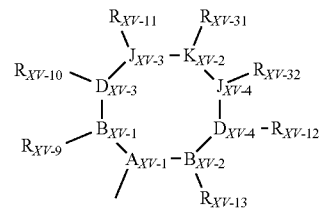

AQ-2 with the provisos that one of $A_{XV}$ and $Q_{XV}$ must be AQ-1 and that one of $A_{XV}$ and $Q_{XV}$ must be selected from the group consisting of AQ-2 and —CH$_2$(CR$_{XV-37}$R$_{XV-38}$)$_{vXV}$—(CR$_{XV-33}$R$_{XV-34}$)$_{uXV}$-T$_{XV}$-(CR$_{XV-35}$R$_{XV-36}$)$_{wXV}$—H;

$T_{XV}$ is selected from the group consisting of a single covalent bond, O, S, S(O), S(O)$_2$, C(R$_{XV-33}$)=C(R$_{XV-35}$), and C≡C;

$_{vXV}$ is an integer selected from 0 through 1 with the proviso that $_{vXV}$ is 1 when any one of R$_{XV-33}$, R$_{XV-34}$, R$_{XV-35}$, and R$_{XV-36}$ is aryl or heteroaryl;

$_{uXV}$ and $_{wXV}$ are integers independently selected from 0 through 6;

$A_{XV-1}$ is C(R$_{XV-30}$);

$D_{XV-1}$, $D_{XV-2}$, $J_{XV-1}$, $J_{XV-2}$, and $K_{XV-1}$, are independently selected from the group consisting of C, N, O, S and a covalent bond with the provisos that no more than one of $D_{XV-1}$, $D_{XV-2}$, $J_{XV-1}$, $J_{XV-2}$, and $K_{XV-1}$ is a covalent bond, no more than one of $D_{XV-1}$, $D_{XV-2}$, $J_{XV-1}$, $J_{XV-2}$, and $K_{XV-1}$, is O, no more than one of $D_{XV-1}$, $D_{XV-2}$, $J_{XV-1}$, $J_{XV-2}$, and $K_{XV-1}$ is S, one of $D_{XV-1}$, $D_{XV-2}$, $J_{XV-1}$, $J_{XV-2}$, and $K_{XV-1}$ must be a covalent bond when two of $D_{XV-1}$, $D_{XV-2}$, $J_{XV-1}$, $J_{XV-2}$, and $K_{XV-1}$ are O and S, and no more than four of $D_{XV-1}$, $D_{XV-2}$, $J_{XV-1}$, $J_{XV-2}$, and $K_{XV-1}$ are N;

$B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C, C(R$_{XV-30}$), N, O, S and a covalent bond with the provisos that no more than 5 of $B_{XV-1}$, $B_{XV-2}$, $D_{XV-3}$, $D_{XV-4}$, $J_{XV-3}$, $J_{XV-4}$, and $K_{XV-2}$ are a covalent bond, no more than two of $B_{XV-1}$, $B_{XV-2}$, $D_{XV-3}$, $D_{XV-4}$, $J_{XV-3}$, $J_{XV-4}$, and $K_{XV-2}$ are O, no more than two of $B_{XV-1}$, $B_{XV-2}$, $D_{XV-3}$, $D_{XV-4}$, $J_{XV-3}$, $J_{XV-4}$, and $K_{XV-2}$ are S, no more than two of $B_{XV-1}$, $B_{XV-2}$, $D_{XV-3}$, $D_{XV-4}$, $J_{XV-3}$, $J_{XV-4}$, and $K_{XV-2}$ are simultaneously O and S, and no more than two of $B_{XV-1}$, $B_{XV-2}$, $D_{XV-3}$, $D_{XV-4}$, $J_{XV-3}$, $J_{XV-4}$, and $K_{XV-2}$ are N;

$B_{XV-1}$ and $D_{XV-3}$, $D_{XV-3}$ and $J_{XV-3}$, $J_{XV-3}$ and $K_{XV-2}$, $K_{XV-2}$ and $J_{XV-4}$, $J_{XV-4}$ and $D_{XV-4}$, and $D_{XV-4}$ and $B_{XV-2}$ are independently selected to form an in-ring spacer pair wherein said spacer pair is selected from the group consisting of C(R$_{XV-33}$)=C(R$_{XV-35}$) and N=N with the provisos that AQ-2 must be a ring of at least five contiguous members, that no more than two of the group of said spacer pairs are simultaneously C(R$_{XV-33}$)=C(R$_{XV-35}$) and that no more than one of the group of said spacer pairs can be N=N unless the other spacer pairs are other than C(R$_{XV-33}$)=C(R$_{XV-35}$), O, N, and S;

$R_{XV-1}$ is selected from the group consisting of haloalkyl and haloalkoxymethyl;

$R_{XV-2}$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl and heteroaryl;

$R_{XV-3}$ is selected from the group consisting of hydrido, aryl, alkyl, alkenyl, haloalkyl, and haloalkoxyalkyl;

$Y_{XV}$ is selected from the group consisting of a covalent single bond, $(CH_2)_q$ wherein q is an integer selected from 1 through 2 and $(CH_2)_j$—O—$(CH_2)_k$ wherein j and k are integers independently selected from 0 through 1;

$Z_{XV}$ is selected from the group consisting of covalent single bond, $(CH_2)_q$ wherein q is an integer selected from 1 through 2, and $(CH_2)_j$—O—$(CH_2)_k$ wherein j and k are integers independently selected from 0 through 1;

$R_{XV-4}$, $R_{XV-8}$, $R_{XV-9}$ and $R_{XV-13}$ are independently selected from the group consisting of hydrido, halo, haloalkyl, and alkyl;

$R_{XV-30}$ is selected from the group consisting of hydrido, alkoxy, alkoxyalkyl, halo, haloalkyl, alkylamino, alkylthio, alkylthioalkyl, alkyl, alkenyl, haloalkoxy, and haloalkoxyalkyl with the proviso that $R_{XV-30}$ is selected to maintain the tetravalent nature of carbon, trivalent nature of nitrogen, the divalent nature of sulfur, and the divalent nature of oxygen;

$R_{XV-30}$, when bonded to $A_{XV-1}$, is taken together to form an intra-ring linear spacer connecting the $A_{XV-1}$-carbon at the point of attachment of $R_{XV-30}$ to the point of bonding of a group selected from the group consisting of $R_{XV-10}$, $R_{XV-11}$, $R_{XV-12}$, $R_{XV-31}$, and $R_{XV-32}$ wherein said intra-ring linear spacer is selected from the group consisting of a covalent single bond and a spacer moiety having from 1 through 6 contiguous atoms to form a ring selected from the group consisting of a cycloalkyl having from 3 through 10 contiguous members, a cycloalkenyl having from 5 through 10 contiguous members, and a heterocyclyl having from 5 through 10 contiguous members;

$R_{XV-30}$, when bonded to $A_{XV-1}$, is taken together to form an intra-ring branched spacer connecting the $A_{XV-1}$-carbon at the point of attachment of $R_{XV-30}$ to the points of bonding of each member of any one of substituent pairs selected from the group consisting of susbstituent pairs $R_{XV-10}$ and $R_{XV-11}$, $R_{XV-10}$ and $R_{XV-31}$, $R_{XV-10}$ and $R_{XV-32}$, $R_{XV-10}$ and $R_{XV-12}$, $R_{XV-11}$ and $R_{XV-31}$, $R_{XV-11}$ and $R_{XV-32}$, $R_{XV-11}$ and $R_{XV-12}$, $R_{XV-31}$ and $R_{XV-32}$, $R_{XV-31}$ and $R_{XV-12}$, and $R_{XV-32}$ and $R_{XV-12}$ and wherein said intra-ring branched spacer is selected to form two rings selected from the group consisting of cycloalkyl having from 3 through 10 contiguous members, cycloalkenyl having from 5 through 10 contiguous members, and heterocyclyl having from 5 through 10 contiguous members;

$R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$ and $R_{XV-36}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, alkylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, dialkoxyphosphono, and diaralkoxyphosphonoalkyl with the provisos that $R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$, and $R_{XV-36}$ are each independently selected to maintain the tetravalent nature of carbon, trivalent nature of nitrogen, the divalent nature of sulfur, and the divalent nature of oxygen, that no more than three of the $R_{XV-33}$ and $R_{XV-34}$ substituents are simultaneously selected from other than the group consisting of hydrido and halo, and that no more than three of the $R_{XV-35}$ and $R_{XV-36}$ substituents are simultaneously selected from other than the group consisting of hydrido and halo;

$R_{XV-9}$, $R_{XV-10}$, $R_{XV-11}$, $R_{XV-12}$, $R_{XV-13}$, $R_{XV-31}$, and $R_{XV-32}$ are independently selected to be oxo with the provisos that $B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C and S, no more than two of $R_{XV-9}$, $R_{XV-10}$, $R_{XV-11}$, $R_{XV-12}$, $R_{XV-13}$, $R_{XV-31}$, and $R_{XV-32}$ are simultaneously oxo, and that $R_{XV-9}$, $R_{XV-10}$, $R_{XV-11}$, $R_{XV-12}$, $R_{XV-13}$, $R_{XV-31}$, and $R_{XV-32}$ are each independently selected to maintain the tetravalent nature of carbon, trivalent nature of nitrogen, the divalent nature of sulfur, and the divalent nature of oxygen;

$R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$, $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$ and $R_{XV-12}$ and $R_{XV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$ is used at the same time and that no more than one of the group consisting of spacer pairs $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are used at the same time;

$R_{XV-9}$ and $R_{XV-11}$, $R_{XV-9}$ and $R_{XV-12}$, $R_{XV-9}$ and $R_{XV-13}$, $R_{XV-9}$ and $R_{XV-31}$, $R_{XV-9}$ and $R_{XV-32}$, $R_{XV-10}$ and $R_{XV-12}$, $R_{XV-10}$ and $R_{XV-13}$, $R_{XV-10}$ and $R_{XV-31}$, $R_{XV-10}$ and $R_{XV-32}$, $R_{XV-11}$ and $R_{XV-12}$, $R_{XV-11}$ and $R_{XV-13}$, $R_{XV-11}$ and $R_{XV-32}$, $R_{XV-12}$ and $R_{XV-31}$, $R_{XV-13}$ and $R_{XV-31}$, and $R_{XV-13}$ and $R_{XV-32}$ are independently selected to form a spacer pair wherein said spacer pair is taken together to form a linear spacer moiety selected from the group consisting of a covalent single bond and a moiety having from 1 through 3 contiguous atoms to form a ring selected from the group consisting of a cycloalkyl having from 3 through 8 contiguous members, a cycloalkenyl having from 5 through 8 contiguous members, a saturated heterocyclyl having from 5 through 8 contiguous members and a partially saturated heterocyclyl having from 5 through 8 contiguous members with the provisos that no more than one of said group of spacer pairs is used at the same time;

$R_{XV-37}$ and $R_{XV-38}$ are independently selected from the group consisting of hydrido, alkoxy, alkoxyalkyl, hydroxy, amino, thio, halo, haloalkyl, alkylamino, alkylthio, alkylthioalkyl, cyano, alkyl, alkenyl, haloalkoxy, and haloalkoxyalkyl.

Compounds of Formula XV and their methods of manufacture are disclosed in PCT Publication No. WO 00/18723, which is incorporated herein by reference in its entirety for all purposes.

In a preferred embodiment, the CETP inhibitor is selected from the following compounds of Formula XV:

3-[[3-(4-chloro-3-ethylphenoxy)phenyl](cyclohexylmethyl)amino]-1,1,1-trifluoro-2-propanol;
3-[[3-(4-chloro-3-ethylphenoxy)phenyl](cyclopentylmethyl)amino]-1,1,1-trifluoro-2-propanol;
3-[[3-(4-chloro-3-ethylphenoxy)phenyl](cyclopropylmethyl)amino]-1,1,1-trifluoro-2-propanol;
3-[[3-(4-chloro-3-ethylphenoxy)phenyl][(3-trifluoromethyl)cyclohexylmethyl]amino]-1,1,1-trifluoro-2-propanol;
3-[[3-(4-chloro-3-ethylphenoxy)phenyl][(3-pentafluoroethyl) cyclohexyl-methyl]amino]-1,1,1-trifluoro-2-propanol;
3-[[3-(4-chloro-3-ethylphenoxy)phenyl][(3-trifluoromethoxy) cyclohexyl-methyl]amino]-1,1,1-trifluoro-2-propanol;
3-[[3-(4-chloro-3-ethylphenoxy)phenyl][[3-(1,1,2,2-tetrafluoroethoxy)cyclo-hexylmethyl]amino]-1,1,1-trifluoro-2-propanol;
3-[[3-(3-trifluoromethoxyphenoxy)phenyl](cyclohexylmethyl)amino]-1,1,1-trifluoro-2-propanol;
3-[[3-(3-trifluoromethoxyphenoxy)phenyl](cyclopentylmethyl)amino]-1,1,1-trifluoro-2-propanol;
3-[[3-(3-trifluoromethoxyphenoxy)phenyl](cyclopropylmethyl)amino]-1,1,1-trifluoro-2-propanol;
3-[[3-(3-trifluoromethoxyphenoxy)phenyl][(3-trifluoromethyl)cyclohexylmethyl]amino]-1,1,1-trifluoro-2-propanol;
3-[[3-(3-trifluoromethoxyphenoxy)phenyl](3-pentafluoroethyl)cyclohexylmethyl]amino]-1,1,1-trifluoro-2-propanol;
3-[[3-(3-trifluoromethoxyphenoxy)phenyl][(3-trifluoromethoxy)cyclohexyl-methyl]amino]-1,1,1-trifluoro-2-propanol;
3-[[3-(3-trifluoromethoxyphenoxy)phenyl][[3-(1,1,2,2-tetrafluoroethoxy)cyclohexyl-methyl]amino]-1,1,1-trifluoro-2-propanol;
3-[[3-(3-isopropylphenoxy)phenyl](cyclohexylmethyl)amino]-1,1,1-trifluoro-2-propanol:
3-[[3-(3-isopropylphenoxy)phenyl](cyclopentylmethyl)amino]-1,1,1-trifluoro-2-propanol;
3-[[3-(3-isopropylphenoxy)phenyl](cyclopropylmethyl)amino]-1,1,1-trifluoro-2-propanol;
3-[[3-(3-isopropylphenoxy)phenyl][(3-trifluoromethyl)cyclohexylmethyl]amino]-1,1,1-trifluoro-2-propanol;
3-[[3-(3-isopropylphenoxy)phenyl][(3-pentafluoroethyl)cyclohexylmethyl]amino]-1,1,1-trifluoro-2-propanol;
3-[[3-(3-isopropylphenoxy)phenyl][(3-trifluoromethoxy)cyclohexylmethyl]amino]-1,1,1-trifluoro-2-propanol;
3-[[3-(3-isopropylphenoxy)phenyl][3-(1,1,2,2-tetrafluoroethoxy)cyclohexylmethyl]amino]-1,1,1-trifluoro-2-propanol;
3-[[3-(2,3-dichlorophenoxy)phenyl](cyclohexylmethyl)amino]-1,1,1-trifluoro-2-propanol;
3-[[3-(2,3-dichlorophenoxy)phenyl](cyclopentylmethyl)amino]-1,1,1-trifluoro-2-propanol;
3-[[3-(2,3-dichlorophenoxy)phenyl](cyclopropylmethy)amino]-1,1,1-trifluoro-2-propanol;
3-[[3-(2,3-dichlorophenoxy)phenyl][(3-trifluoromethyl)cyclohexyl-methyl]amino]-1,1,1-trifluoro-2-propanol;
3-[[3-(2,3-dichlorophenoxy)phenyl][(3-pentafluoroethyl)cyclohexylmethyl]amino]-1,1,1-trifluoro-2-propanol;
3-[[3-(2,3-dichlorophenoxy)phenyl][(3-trifluoromethoxy)cyclohexylmethyl]amino]-1,1,1-trifluoro-2-propanol;
3-[[3-(2,3-dichlorophenoxy)phenyl][3-(1,1,2,2-tetrafluoroethoxy)cyclo-hexylmethyl]amino]-1,1,1-trifluoro-2-propanol;
3-[[3-(4-fluorophenoxy)phenyl](cyclohexylmethyl)amino]-1,1,1-trifluoro-2-propanol;
3-[[3-(4-fluorophenoxy)phenyl](cyclopentylmethyl)amino]-1,1,1-trifluoro-2-propanol;
3-[[3-(4-fluorophenoxy)phennyl](cyclopropylmethyl)amino]-1,1,1-triflouro-2-propanol;
3-[[3-(4-fluorophenoxy)phenyl][(3-trifluoromethyl) cyclohexyl-methyl]amino]-1,1,1-trifluoro-2-propanol;
3-[[3-(4-fluorophenoxy)phenyl][(3-pentafluoroethyl) cyclohexyl-methyl]amino]-1,1,1-trifluoro-2-propanol;
3-[[3-(4-fluorophenoxy)phenyl][(3-trifluoromethoxy) cyclohexyl-methyl]amino]-1,1,1-trifluoro-2-propanol;
3-[[3-(4-fluorophenoxy)phenyl][[3-(1,1,2,2-tetrafluoroethoxy)cyclohexylmethyl]amino]-1,1,1-trifluoro-2-propanol;
3-[[3-(3-trifluoromethoxybenzyloxy]phenyl](cyclohexylmethyl)amino]-1,1,1-trifluoro-2-propanol;
3-[[3-(3-trifluoromethoxybenzyloxy]phenyl](cyclopentylmethyl)amino]-1,1,1-trifluoro-2-propanol;
3-[[3-(3-trifluoromethoxybenzyloxy]phenyl](cyclopropylmethyl)amino]-1,1,1-trifluoro-2-propanol;
3-[[3-(3-trifluoromethoxybenzyloxy]phenyl][(3-trifluoromethyl)cyclohexyl-methyl]amino]-1,1,1-trifluoro-2-propanol;
3-[[3-(3-trifluoromethoxybenzyloxy]phenyl][(3-pentafluoroethyl)cyclohexyl-methyl]amino]-1,1,1-trifluoro-2-propanol;
3-[[3-(3-trifluoromethoxybenzyloxy]phenyl][(3-trifluoromethoxy)cyclohexyl-methyl]amino]-1,1,1-trifluoro-2-propanol;
3-[[3-(3-trifluoromethoxybenzyloxy]phenyl][3-(1,1,2,2-tetrafluoroethoxy)-cyclohexylmethyl]amino]-1,1,1-trifluoro-2-propanol;
3-[[3-(3-trifluoromethylbenzyloxy)phenyl](cyclohexylmethyl)amino]-1,1,1-trifluoro-2-propanol;
3-[[3-(3-trifluoromethylbenzyloxy)phenyl](cyclopentylmethyl)amino]-1,1,1-trifluoro-2-propanol;
3-[[3-(3-trifluoromethylbenzyloxy)phenyl](cyclopropylmethyl)amino]-1,1,1-trifluoro-2-propanol;

3-[[3-(3-trifluoromethylbenzyloxy)phenyl][(3-trifluoromethyl)cyclohexylmethyl]amino]-1,1,1-trifluoro-2-propanol;

3-[[3-(3-trifluoromethylbenzyloxy)phenyl][(3-pentafluoroethyl)cyclohexylmethyl]amino]-1,1,1-trifluoro-2-propanol;

3-[[3-(3-trifluoromethylbenzyloxy)phenyl][(3-trifluoromethoxy)cyclohexyl-methyl]amino]-1,1,1-trifluoro-2-propanol;

3-[[3-(3-trifluoromethylbenzyloxy)phenyl][3-(1,1,2,2-tetrafluoroethoxy)cyclohexyl-methyl]amino]-1,1,1-trifluoro-2-propanol;

3-[[[(3-trifluoromethyl)phenyl]methyl](cyclohexyl)amino]-1,1,1-trifluoro-2-propanol;

3-[[[(3-pentafluoroethyl)phenyl]methyl](cyclohexyl)amino]-1,1,1-trifluoro-2-propanol;

3-[[[(3-trifluoromethoxy)phenyl]methyl](cyclohexyl)amino]-1,1,1-trifluoro-2-propanol;

3-[[[3-(1,1,2,2-tetrafluoroethoxy)phenyl]methyl](cyclohexyl)amino]-1,1,1-trifluoro-2-propanol;

3-[[[(3-trifluoromethyl)phenyl]methyl](4-methylcyclohexyl)amino]-1,1,1-trifluoro-2-propanol;

3-[[[(3-pentafluoroethyl)phenyl]methyl](4-methylcyclohexyl)amino]-1,1,1-trifluoro-2-propanol;

3-[[[(3-trifluoromethoxy)phenyl]methyl](4-methylcyclohexyl)amino]-1,1,1-trifluoro-2-propanol;

3-[[[3-(1,1,2,2-tetrafluoroethoxy)phenyl]methyl](4-methylcyclohexyl)amino]-1,1,1-trifluoro-2-propanol;

3-[[[(3-trifluoromethyl]phenyl]methyl](3-trifluoromethylcyclohexyl)amino]-1,1,1-trifluoro-2-propanol;

3-[[[(3-pentafluoroethyl)phenyl]methyl](3-trifluoromethylcyclohexyl)amino]-1,1,1-trifluoro-2-propanol;

3-[[[(3-trifluoromethoxy)phenyl]methyl](3-trifluoromethylcyclohexyl)amino]-1,1,1-trifluoro-2-propanol;

3-[[[3-(1,1,2,2-tetrafluoroethoxy)phenyl]methyl](3-trifluoromethylcyclohexyl)amino]-1,1,1-trifluoro-2-propanol;

3-[[[(3-trifluoromethyl)phenyl]methyl][3-(4-chloro-3-ethylphenoxy)cyclohexyl]amino]-1,1,1-trifluoro-2-propanol;

3-[[[(3-pentafluoroethyl)phenyl]methyl][3-(4-chloro-3-ethylphenoxy)cyclohexyl]amino]-1,1,1-trifluoro-2-propanol;

3-[[[(3-trifluoromethoxy)phenyl]methyl][3-(4-chloro-3-methylphenoxy)cyclo-hexyl]amino]-1,1,1-trifluoro-2-propanol;

3-[[[3-(1,1,2,2-tetrafluoroethoxy)phenyl]methyl][3-(4-chloro-3-ethylphenoxy)cyclohexyl]amino]-1,1,1-trifluoro-2-propanol;

3-[[[(3-trifluoromethyl)phenyl]methyl](3-phenoxycyclohexyl)amino]-1,1,1-trifluoro-2-propanol;

3-[[[(3-pentafluoroethyl)phenyl]methyl](3-phenoxycyclohexyl)amino]-1,1,1-trifluoro-2-propanol;

3-[[[(3-trifluoromethoxy)phenyl]methyl](3-phenoxycyclohexyl)amino]-1,1,1-trifluoro-2-propanol;

3-[[[3-(1,1,2,2-tetrafluoroethoxy)phenyl]methyl](3-phenoxycyclohexyl)amino]-1,1,1-trifluoro-2-propanol;

3-[[[(3-trifloromethyl)phenyl]methyl](3-isopropoxycyclohexyl)amino]-1,1,1-trifluoro-2-propanol;

3-[[[(3-pentafluoroethyl)phenyl]methyl](3-isopropoxycyclohexyl)amino]-1,1,1-trifluoro-2-propanol;

3-[[[(3-trifluoromethoxy)phenyl]methyl](3-isopropoxycyclohexyl)amino]-1,1,1-trifluoro-2-propanol;

3-[[[3-(1,1,2,2-tetrafluoroethoxy)phenyl]methyl](3-isopropoxycyclohexyl)-amino]-1,1,1-trifluoro-2-propanol;

3-[[[(3-trifluoromethyl)phenyl]methyl](3-cyclopentyloxycyclohexyl]amino]-1,1,1-trifluoro-2-propanol;

3-[[[(3-pentafluoroethyl]phenyl]methyl](3-cyclopentyloxycyclohexyl)amino]-1,1,1-trifluoro-2-propanol;

3-[[[(3-trifluoromethoxy)phenyl]methyl](3-cyclopentyloxycyclohexyl)amino]-1,1,1-trifluoro-2-propanol;

3-[[[3-(1,1,2,2-tetrafluoroethoxy)phenyl]methyl](3-cyclopentyloxycyclohexyl)-amino]-1,1,1-trifluoro-2-propanol;

3-[[[(2-trifluoromethyl)pyrid-6-yl]methyl](3-isopropoxycyclohexyl)amino]-1,1,1-trifluoro-2-propanol;

3-[[[(2-trifluoromethyl)pyrid-6-yl]methyl](3-cyclopentyloxycyclohexyl)-amino]-1,1,1-trifluoro-2-propanol;

3-[[[(2-trifluoromethyl)pyrid-6-yl]methyl](3-phenoxycyclohexyl)amino]-1,1,1-trifluoro-2-propanol;

3-[[[(2-trifluoromethyl)pyrid-6-yl]methyl](3-trifluoromethylcyclohexyl)amino]-1,1,1-trifluoro-2-propanol;

3-[[[(2-trifluoromethyl)pyrid-6-yl]methyl][3-(4-chloro-3-ethylphenoxy)cyclohexyl]amino]-1,1,1-trifluoro-2-propanol;

3-[[[(2-trifluoromethyl)pyrid-6-yl]methyl][3-(1,1,2,2-tetrafluoroethoxy)cyclo-hexyl]amino]-1,1,1-trifluoro-2-propanol;

3-[[[(2-trifluoromethyl)pyrid-6-yl]methyl](3-pentafluoroethylcyclohexyl)amino]-1,1,1-trifluoro-2-propanol;

3-[[[(2-trifluoromethyl)pyrid-6-yl]methyl](3-trifluoromethoxycyclohexyl)amino]-1,1,1-trifluoro-2-propanol;

3-[[[(3-trifluoromethyl)phenyl]methyl][3-(4-chloro-3-ethylphenoxy)propyl]-amino]-1,1,1-trifluoro-2-propanol;

3-[[[(3-pentafluoroethyl)phenyl]methyl][3-(4-chloro-3-ethylphenoxy)propyl]-amino]-1,1,1-trifluoro-2-propanol;

3-[[[(3-trifluoromethoxy)phenyl]methyl][3-(4-chloro-3-ethylphenoxy)propyl]-amino]-1,1,1-trifluoro-2-propanol;

3-[[[3-(1,1,2,2-tetrafluoroethoxy)phenyl]methyl][3-(4-chloro-3-ethylphenoxy)propyl]amino]-1,1,1-trifluoro-2-propanol;

3-[[[(3-trifluoromethyl)phenyl]methyl][3-(4-chloro-3-ethylphenoxy)-2,2,-difluropropyl]amino]-1,1,1-trifluoro-2-propanol;

3-[[[(3-pentafluoroethyl)phenyl]methyl][3-(4-chloro-3-ethylphenoxy)-2,2-difluropropyl]amino]-1,1,1-trifluoro-2-propanol;

3-[[[(3-trifluoromethoxy)phenyl]methyl][3-(4-chloro-3-ethylphenoxy)-2,2,-difluropropyl]amino]-1,1,1-trifluoro-2-propanol;

3-[[[3-(1,1,2,2-tetrafluoroethoxy)phenyl]methyl][3-(4-chloro-3-ethylphenoxy)-2,2,-difluropropyl]amino]-1,1,1-trifluoro-2-propanol;

3-[[[(3-trifluoromethyl)phenyl]methyl][3-(isopropoxy)propyl]amino]-1,1,1-trifluoro-2-propanol;

3-[[[(3-pentafluoroethyl)phenyl]methyl][3-(isopropoxy)propyl]amino]-1,1,1-trifluoro-2-propanol;

3-[[[(3-trifluoromethoxy)phenyl]methyl][3-(isopropoxy)propyl]amino]-1,1,1-trifluoro-2-propanol;

3-[[[3-(1,1,2,2-tetrafluoroethoxy)phenyl]methyl][3-(isopropoxy)propyl]amino]-1,1,1-trifluoro-2-propanol; and 3-[[[3-(1,1,2,2-tetrafluoroethoxy)phenyl]methyl][3-(phenoxy)propyl]amino]-1,1,1-trifluoro-2-propanol.

Another class of CETP inhibitors that finds utility with the present invention consists of (R)-chiral halogenated 1-substituted amino-(n+I)-alkanols having the Formula XVI Formula XVI

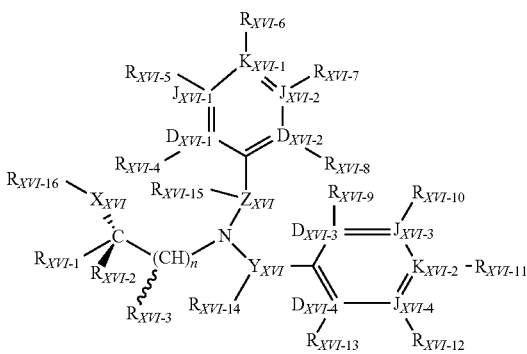

and pharmaceutically acceptable forms thereof, wherein:
$n_{XVI}$ is an integer selected from 1 through 4;
$X_{XVI}$ is oxy;
$R_{XVI-1}$ is selected from the group consisting of haloalkyl, haloalkenyl, haloalkoxymethyl, and haloalkenyloxymethyl with the proviso that $R_{XVI-1}$ has a higher Cahn-Ingold-Prelog stereochemical system ranking than both $R_{XVI-2}$ and $(CHR_{XVI-3})_n$—$N(A_{XVI})Q_{XVI}$ wherein $A_{XVI}$ is Formula XVI-(II) and Q is Formula XVI-(III);

XVI-II

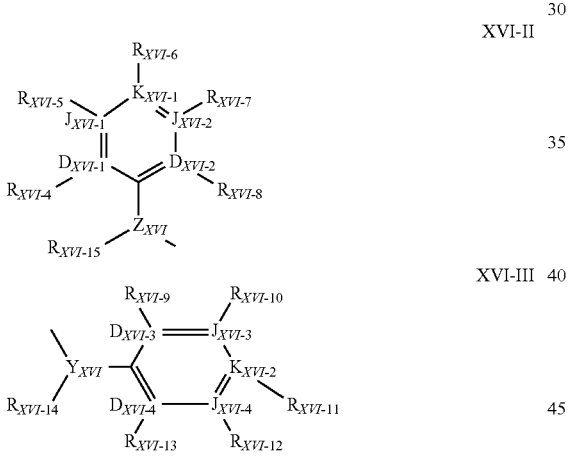

XVI-III $R_{XVI-16}$ is selected from the group consisting of hydrido, alkyl, acyl, aroyl, heteroaroyl, trialkylsilyl, and a spacer selected from the group consisting of a covalent single bond and a linear spacer moiety having a chain length of 1 to 4 atoms linked to the point of bonding of any aromatic substituent selected from the group consisting of $R_{XVI-4}$, $R_{XVI-8}$, $R_{XVI-9}$, and $R_{XVI-13}$ to form a heterocyclyl ring having from 5 through 10 contiguous members;

$D_{XVI-1}$, $D_{XVI-2}$, $J_{XVI-1}$, $J_{XVI-2}$ and $K_{XVI-1}$ are independently selected from the group consisting of C, N, O, S and covalent bond with the provisos that no more than one of $D_{XVI-1}$, $D_{XVI-2}$, $J_{XVI-1}$, $J_{XVI-2}$ and $K_{XVI-1}$ is a covalent bond, no more than one $D_{XVI-1}$, $D_{XVI-2}$, $J_{XVI-1}$, $J_{XVI-2}$ and $K_{XVI-1}$ is be O, no more than one of $D_{XVI-1}$, $D_{XVI-2}$, $J_{XVI-1}$, $J_{XVI-2}$ and $K_{XVI-1}$ is S, one of $D_{XVI-1}$, $D_{XVI-2}$, $J_{XVI-1}$, $J_{XVI-2}$ and $K_{XVI-1}$ must be a covalent bond when two of $D_{XVI-1}$, $D_{XVI-2}$, $J_{XVI-1}$, $J_{XVI-2}$ and $K_{XVI-1}$ are O and S, and no more than four of $D_{XVI-1}$, $D_{XVI-2}$, $J_{XVI-1}$, $J_{XVI-2}$ and $K_{XVI-1}$ is N;

$D_{XVI-3}$, $D_{XVI-4}$, $J_{XVI-3}$, $J_{XVI-4}$ and $K_{XVI-2}$ are independently selected from the group consisting of C, N, O, S and covalent bond with the provisos that no more than one is a covalent bond, no more than one of $D_{XVI-3}$, $D_{XVI-4}$, $J_{XVI-3}$, $J_{XVI-4}$ and $K_{XVI-2}$ is O, no more than one of $D_{XVI-3}$, $D_{XVI-4}$, $J_{XVI-3}$, $J_{XVI-4}$ and $K_{XVI-2}$ is S, no more than two of $D_{XVI-3}$, $D_{XVI-4}$, $J_{XVI-3}$, $J_{XVI-4}$ and $K_{XVI-2}$ is O and S, one of $D_{XVI-3}$, $D_{XVI-4}$, $J_{XVI-3}$, $J_{XVI-4}$ and $K_{XVI-2}$ must be a covalent bond when two of $D_{XVI-3}$, $D_{XVI-4}$, $J_{XVI-3}$, $J_{XVI-4}$ and $K_{XVI-2}$ are O and S, and no more than four of $D_{XVI-3}$, $D_{XVI-4}$, $J_{XVI-3}$, $J_{XVI-4}$ and $K_{XVI-2}$ are N;

$R_{XVI-2}$ is selected from the group consisting of hydrido, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl, with the proviso that $R_{XVI-2}$ has a lower Cahn-Ingold-Prelog system ranking than both $R_{XVI-1}$ and $(CHR_{XVI-3})_n$—$N(A_{XVI})Q_{XVI}$;

$R_{XVI-3}$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl, with the provisos that $(CHR_{XVI-3})_n$—$N(A_{XVI})Q_{XVI}$ has a lower Cahn-Ingold-Prelog stereochemical system ranking than $R_{XVI-1}$ and a higher Cahn-Ingold-Prelog stereochemical system ranking than $R_{XVI-2}$;

$Y_{XVI}$ is selected from a group consisting of a covalent single bond, $(C(R_{XVI-14})_2)_q$ wherein q is an integer selected from 1 and 2 and $(CH(R_{XVI-14}))_g$—$W_{XVI}$—$(CH(R_{XVI-14}))_p$ wherein g and p are integers independently selected from 0 and 1;

$R_{XVI-14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$Z_{XVI}$ is selected from a group consisting of a covalent single bond, $(C(R_{XVI-15})_2)_q$, wherein q is an integer selected from 1 and 2, and $(CH(R_{XVI-15}))_j$—$W_{XVI}$—$(CH(R_{XVI-15}))_k$ wherein j and k are integers independently selected from 0 and 1;

$W_{XVI-1}$ is selected from the group consisting of O, C(O), C(S), C(O)N($R_{XVI-114}$), C(S)N($R_{XVI-14}$), ($R_{XVI-14}$)NC(O), ($R_{XVI-14}$)NC(S), S, S(O), S(O)$_2$, S(O)$_2$N($R_{XVI-14}$), ($R_{XVI-14}$)NS(O)$_2$, and N($R_{XVI-14}$) with the proviso that $R_{XVI-14}$ is other than cyano;

$R_{XVI-15}$ is selected, from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkyl, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl, amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that $R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are each independently selected to maintain the tetravalent nature of carbon, trivalent nature of nitrogen, the divalent nature of sulfur, and the divalent nature of oxygen;

$R_{XVI-4}$ and $R_{XVI-5}$, $R_{XVI-5}$ and $R_{XVI-6}$, $R_{XVI-6}$ and $R_{XVI-7}$, $R_{XVI-7}$ and $R_{XVI-8}$, $R_{XVI-8}$ and $R_{XVI-9}$, $R_{XVI-9}$ and $R_{XVI-10}$, $R_{XVI-10}$ and $R_{XVI-11}$, $R_{XVI-11}$ and $R_{XVI-12}$, and $R_{XVI-12}$ and $R_{XVI-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XVI-4}$ and $R_{XVI-5}$, $R_{XVI-5}$ and $R_{XVI-6}$, $R_{XVI-6}$ and $R_{XVI-7}$, and $R_{XVI-7}$ and $R_{XVI-8}$ is used at the same time and that no more than one of the group consisting of spacer pairs $R_{XIV-9}$ and $R_{XVI-10}$, $R_{XVI-10}$ and $R_{XVI-11}$, $R_{XVI-11}$ and $R_{XVI-12}$, and $R_{XVI-12}$ and $R_{XVI-13}$ can be used at the same time;

$R_{XVI-4}$ and $R_{XVI-9}$, $R_{XVI-14}$ and $R_{XVI-13}$, $R_{XVI-8}$ and $R_{XVI-9}$, and $R_{XVI-8}$ and $R_{XVI-13}$ is independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is used at the same time.

Compounds of Formula XVI and their methods of manufacture are disclosed in PCT Publication No. WO 00/18724, which is incorporated herein by reference in its entirety for all purposes.

In a preferred embodiment, the CETP inhibitor is selected from the following compounds of Formula XVI:

(2R)-3-[[3-(3-trifluoromethoxyphenoxy)phenyl][[3-(1,1,2,2-tetrafluoroethoxy)phenyl]methyl]amino]-1,1,1-trifluoro-2-propanol;

(2R)-3-[[3-(3-isopropylphenoxy)phenyl][[3-(1,1,2,2-tetrafluoroethoxy)phenyl]-methyl]amino]-1,1,1-trifluoro-2-propanol;

(2R)-3-[[3-(3-cyclopropylphenoxy)phenyl][[3-(1,1,2,2-tetrafluoroethoxy)phenyl]-methyl]amino]-1,1,1-trifluoro-2-propanol;

(2R)-3-[[3-(3-(2-furyl)phenoxy)phenyl][[3-(1,1,2,2-tetrafluoroethoxy)phenyl]-methyl]amino]-1,1,1-trifluoro-2-propanol;

(2R)-3-[[3-(2,3-dichlorophenoxy)phenyl][[3-(1,1,2,2-tetrafluoroethoxy)phenyl]-methyl]amino]-1,1,1-trifluoro-2-propanol;

(2R)-3-[[3-(4-fluorophenoxy)phenyl][[3-(1,1,2,2-tetrafluoroethoxy)phenyl]-methyl]amino]-1,1,1-trifluoro-2-propanol;

(2R)-3-[[3-(4-methylphenoxy)phenyl][[3-(1,1,2,2-tetrafluoroethoxy)phenyl]-methyl]amino]-1,1,1-trifluoro-2-propanol;

(2R)-3-[[3-(2-fluoro-5-bromophenoxy)phenyl][[3-(1,1,2,2-tetrafluoroethoxy)phenyl]-methyl]amino]-1,1,1-trifluoro-2-propanol;

(2R)-3-[[3-(4-chloro-3-ethylphenoxy)phenyl][[3-(1,1,2,2-tetrafluoroethoxy)phenyl]-methyl]amino]-1,1,1-trifluoro-2-propanol;

(2R)-3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

(2R)-3-[[3-[3-(pentafluoroethyl)phenoxy]phenyl][[3-(1,1,2,2-tetrafluoroethoxy)-phenyl]methyl]amino]-1,1,1-trifluoro-2-propanol;

(2R)-3-[[3-(3,5-dimethylphenoxy)phenyl][[3-(1,1,2,2-tetrafluoroethoxy)phenyl]-methyl]amino]-1,1,1-trifluoro-2-propanol;

(2R)-3-[[3-(3-ethylphenoxy)phenyl][[3-(1,1,2,2-tetrafluoroethoxy)phenyl]-methyl]amino]-1,1,1-trifluoro-2-propanol;

(2R)-3-[[3-(3-t-butylphenoxy)phenyl][[3-(1,1,2,2-tetrafluoroethoxy)phenyl]-methyl]amino]-1,1,1-trifluoro-2-propanol:

(2R)-3-[[3-(3-methylphenoxy)phenyl][[3-(1,1,2,2-tetrafluoroethoxy)phenyl]-methyl]amino]-1,1,1-trifluoro-2-propanol;

(2R)-3-[[3-(5,6,7,8-tetrahydro-2-naphthoxy)phenyl][[3-(1,1,2,2-tetrafluoroethoxy)phenyl]methyl]amino]-1,1,1-trifluoro-2-propanol;

(2R)-3-[[3-(phenoxy)phenyl][[3-(1,1,2,2-tetrafluoroethoxy)phenyl]methyl]amino]-1,1,1-trifluoro-2-propanol;

(2R)-3-[[3-[3-(N,N-dimethylamino)phenoxy]phenyl][[3-(1,1,2,2-tetrafluoroethoxy)phenyl]methyl]amino]-1,1,1-trifluoro-2-propanol;

(2R)-3-[[[3-(1,1,2,2,-tetrafluoroethoxy)phenyl]methyl][3-[[3-(trifluoromethoxy)-phenyl]methoxy]phenyl]amino]-1,1,1-trifluoro-2-propanol;

(2R)-3-[[[3-(1,1,2,2-tetrafluoroethoxy)phenyl]methyl][3-[[3-(trifluoromethyl)phenyl]methoxy]phenyl]amino]-1,1,1-trifluoro-2-propanol;

(2R)-3-[[[3-(1,1,2,2-tetrafluoroethoxy)phenyl]methyl][3-[[3,5-dimethylphenyl]-methoxy]phenyl]amino]-1,1,1-trifluoro-2-propanol;

(2R)-3-[[[3-(1,1,2,2-tetrafluoroethoxy)phenyl]methyl][3-[[3-(trifluoromethylthio)-phenyl]methoxy]phenyl]amino]-1,1,1-trifluoro-2-propanol;

(2R)-3-[[[3-(1,1,2,2-tetrafluoroethoxy)phenyl]methyl][3-[[3,5-difluorophenyl]-methoxy]phenyl]amino]-1,1,1-trifluoro-2-propanol;

(2R)-3-[[[3-(1,1,2,2-tetrafluoroethoxy)phenyl]methyl][3-[cyclohexylmethoxy]-phenyl]amino]-1,1,1-trifluoro-2-propanol;

(2R)-3-[[3-(2-difluoromethoxy-4-pyridyloxy)phenyl][[3-(1,1,2,2-tetrafluoroethoxy)-phenyl]methyl]amino]-1,1,1-trifluoro-2-propanol;

(2R)-3-[[3-(2-trifluoromethyl-4-pyridyloxy)phenyl][[3-(1,1,2,2-tetrafluoroethoxy)-phenyl]methyl]amino]-1,1,1-trifluoro-2-propanol;

(2R)-3-[[3-(3-difluoromethoxyphenoxy)phenyl][[3-(1,1,2,2-tetrafluoroethoxy)phenyl]methyl]amino]-1,1,1-trifluoro-2-propanol;

(2R)-3-[[[3-(3-trifuoromethylthio)phenoxy]phenyl][[3-(1,1,2,2-tetrafluoroethoxy)-phenyl]methyl]amino]-1,1,1-trifluoro-2-propanol;

(2R)-3-[[3-(4-chloro-3-trifluoromethylphenoxy)phenyl][[3-(1,1,2,2-tetrafluoroethoxy)-phenyl]methyl]amino]-1,1,1-trifluoro-2-propanol;

(2R)-3-[[3-(3-trifluoromethoxyphenoxy)phenyl][[3-(pentafluoroethyl)phenyl]-methyl]amino]-1,1,1-trifluoro-2-propanol;

(2R)-3-[[3-(3-isopropylphenoxy)phenyl][[3-(pentafluoroethyl)phenyl]methyl]-amino]-1,1,1-trifluoro-2-propanol;

(2R)-3-[[3-(3-cyclopropylphenoxy)phenyl][[3-(pentafluoroethyl)phenyl]methyl]-amino]-1,1,1-trifluoro-2-propanol;

(2R)-3-[[3-(3-(2-furyl)phenoxy)phenyl][[3-(pentafluoroethyl)phenyl]methyl]-amino]-1,1,1-trifluoro-2-propanol;

(2R)-3-[[3-(2,3-dichlorophenoxy)phenyl][[3-(pentafluoroethyl)phenyl]methyl]-amino]-1,1,1-trifluoro-2-propanol;

(2R)-3-[[3-(4-fluorophenoxy)phenyl][[3-(pentafluoroethyl)phenyl]methyl]amino]-1,1,1-trifluoro-2-propanol;

(2R)-3-[[3-(4-methylphenoxy)phenyl][[3-(pentafluoroethyl)phenyl]methyl]amino]-1,1,1-trifluoro-2-propanol;

(2R)-3-[[3-(2-fluoro-5-bromophenoxy)phenyl][[3-(pentafluoroethyl)phenyl]methyl]amino]-1,1,1-trifluoro-2-propanol;

(2R)-3-[[3-(4-chloro-3-ethylphenoxy)phenyl][[3-(pentafluoroethyl)phenyl]methyl]amino]-1,1,1-trifluoro-2-propanol;

(2R)-3-[[3-[3-(1,1,2,2-tetrafluoroethoxy)phenoxy]phenyl][[3-(pentafluoroethyl)-phenyl]methyl]amino]-1,1,1-trifluoro-2-propanol;

(2R)-3-[[3-[3-(pentafluoroethyl)phenoxy]phenyl][[3-(pentafluoroethyl)phenyl]methyl]amino]-1,1,1-trifluoro-2-propanol;

(2R)-3-[[3-(3,5-dimethylphenoxy)phenyl][[3-(pentafluoroethyl) phenyl]methyl]-amino]-1,1,1-trifluoro-2-propanol;

(2R)-3-[[3-(3-ethylphenoxy)phenyl][[3-(pentafluoroethyl)phenyl]methyl]amino]-1,1,1-trifluoro-2-propanol;

(2R)-3-[[3-(3-t-butylphenoxy)phenyl][[3-(pentafluoroethyl)phenyl]methyl]amino]-1,1,1-trifluoro-2-propanol;

(2R)-3-[[3-(3-methylphenoxy)phenyl][[3-(pentafluoroethyl)phenyl]methyl]amino]-1,1,1-trifluoro-2-propanol;

(2R)-3-[[3-(5,6,7,8-tetrahydro-2-naphthoxy)phenyl][[3-(pentafluoroethyl)phenyl]-methyl]amino]-1,1,1-trifluoro-2-propanol;

(2R)-3-[[3-(phenoxy)phenyl][[3(pentafluoroethyl) phenyl]methyl]amino]-1,1,1-trifluoro-2-propanol;

(2R)-3-[[3-[3-(N,N-dimethylamino)phenoxy]phenyl][[3 (pentafluoroethyl)phenyl]-methyl]amino]-1,1,1-trifluoro-2-propanol;

(2R)-3-[[[3-(pentafluoroethyl)phenyl]methyl][3-[[3-(trifluoromethoxy)phenyl]-methoxy]phenyl]amino]-1,1,1-trifluoro-2-propanol;

(2R)-3-[[[3-(pentafluoroethyl)phenyl]methyl][3-[[3-(trifluoromethyl)-phenyl]-methoxy]phenyl]amino]-1,1,1-trifluoro-2-propanol;

(2R)-3-[[[3-(pentafluoroethyl)phenyl]methyl][3-[[3,5-dimethylphenyl]methoxy-phenyl]amino]-1,1,1-trifluoro-2-propanol;

(2R)-3-[[[3-(pentafluoroethyl)phenyl]methyl][3-[[3-(trifluoromethylthio)phenyl]-methoxy]phenyl]amino]-1,1,1-trifluoro-2-propanol;

(2R)-3-[[[3-(pentafluoroethyl)phenyl]methyl][3-[[3,5-difluorophenyl]methoxy-phenyl]amino]-1,1,1-trifluoro-2-propanol;

(2R)-3-[[[3-(pentafluoroethyl)phenyl]methyl][3-[cyclohexylmethoxy]phenyl]-amino]-1,1,1-trifluoro-2-propanol;

(2R)-3-[[3-(2-difluoromethoxy-4-pyridyloxy)phenyl][[3-(pentafluoroethyl)phenyl]-methyl]amino]-1,1,1-trifluoro-2-propanol;

(2R)-3-[[3-(2-trifluoromethyl-4-pyridyloxy)phenyl][[3-(pentafluoroethyl)phenyl]-methyl]amino]-1,1,1-trifluoro-2-propanol;

(2R)-3-[[3-(3-difluoromethoxyphenoxy)phenyl][[3-(pentafluoroethyl)phenyl]-methyl]amino]-1,1,1-trifluoro-2-propanol;

(2R)-3-[[[3-(3-trifluoromethylthio)phenoxy]phenyl][[3-(pentafluoroethyl)phenyl]-methyl]amino]-1,1,1-trifluoro-2-propanol;

(2R)-3-[[3-(4-chloro-3-trifluoromethylphenoxy)phenyl][[3-(pentafluoroethyl)-phenyl]methyl]amino]-1,1,1-trifluoro-2-propanol;

(2R)-3-[[3-(3-trifluoromethoxyphenoxy)phenyl][[3-(heptafluoropropyl)phenyl]-methyl]amino]-1,1,1-trifluoro-2-propanol;

(2R)-3-[[3-(3-isopropylphenoxy)phenyl][[3-(heptafluoropropyl)phenyl]methyl]-amino]-1,1,1-trifluoro-2-propanol;

(2R)-3-[[3-(3-cyclopropylphenoxy)phenyl][[3-(heptafluoropropyl)phenyl]methyl]-amino]-1,1,1-trifluoro-2-propanol;

(2R)-3-[[3-(3-(2-furyl)phenoxy)phenyl][[3-(heptafluoropropyl) phenyl]methyl]-amino]-1,1,1-trifluoro-2-propanol;

(2R)-3-[[3-(2,3-dichlorophenoxy)phenyl][[3-(heptafluoropropyl) phenyl]methyl]-amino]-1,1,1-trifluoro-2-propanol;

(2R)-3-[[3-(4-fluorophenoxy)phenyl][[3-(heptafluoropropyl) phenyl]methyl]amino]-1,1,1-trifluoro-2-propanol;

(2R)-3-[[3-(4-methylphenoxy)phenyl][[3-(heptafluoropropyl) phenyl]methyl]amino]-1,1,1,-trifluoro-2-propanol;

(2R)-3-[[3-(2-fluoro-5-bromophenoxy)phenyl][[3-(heptafluoropropyl)phenyl]-methyl]amino]-1,1,1-trifluoro-2-propanol;

(2R)-3-[[3-(4-chloro-3-ethylphenoxy)phenyl][[3-(heptafluoropropyl)phenyl]methyl]-amino]-1,1,1-trifluoro-2-propanol;

(2R)-3-[[3-[3-(1,1,2,2-tetrafluoroethoxy)phenoxy]phenyl][[3-(heptafluoropropyl)-phenyl]methyl]amino]-1,1,1-trifluoro-2-propanol;

(2R)-3-[[3-[3-(pentafluoroethoxy)phenoxy]phenyl][[3-(heptafluoropropyl)phenyl]-methyl]amino]-1,1,1-trifluoro-2-propanol;

(2R)-3-[[3-(3,5-dimethylphenoxy)phenyl][[3-(heptafluoropropyl) phenyl]methyl]-amino]-1,1,1-trifluoro-2-propanol;

(2R)-3-[[3-(3-ethylphenoxy)phenyl][[3-(heptafluoropropyl)phenyl]methyl]amino]-1,1,1-trifluoro-2-propanol;

(2R)-3-[[3-(3-t-butylphenoxy)phenyl][[3-(heptafluoropropyl) phenyl]methyl]amino]-1,1,1-trifluoro-2-propanol;

(2R)-3-[[3-(3-methylphenoxy)phenyl][[3-(heptafluoropropyl) phenyl]methyl]amino]-1,1,1-trifluoro-2-propanol;

(2R)-3-[[3-(5,6,7,8-tetrahydro-2-naphthoxy)phenyl][[3-(heptafluoropropyl)phenyl]-methyl]amino]-1,1,1-trifluoro-2-propanol;

(2R)-3-[[3-(phenoxy)phenyl][[3-(heptafluoropropyl) phenyl]methyl]amino]-1,1,1-trifluoro-2-propanol;

(2R)-3-[[3-[3-(N,N-dimethylamino)phenoxy]phenyl][[3-(heptafluoropropyl)phenyl]-methyl]amino]-1,1,1-trifluoro-2-propanol;

(2R)-3-[[[3-(heptafluoropropyl)phenyl]methyl][3-[[3-(trifluoromethoxy)phenyl]-methoxy]phenyl]amino]-1,1,1-trifluoro-2-propanol;

(2R)-3-[[[3-(heptafluoropropyl)phenyl]methyl][3-[[3-(trifluoromethyl)phenyl]-methoxy]phenyl]amino]-1,1,1-trifluoro-2-propanol;

(2R)-3-[[[3-(heptafluoropropyl)phenyl]methyl][3-[[3,5-dimethylphenyl]methoxy]-phenyl]amino]-1,1,1-trifluoro-2-propanol;

(2R)-3-[[[3-(heptafluoropropyl)phenyl]methyl][3-[[3-(trifluoromethylthio)phenyl]-methoxy]phenyl]amino]-1,1,1-trifluoro-2-propanol;

(2R)-3-[[[3-(heptafluoropropyl)phenyl]methyl][3-[[3,5-difluorophenyl]methoxy]-phenyl]amino]-1,1,1-trifluoro-2-propanol;

(2R)-3-[[[3-(heptafluoropropyl)phenyl]methyl][3-[cyclohexylmethoxy]phenyl]-amino]-1,1,1-trifluoro-2-propanol;

(2R)-3-[[3-(2-difluoromethoxy-4-pyridyloxy)phenyl][[3-(heptafluoropropyl)phenyl]-methyl]amino]-1,1,1-trifluoro-2-propanol;

(2R)-3-[[3-(2-trifluoromethyl-4-pyridyloxy)phenyl][[3-(heptafluoropropyl)phenyl]-methyl]amino]-1,1,1-trifluoro-2-propanol;

(2R)-3-[[3-(3-difluoromethoxyphenoxy)phenyl][[3-(heptafluoropropyl)phenyl]-methyl]amino]-1,1,1-trifluoro-2-propanol;

(2R)-3-[[[3-(3-trifluoromethylthio)phenoxy]phenyl][[3-(heptafluoropropyl)phenyl]-methyl]amino]-1,1,1-trifluoro-2-propanol;

(2R)-3-[[3-(4-chloro-3-trifluoromethylphenoxy)phenyl][[3-(heptafluoropropyl)-phenyl]methyl]amino]-1,1,1-trifluoro-2-propanol;

(2R)-3-[[3-(3-trifluoromethoxyphenoxy)phenyl][[2-fluoro-5-(trifluoromethyl)phenyl]methyl]amino]-1,1,1-trifluoro-2-propanol;

(2R)-3-[[3-(3-isopropylphenoxy)phenyl][[2-fluoro-5-(trifluoromethyl)phenyl]-methyl]amino]-1,1,1-trifluoro-2-propanol;

(2R)-3-[[3-(3-cyclopropylphenoxy)phenyl][[2-fluoro-5-(trifluoromethyl)phenyl]-methyl]amino]-1,1,1-trifluoro-2-propanol;

(2R)-3-[[3-(3-(2-furyl)phenoxy)phenyl][[2-fluoro-5-(trifluoromethyl)phenyl]-methyl]amino]-1,1,1-trifluoro-2-propanol;

(2R)-3-[[3-(2,3-dichlorophenoxy)phenyl][[2-fluoro-5-(trifluoromethyl)phenyl]-methyl]amino]-1,1,1-trifluoro-2-propanol;

(2R)-3-[[3-(4-fluorophenoxy)phenyl][[2-fluoro-5-(trifluoromethyl)phenyl]-methyl]amino]-1,1,1-trifluoro-3-propanol;

(2R)-3-[[3-(4-methylphenoxy)phenyl][[2-fluoro-5-(trifluoromethyl)phenyl]-methyl]amino]-1,1,1-trifluoro-2-propanol;

(2R)-3-[[3-(2-fluoro-5-bromophenoxy)phenyl][[2-fluoro-5-(trifluoromethyl)phenyl]methyl]amino]-1,1,1-trifluoro-2-propanol;

(2R)-3-[[3-(4-chloro-3-ethylphenoxy)phenyl][[2-fluoro-5-(trifluoromethyl)phenyl]methyl]amino]-1,1,1-trifluoro-2-propanol;

(2R)-3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;

(2R)-3-[[3-[3-(pentafluoroethoxy)phenoxy]phenyl][[2-fluoro-5-(trifluoromethyl)phenyl]methyl]amino]-1,1,1-trifluoro-2-propanol;

(2R)-3-[[3-(3,5-dimethylphenoxy)phenyl][[2-fluoro-5-(trifluoromethyl)phenyl]-methyl]amino]-1,1,1-trifluoro-2-propanol;

(2R)-3-[[3-(3-ethylphenoxy)phenyl][[2-fluoro-5-(trifluoromethyl)phenyl]methyl]-amino]-1,1,1-trifluoro-2-propanol;

(2R)-3-[[3-(3-t-butylphenoxy)phenyl][[2-fluoro-5-(trifluoromethyl)phenyl]methyl]-amino]-1,1,1-trifluoro-2-propanol;

(2R)-3-[[3-(3-methylphenoxy)phenyl][[2-fluoro-5-(trifluoromethyl)phenyl]methyl]-amino]-1,1,1-trifluoro-2-propanol;

(2R)-3-[[3-(5,6,7,8-tetrahydro-2-naphthoxy)phenyl][[2-fluoro-5-(trifluoromethyl)-phenyl]methyl]amino]-1,1,1-trifluoro-2-propanol;

(2R)-3-[[3-(phenoxy)phenyl][[2-fluoro-5-(trifluoromethyl) phenyl]methyl]amino]-1,1,1-trifluoro-2-propanol;

(2R)-3-[[3-[3-(N,N-dimethylamino,phenoxy]phenyl][[2-fluoro-5-(trifluoromethyl)-phenyl]methyl]amino]-1,1,1-trifluoro-2-propanol;

(2R)-3-[[[2-fluoro-5-(trifluoromethyl)phenyl]methyl][3-[[3-(trifluoromethoxy)-phenyl]methoxy]phenyl]amino]-1,1,1-trifluoro-3-propanol;

(2R)-3-[[[2-fluoro-5-(trifluoromethyl)phenyl]methyl][3-[[3-(trifluoromethyl)-phenyl]methoxy]phenyl]amino]-1,1,1-trifluoro-2-propanol;

(2R)-3-[[[2-fluoro-5-(trifluoromethyl)phenyl]methyl][3-[[3,5-dimethylphenyl]-methoxy]phenyl]amino]-1,1,1-trifluoro-2-propanol;

(2R)-3-[[[2-fluoro-5-(trifluoromethyl)phenyl]methyl][3-[[3-(trifluoromethylthio)phenyl]methoxy]phenyl]amino]-1,1,1-trifluoro-2-propanol;

(2R)-3-[[[2-fluoro-5-(trifluoromethyl)phenyl]methyl][3-[[3,5-difluorophenyl]-methoxy]phenyl]amino]-1,1,1-trifluoro-2-propanol;

(2R)-3-[[[2-fluoro-5-(trifluoromethyl)phenyl]methyl][3-[cyclohexylmethoxyl-phenyl]amino]-1,1,1-trifluoro-2-propanol;

(2R)-3-[[3-(2-difluoromethoxy-4-pyridyloxy)phenyl][[2-fluoro-5-(trifluoromethyl)-phenyl]methyl]amino]-1,1,1-trifluoro-2-propanol;
(2R)-3-[[3-(2-trifluoromethyl-4-pyridyloxy)phenyl][[2-fluoro-5-(trifluoromethyl)phenyl]methyl]amino]-1,1,1-trifluoro-2-propanol;
(2R)-3-[[3-(3-difluoromethoxyphenoxy)phenyl][[2-fluoro-5-(trifluoromethyl)phenyl]methyl]amino]-1,1,1-trifluoro-2-propanol;
(2R)-3-[[[3-(3-trifluoromethylthio)phenoxy]phenyl][[2-fluoro-5-(trifluoromethyl)-phenyl]methyl]amino]-1,1,1-trifluoro-2-propanol;
(2R)-3-[[3-(4-chloro-3-trifluoromethylphenoxy)phenyl][[2-fluoro-5-(trifluoromethyl)phenyl]methyl]amino]-1,1,1-trifluoro-2-propanol;
(2R)-3-[[3-(3-trifluoromethoxyphenoxy)phenyl][[2-fluoro-4-(trifluoromethyl)phenyl]methyl]amino]-1,1,1-trifluoro-2-propanol;
(2R)-3-[[3-(3-isopropylphenoxy)phenyl][[2-fluoro-4-(trifluoromethyl)phenyl]-methyl]amino]1-1,1,1-trifluoro-2-propanol;
(2R)-3-[[3-(3-cyclopropylphenoxy)phenyl][[2-flouro-4-(trifluoromethyl)phenyl]-methyl]amino]-1,1,1-trifluoro-2-propanol;
(2R)-3-[[3-(3-(2-furyl)phenoxy)phenyl][[2-fluoro-4-(trifluoromethyl)phenyl]-methyl]amino]-1,1,1-trifluoro-2-propanol;
(2R)-3-[[3-(2,3-dichlorophenoxy)phenyl][[2-fluoro-4-(trifluoromethyl)phenyl]-methyl]amino]-1,1,1-trifluoro-2-propanol;
(2R)-3-[[3-(4-fluorophenoxy)phenyl][[2-fluoro-4-(trifluoromethyl)phenyl]-methyl]amino]-1,1,1-trifluoro-2-propanol;
(2R)-3-[[3-(4-methylphenoxy)phenyl][[2-fluoro-4-(trifluoromethyl)phenyl]-methyl]amino]-1,1,1-trifluoro-2-propanol;
(2R)-3-[[3-(2-fluoro-5-bromophenoxy)phenyl][[2-fluoro-4-(trifluoromethyl)phenyl]methyl]amino]-1,1,1-trifluoro-2-propanol;
(2R)-3-[[3-(4-chloro-3-ethylphenoxy)phenyl][[2-fluoro-4-(trifluoromethyl)phenyl]methyl]amino]-1,1,1-trifluoro-2-propanol;
(2R)-3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;
(2R)-3-[[3-[3-(pentafluoroethyl)phenoxy]phenyl][[2-fluoro-4-(trifluoromethyl)phenyl]methyl]amino]-1,1,1-trifluoro-2-propanol;
(2R)-3-[[3-(3,5-dimethylphenoxy)phenyl][[2-fluoro-4-(trifluoromethyl)phenyl]-methyl]amino]-1,1,1-trifluoro-2-propanol;
(2R)-3-[[3-(3-ethylphenoxy)phenyl][[2-fluoro-4-(trifluoromethyl)phenyl]methyl]-amino]-1,1,1-trifluoro-2-propanol;
(2R)-3-[[3-(3-t-butylphenoxy)phenyl][[2-fluoro-4-(trifluoromethyl)phenyl]methyl]-amino]-1,1,1-trifluoro-2-propanol;
(2R)-3-[[3-(3-methylphenoxy)phenyl][[2-fluoro-4-(trifluoromethyl)phenyl]methyl]-amino]-1,1,1-trifluoro-2-propanol;
(2R)-3-[[3-(5,6,7,8-tetrahydro-2-naphthoxy)phenyl][[2-fluoro-4-(trifluoromethyl)-phenyl]methyl]amino]-1,1,1-trifluoro-2-propanol;
(2R)-3-[[3-(phenoxy)phenyl][[2-fluoro-4-(trifluoromethyl)phenyl]methyl]amino]-1,1,1-trifluoro-2-propanol;
(2R)-3-[[3-[3-(N,N-dimethylamino)phenoxy]phenyl][[2-fluoro-4-(trifluoromethyl)-phenyl]methyl]amino]-1,1,1-trifluoro-2-propanol;
(2R)-3-[[[2-fluoro-4-(trifluoromethyl)phenyl]methyl][3-[[3-(trifluoromethoxy)phenyl]methoxy]phenyl]amino]-1,1,1-trifluoro-2-propanol;
(3R)-3-[[[2-fluoro-4-(trifluoromethyl)phenyl]methyl][3-[[3-(trifluoromethyl)phenyl]methoxy]phenyl]amino]-1,1,1-trifluoro-2-propanol;
(2R)-3-[[[2-fluoro-4-(trifluoromethyl)phenyl]methyl][3-[[3,5-dimethylphenyl]-methoxy]phenyl]amino]-1,1,1-trifluoro-2-propanol;
(2R)-3-[[[2-fluoro-4-(trifluoromethyl)phenyl]methyl][3-[[3-(trifluoromethylthio)-phenyl]methoxy]phenyl]amino]-1,1,1-trifluoro-2-propanol;
(2R)-3-[[[2-fluoro-4-(trifluoromethyl)phenyl]methyl][3-[[3,5-difluorophenyl]-methoxy]phenyl]amino]-1,1,1-trifluoro-2-propanol;
(2R)-3-[[[2-fluoro-4-(trifluoromethyl)phenyl]methyl][3-[cyclohexylmethoxy]-phenyl]amino]-1,1,1-trifluoro-2-propanol;
(2R)-3-[[3-(2-difluoromethoxy-4-pyridyloxy)phenyl][[2-fluoro-4-(trifluoromethyl)-phenyl]methyl]amino]-1,1,1-trifluoro-2-propanol;
(2R)-3-[[3-(2-trifluoromethyl-4-pyridyloxy)phenyl][[2-fluoro-4-(trifluoromethyl)phenyl]methyl]amino]-1,1,1-trifluoro-2-propanol;
(2R)-3-[[3-(3-difluoromethoxyphenoxy)phenyl][[2-fluoro-4-(trifluoromethyl)-phenyl]methyl]amino]-1,1,1-trifluoro-2-propanol;
(2R)-3-[[[3-(3-trifluoromethylthio)phenoxy]phenyl][[2-fluoro-4-(trifluoromethyl)-phenyl]methyl]amino]-1,1,1-trifluoro-2-propanol; and
(2R)-3-[[3-(4-chloro-3-trifluoromethylphenoxy)phenyl][[2-fluoro-4-(trifluoromethyl)phenyl]methyl]amino]-1,1,1-trifluoro-2-propanol.

Another class of CETP inhibitors that finds utility with the present invention consists of quinolines of Formula XVII

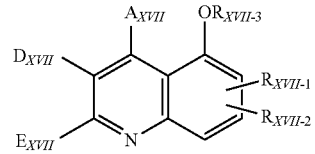

Formula XVII and pharmaceutically acceptable forms thereof, wherein:

$A_{XVII}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$NR_{XVII-4}R_{XVII-5}$ wherein $R_{XVII-4}$ and $R_{XVII-5}$ are identical or different and denote a hydrogen, phenyl or a straight-chain or branched alkyl containing up to 6 carbon atoms, $D_{XVII}$ denotes an aryl containing 6 to 10 carbon atoms, which is optionally substituted with a phenyl, nitro, halogen, trifluoromethyl or trifluoromethoxy, or a radical according to the formula $R_{XVII-6}$—$L_{XVII}$—,

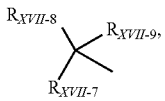

or $R_{XVII-10}-T_{XVII}-V_{XVII}-X_{XVII}-$ wherein $R_{XVII-6}$, $R_{XVII-7}$, $R_{XVII-10}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteroatoms from the series of S, N and/or O, and/or in the form of a group according to the formula $-OR_{XVII-11}$, $-SR_{XVII-12}$, $-SO_2R_{XVII-13}$, or $-NR_{XVII-14}R_{XVII-15}$;

$R_{XVII-11}$, $R_{XVII-12}$, and $R_{XVII-13}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{XVII-14}$ and $R_{XVII-15}$ are identical or different and have the meaning of $R_{XVII-4}$ and $R_{XVII-5}$ given above, or $R_{XVII-6}$ and/or $R_{XVII-7}$ denote a radical according to the formula

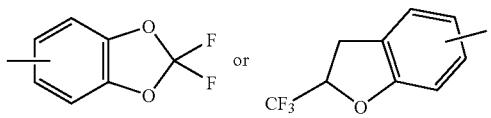

$R_{XVII-8}$ denotes a hydrogen or halogen, and $R_{XVII-9}$ denotes a hydrogen, halogen, azido, trifluoromethyl, hydroxyl, trifluoromethoxy, a straight-chain or branched alkoxy or alkyl containing up to 6 carbon atoms each, or a radical according to the formula $NR_{XVII-16}R_{XVII-17}$, $R_{XVII-16}$ and $R_{XVII-17}$ are identical or different and have the meaning of $R_{XVII-4}$ and $R_{XVII-5}$ above; or $R_{XVII-8}$ and $R_{XVII-9}$ together form a radical according to the formula $=O$ or $=NR_{XVII-18}$;

$R_{XVII-18}$ denotes a hydrogen or a straight-chain or branched alkyl, alkoxy or acyl containing up to 6 carbon atoms each;

$L_{XVII}$ denotes a straight-chain or branched alkylene or alkenylene chain containing up to 8 carbon atoms each, which are optionally substituted with up to two hydroxyl groups;

$T_{XVII}$ and $X_{XVII}$ are identical or different and denote a straight-chain or branched alkylene chain containing up to 8 carbon atoms; or $T_{XVII}$ and $X_{XVII}$ denotes a bond;

$V_{XVII}$ denotes an oxygen or sulfur atom or $-NR_{XVII-19}$;

$R_{XVII-19}$ denotes a hydrogen or a straight-chain or branched alkyl containing up to 6 carbon atoms or a phenyl;

$E_{XVII}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl;

$R_{XVII-1}$ and $R_{XVII-2}$ are identical or different and denote a cycloalkyl containing 3 to 8 carbon atoms, hydrogen, nitro, halogen, trifluoromethyl, trifluoromethoxy, carboxy, hydroxy, cyano, a straight-chain or branched acyl, alkoxycarbonyl or alkoxy with up to 6 carbon atoms, or $NR_{XVII-20}R_{XVII-21}$;

$R_{XVII-20}$ and $R_{XVII-21}$ are identical or different and denote hydrogen, phenyl, or a straight-chain or branched alkyl with up to 6 carbon atoms; and or $R_{XVII-1}$ and/or $R_{XVII-2}$ are straight-chain or branched alkyl with up to 6 carbon atoms, optionally substituted with halogen, trifluoromethoxy, hydroxy, or a straight-chain or branched alkoxy with up to 4 carbon atoms, aryl containing 6-10 carbon atoms optionally substituted with up to five of the same or different substituents selected from halogen, cyano, hydroxy, trifluoromethyl, trifluoromethoxy, nitro, straight-chain or branched alkyl, acyl, hydroxyalkyl, alkoxy with up to 7 carbon atoms and $NR_{XVII-22}R_{XVII-23}$;

$R_{XVII-22}$ and $R_{XVII-23}$ are identical or different and denote hydrogen, phenyl or a straight-chain or branched akyl up to 6 carbon atoms; and/or $R_{XVII-1}$ and $R_{XVII-2}$ taken together form a straight-chain or branched alkene or alkane with up to 6 carbon atoms optionally substituted with halogen, trifluoromethyl, hydroxy or straight-chain or branched alkoxy with up to 5 carbon atoms;

$R_{XVII-3}$ denotes hydrogen, a straight-chain or branched acyl with up to 20 carbon atoms, a benzoyl optionally substituted with halogen, trifluoromethyl, nitro or trifluoromethoxy, a straight-chained or branched fluoroacyl with up to 8 carbon atoms and 7 fluoro atoms, a cycloalkyl with 3 to 7 carbon atoms, a straight chained or branched alkyl with up to 8 carbon atoms optionally substituted with hydroxyl, a straight-chained or branched alkoxy with up to 6 carbon atoms optionally substituted with phenyl which may in turn be substituted with halogen, nitro, trifluoromethyl, trifluoromethoxy, or phenyl or a tetrazol substitued phenyl, and/or an alkyl that is optionally substituted with a group according to the formula $-OR_{XVII-24}$;

$R_{XVII-24}$ is a straight-chained or branched acyl with up to 4 carbon atoms or benzyl.

Compounds of Formula XVII and their methods of manufacture are disclosed in PCT Publication No. WO 98/39299, which is incorporated herein by reference in its entirety for all purposes.

Another class of CETP inhibitors that finds utility with the present invention consists of 4-Phenyltetrahydroquinolines of Formula XVIII

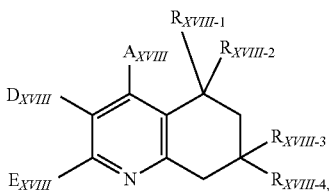

Formula XVIII

N oxides thereof, and pharmaceutically acceptable forms thereof, wherein:

$A_{XVIII}$ denotes a phenyl optionally substituted with up to two identical or different substituents in the form of halogen, trifluoromethyl or a straight-chain or branched alkyl or alkoxy containing up to three carbon atoms;

$D_{XVIII}$ denotes the formula

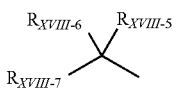

or $R_{XVIII-8}$—$CH_2$—O—$CH_2$—;

$R_{XVIII-5}$ and $R_{XVIII-6}$ are taken together to form =O; or $R_{XVIII-5}$ denotes hydrogen and $R_{XVIII-6}$ denotes halogen or hydrogen; or $R_{XVIII-5}$ and $R_{XVIII-6}$ denote hydrogen;

$R_{XVIII-7}$ and $R_{XVIII-8}$ are identical or different and denote phenyl, naphthyl, benzothiazolyl, quinolinyl, pyrimidyl or pyridyl with up to four identical or different substituents in the form of halogen, trifluoromethyl, nitro, cyano, trifluoromethoxy, —$SO_2$—$CH_3$ or $NR_{XVIII-9}R_{XVIII-10}$;

$R_{XVIII-9}$ and $R_{XVIII-10}$ are identical or different and denote hydrogen or a straight-chained or branched alkyl of up to three carbon atoms;

$E_{XVIII}$ denotes a cycloalkyl of from three to six carbon atoms or a straight-chained or branched alkyl of up to eight carbon atoms;

$R_{XVIII-1}$ denotes hydroxy;

$R_{XVIII-2}$ denotes hydrogen or methyl;

$R_{XVIII-3}$ and $R_{XVIII-4}$ are identical or different and denote straight-chained or branched alkyl of up to three carbon atoms; or $R_{XVIII-3}$ and $R_{XVIII-4}$ taken together form an alkenylene made up of between two and four carbon atoms.

Compounds of Formula XVIII and their methods of manufacture are disclosed in PCT Publication No. WO 99/15504 and U.S. Pat. No. 6,291,477, both of which are incorporated herein by reference in their entireties for all purposes.

Another class of drugs that may be utilized in the present invention include low-solubility drugs such as CCR1 inhibitors. CCR1 inhibitors includes quinoxaline-2-carboxylic acid [4(R)-carbamoyl-1(S)-3-fluorobenzyl-2(S),7-dihydroxy-7-methyl-octyl]amide and quinoxaline-2-carboxylic acid [1-benzyl-4-(4,4-difluoro-1-hydroxycyclohexyl)-2-hydroxy-4-hydroxycarbamoyl-butyl]-amide.

The invention is useful for improving the intrinsic dissolution rate of compounds selected from the following. The intrinsic dissolution rate is defined as the rate of dissolution of a pure pharmaceutical active ingredient when conditions such as surface area, agitation-stirring speed, pH and ionic-strength of the dissolution medium are kept constant. Intrinsic dissolution rate is further defined as being measured in water at 37° C. using a USP II dissolution apparatus equipped with a Wood's apparatus (Wood, J H; Syarto, J E and Lefterman, H: J.Pharm. Sci. 54 (1965), 1068) with a stirring speed of 50 rpm. The intrinsic dissolution rate is defined in terms of mg of drug dissolved per minute from a unit surface area, therefore, the intrinsic dissolution rate is referred to in units of mg/min.cm².

The compositions and methods of the invention are particularly useful for compounds with an intrinsic dissolution rate of preferably less than 0.1 mg/min.cm² and more preferably with less than 0.05 mg/min.cm².

Turning now to the chemical structures of specific CCR1 inhibitors, one class of CCR1 inhibitors that finds utility with the present invention consists of dihydroxyhexanoic acid derivatives having the Formula CCR1-I

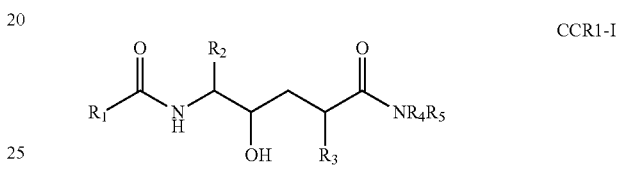

CCR1-I wherein $R_1$ is ($C_2$-$C_9$) heteroaryl optionally substituted with one, two or three substituents independently selected from the group consisting of hydrogen, halo, cyano, ($C_1$-$C_6$)alkyl optionally substituted with one, two or three fluorine atoms, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]₂amino, amino($C_1$-$C_6$)alkyl, ($C_1$-$C_6$)alkylamino($C_1$-$C_6$)alkyl, [($C_1$-$C_6$)alkyl]₂amino($C_1$-$C_6$)alkyl, $H_2N$—(C=O)—, ($C_1$-$C_6$)alkyl-NH—(C=O)—, [($C_1$-$C_6$)alkyl]₂N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]₂N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]₂N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl;

wherein $R_2$ is phenyl-($CH_2$)$_m$—, naphthyl-($CH_2$)$_m$—, ($C_3$-$C_{10}$)cycloalkyl-($CH_2$)$_m$—, ($C_1$-$C_6$)alkyl or ($C_2$-$C_9$)heteroaryl-($CH_2$)$_m$—, wherein each of said phenyl, naphthyl, ($C_3$-$C_{10}$)cycloalkyl or ($C_2$-$C_9$)heteroaryl moieties of said phenyl-($CH_2$)$_m$—, naphthyl-($CH_2$)$_m$—, ($C_3$-$C_{10}$)cycloalkyl-($CH_2$)$_m$— or ($C_2$-$C_9$)heteroaryl-($CH_2$)$_m$— groups may optionally be substituted with one, two, or three substituents independently selected from the group consisting of hydrogen, halo, cyano, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)

alkyl-(C=O)—O—, $(C_1-C_6)$alkyl-(C=O)—O—$(C_1$-$C_6)$alkyl, H(O=C)—, H(O=C)—$(C_1-C_6)$alkyl, $(C_1$-$C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-H N(C=O)—$(C_1-C_6)$alkyl, $[(C_1-C_6)$alkyl$]_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, phenoxy, benzyloxy, $(C_3-C_{10})$cycloalkyl, $(C_2-C_9)$heterocycloalkyl, and $(C_2-C_9)$heteroaryl;

wherein $R^3$ is hydrogen, $(C_1-C_{10})$alkyl, $(C_3-C_{10})$cycloalkyl-$(CH_2)_n$—, $(C_2-C_9)$heterocycloalkyl-$(CH_2)_n$—, $(C_2-C_9)$heteroaryl-$(CH_2)_n$— or aryl-$(CH_2)_n$—; wherein n is an interger from zero to six;

wherein said $R_3$ $(C_1-C_{10})$alkyl group may optionally be substituted with one or more substituents, (preferably from one to three substituents) independently selected from hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-H N(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2$N—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl; and wherein any of the carbon-carbon single bonds of said $(C_1-C_{10})$alkyl may optionally be replaced by a carbon-carbon double bond;

wherein the $(C_3-C_{10})$cycloalkyl moiety of said $R_3$ $(C_3-C_{10})$cycloalkyl-$(CH_2)_n$— group may optionally be substituted by one to three substituents independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkyl HN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

wherein the $(C_2-C_9)$heterocycloalkyl moiety of said $R_3$ $(C_2-C_9)$heterocycloalkyl-$(CH_2)_n$— group may contain from one to three heteroatoms independently selected from nitrogen, sulfur, oxygen, >S(=O), >$SO_2$ or >$NR^6$, wherein said $(C_2-C_9)$heterocycloalkyl moiety of said $(C_2-C_9)$heterocycloalkyl-$(CH_2)_n$— group may optionally be substituted on any of the ring carbon atoms capable of forming an additional bond (preferably one to three substitutents per ring) with a substituent independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

wherein the $(C_2-C_9)$heteroaryl moiety of said $R^3$ $(C_2-C_9)$heteroaryl-$(CH_2)_n$— group may contain from one to three heteroatoms independently selected from nitrogen, sulfur or oxygen, wherein said $(C_2-C_9)$heteroaryl moiety of said $(C_2-C_9)$heteroaryl-$(CH_2)_n$— group may optionally be substituted on any of the ring carbon atoms capable of forming an additional bond (preferably one to three substitutents per ring) with a substituent selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—

NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl; and wherein said aryl moiety of said R$_3$ aryl-(CH$_2$)$_n$— group is optionally substituted phenyl or naphthyl, wherein said phenyl and naphthyl may optionally be substituted with from one to three substituents independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

or R$_3$ and the carbon to which it is attached form a five to seven membered carbocyclic ring, wherein any of the carbon atoms of said five membered carbocyclic ring may optionally be substituted with a substituent selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl; wherein one of the carbon-carbon bonds of said five to seven membered carbocyclic ring may optionally be fused to an optionally substituted phenyl ring, wherein said substitutents may be independently selected from hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

wherein R$_4$ is hydrogen, $(C_1-C_6)$alkyl, hydroxy, $(C_1-C_6)$alkoxy, hydroxy$(C_1-C_6)$alkyl, $(C_1-C_6)$alkoxy(C=O)—, $(C_3-C_{10})$cycloalkyl-(CH$_2$)$_q$—, $(C_2-C_9)$heterocycloalkyl-(CH$_2$)$_q$—, $(C_2-C_9)$heteroaryl-(CH$_2$)$_q$—, phenyl-(CH$_2$)$_q$—, or naphthyl-(CH$_2$)$_q$—; wherein said $(C_2-C_9)$heterocycloalkyl, $(C_2-C_9)$heteroaryl, phenyl and naphthyl groups may be optionally substituted with one or two substituents from the group consisting of hydrogen, halo, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$ alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$amino, amino$(C_1-C_6)$alkyl, $(C_1-C_6)$alkylamino $(C_1-C_6)$alkyl, [$(C_1-C_6)$alkyl]$_2$amino $(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$, phenyl, $(C_3-C_{10})$cycloalkyl, $(C_2-C_9)$heterocycloalkyl, and $(C_2-C_9)$heteroaryl;

wherein R$_5$ is hydrogen, $(C_1-C_6)$alkyl or amino; or

R$_4$ and R$_5$ together with the nitrogen atom to which they are attached form a $(C_2-C_9)$heterocycloalkyl group optionally substituted with one or two substituents selected from the group consisting of hydrogen, halo, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, (C₁-C₆) alkyl(O=C)—, (C₁-C₆)alkyl(O=C)—(C₁-C₆) alkyl, NO₂, amino, (C₁-C₆)alkylamino, [(C₁-C₆)alkyl]₂ amino, amino(C₁-C₆)alkyl, (C₁-C₆)alkylamino (C₁-C₆) alkyl, [(C₁-C₆)alkyl]₂amino(C₁-C₆)alkyl, H₂N—(C=O)—, (C₁-C₆)alkyl-NH—(C=O)—, [(C₁-C₆) alkyl]₂N—(C=O)—, H₂N(C=O)—(C₁-C₆)alkyl, (C₁-C₆)alkyl-HN(C=O)—(C₁-C₆)alkyl, [(C₁-C₆)alkyl]₂ N—(C=O)—(C₁-C₆)alkyl, H(O=C)—NH—, (C₁-C₆)alkyl(C=O)—NH, (C₁-C₆)alkyl(C=O)—[NH] (C₁-C₆)alkyl, (C₁-C₆)alkyl(C=O)—[N(C₁-C₆)alkyl] (C₁-C₆)alkyl, (C₁-C₆)alkyl-S—, (C₁-C₆)alkyl-(S=O)—, (C₁-C₆)alkyl-SO₂—, (C₁-C₆)alkyl-SO₂—NH—, H₂N—SO₂—, H₂N—SO₂—(C₁-C₆)alkyl, (C₁-C₆)alkylHN—SO₂—(C₁-C₆)alkyl, [(C₁-C₆)alkyl]₂N—SO₂—(C₁-C₆)alkyl, CF₃SO₃—, (C₁-C₆)alkyl-SO₃—, phenyl, (C₃-C₁₀)cycloalkyl, (C₂-C₉)heterocycloalkyl, and (C₂-C₉)heteroaryl;

wherein R⁶ is hydrogen, (C₁-C₆)alkyl, (C₁-C₆)alkoxy-(CH₂)ɡ—, (C₁-C₆)alkoxy(C=O)—(CH₂)₉—, (C₁-C₆) alkyl-(SO₂)—(CH₂)ɡ—, (C₆-C₁₀)aryloxy-(CH₂)ɡ—, (C₆-C₁₀)aryloxy(C=O)—(CH₂)₉—, or (C₆-C₁₀)aryl-(SO₂)—(CH₂)ɡ—;

wherein g is an integer from zero to four;
wherein m is an integer from zero to four;
wherein n is an interger from zero to six;

with the proviso that when one of R⁴ or R⁵ is hydrogen, and the other of R⁴ or R⁵ is (C₁-C₆)alkyl; R² is (C₃-C₁₀)cycloalkyl or isopropyl and R³ is (C₃-C₅)alkyl, phenyl, methylvinyl, dimethylvinyl, halovinyl, hydroxy(C₁-C₃)alkyl or amino(C₁-C₄)alkyl then R¹ must be other than indol-5-yl, 6-azaindol-2-yl, 2,3-dichloro-pyrrol-5-yl, 4-hydroxyquinolin-3-yl, 2-hydroxyquinoxalin-3-yl, 6-azaindolin-3-yl, or optionally substituted indol-2 or 3-yl;

and the pharmaceutically acceptable salts of such compounds.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Such alkyl and alkoxy groups may be substituted with one, two or three halogen and/or hydroxy atoms, preferably fluorine atoms.

Unless otherwise indicated, "halogen" includes fluorine, chlorine, bromine, and iodine.

"(C₃-C₁₀)cycloalkyl" when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl, and the like.

"(C₂-C₉)heterocycloalkyl" when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, and the like. One of ordinary skill in the art will understand that the connection of said (C₂-C₉)heterocycloalkyl rings is through a carbon or a sp³ hybridized nitrogen heteroatom.

"(C₂-C₉)heteroaryl" when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, and the like. One of ordinary skill in the art will understand that the connection of said (C₂-C₉)heterocycloalkyl rings is through a carbon atom or a sp³ hybridized nitrogen heteroatom.

"Aryl" when used herein refers to phenyl or naphthyl.

"Protected amine" and "protected amino" refers to an amine group with one of the hydrogen atoms replaced with a protecting group (P). Any suitable protecting group may be used for amine protection. Suitable protecting groups include carbobenzyloxy, t-butoxy carbonyl (BOC) or 9-fluorenylmethylenoxy carbonyl.

Compounds of Formula CCR1-I and their methods of manufacture are disclosed in commonly assigned U.S. patent application Ser. No. 09/380,269, filed Feb. 5, 1998, U.S. patent application Ser. No. 09/403,218, filed Jan. 18, 1999, PCT Publication No. WO98/38167, and PCT Publication No. WO99/40061, all of which are incorporated herein by reference in their entireties for all purposes.

In a preferred embodiment, the CCR1 inhibitor is selected from one of the following compounds of Formula CCR1-I:

quinoxaline-2-carboxylic acid 4(R)-carbamoyl-1(S)-(3-chloro-benzyl)-2(S),7-dihydroxy-7-methyl-octyl]-amide;

7,8-difluoro-quinoline-3-carboxylic acid (1S)-benzyl-4(R)-carbamoyl-2(S),7-dihydroxy-7-methyl-octyl)-amide;

6,7,8-trifluoro-quinoline-3-carboxylic acid (1(S)-benzyl-4(R)-carbamoyl-2(S),7-dihydroxy-7-methyl-octyl)-amide;

quinoxaline-2-carboxylic acid [4(R)-carbamoyl-1(S)-(3-fluoro-benzyl)-2(S),7-dihydroxy-7-methyl-octyl]-amide;

quinoxaline-2-carboxylic acid (1(S)-benzyl-2(S),7-dihydroxy-4(R)-hydroxycarbamoyl-7-methyl-octyl)-amide;

quinoxaline-2-carboxylic acid [4(R)-carbamoyl-1(S)-(2-chloro-benzyl)-2(S),7-dihydroxy-7-methyl-octyl]-amide;

quinoxaline-2-carboxylic acid [1(S)-(2-fluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(2-fluoro-benzyl)-2(S),7-dihydroxy-7-methyl-octyl]-amide;

quinoxaline-2-carboxylic acid [1(S)-(3,4-difluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(3,4-difluoro-benzyl)-2(S),7-dihydroxy-7-methyl-octyl]-amide;

quinoxaline-2-carboxylic acid (4(R)-carbamoyl-2(S),7-dihydroxy-7-methyl-1(S)-naphthalen-1-ylmethyl-octyl)-amide;

7,8-difluoro-quinoline-3-carboxylic acid 1(S)-benzyl-2(S)-hydroxy-7-methyl-4(R)-methylcarbamoyl-octyl)-amide;

8-fluoro-quinoline-3-carboxylic acid 1(S)-benzyl-2(S)-hydroxy-7-methyl-4(R)-methylcarbamoyl-octyl)-amide;

quinoxaline-2-carboxylic acid [4(R)-carbamoyl-7-fluoro-1-(3(S)-fluoro-benzyl)-2(S)-hydroxy-7-methyl-octyl]-amide;

quinoxaline-2-carboxylic acid [4(R)-carbamoyl-1-(2(S)-fluoro-benzyl)-2(S)-hydroxy-7-methyl-octyl]-amide;

quinoxaline-2-carboxylic acid [1(S)-benzyl-4(S)-carbamoyl-4(S)-(2,6-dimethyl-tetrahydro-pyran-4-yl)-2(S)-hydroxy-butyl]-amide;
quinoxaline-2-carboxylic acid 1(S)-benzyl-4(R)-carbamoyl-7-fluoro-2(S)-hydroxy-7-methyl-octyl)-amide;
quinoxaline-2-carboxylic acid 1(S)-benzyl-5-cyclohexyl-2(S)-hydroxy-4(R)-methylcarbamoyl-pentyl)-amide;
quinoxaline-2-carboxylic acid 1(S)-cyclohexylmethyl-2(S)-hydroxy-7-methyl-4(R)-methylcarbamoyl-octyl)-amide;
quinoxaline-2-carboxylic acid [1(S)-benzyl-2(S)-hydroxy-4(S)-hydroxycarbamoyl-4-(1-hydroxy-4-methyl-cyclohexyl)-butyl]-amide;
quinoxaline-2-carboxylic acid [1(S)-benzyl-4(S)-(4,4-difluoro-1-hydroxy-cyclohexyl)-2(S)-hydroxy-4-hydroxycarbamoyl-butyl]-amide;
quinoxaline-2-carboxylic acid [1(S)-benzyl-4(S)-carbamoyl-4(S)-(4,4-difluoro-cyclohexyl)-2(S)-hydroxy-butyl]-amide;
quinoline-3-carboxylic acid (1(S)-benzyl-4(S)-carbamoyl-4-cyclohexyl-2(S)-hydroxy-butyl)-amide;
quinoxaline-2-carboxylic acid (4(R)-carbamoyl-2(S)-hydroxy-7-methyl-1(S)-thiophen-2-ylmethyl-octyl)-amide;
quinoxaline-2-carboxylic acid 1(S)-benzyl-4(R)-carbamoyl-7-chloro-2(S)-hydroxy-oct-6-enyl)-amide;
quinoxaline-2-carboxylic acid 1(S)-benzyl-4(R)-carbamoyl-2(S)-hydroxy-5-phenyl-pentyl)-amide;
N-1(S)-benzyl-4(R)-carbamoyl-7-fluoro-2(S)-hydroxy-7-methyl-octyl)-5,6-dichloro-nicotinamide;
quinoxaline-2-carboxylic acid (4(R)-carbamoyl-2(S)-hydroxy-7-methyl-1(S)-thiazol-4(R)-ylmethyl-octyl)-amide;
benzothiazole-2-carboxylic acid 1(S)-benzyl-4(R)-carbamoyl-7-fluoro-2(S)-hydroxy-7-methyl-octyl)-amide; and
benzofuran-2-carboxylic acid 1(S)-benzyl-4(R)-carbamoyl-7-fluoro-2(S)-hydroxy-7-methyl-octyl)-amide.

In another preferred embodiment, the CCR1 compound has a formula Ia-1:

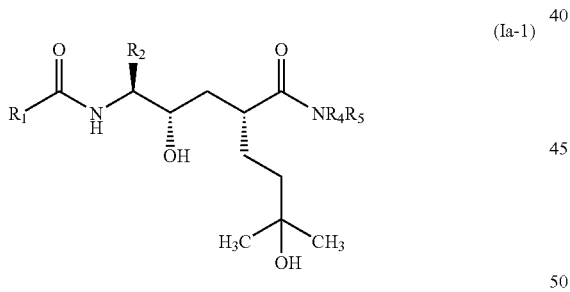

(Ia-1)

wherein the substituents are as defined above.

In a preferred method of making the compound Ia-1, the reaction is started with Scheme 1. In the herein described processes, the substituents are as defined for CCR1-I, and the following:

$R_7$ is hydroxy, $(C_1-C_6)$alkyl, or phenyl wherein the phenyl group unsubstituted or substituted with one, two, or three $(C_1-C_6)$alkyl, hydroxy, or halogen groups;

$R_8$ is hydroxy or halogen;

$R_9$ is phenyl, naphthyl, $(C_3-C_{10})$cycloalkyl, $(C_1-C_6)$alkyl or $(C_2-C_9)$heteroaryl, wherein each of said phenyl, naphthyl, $(C_3-C_{10})$cycloalkyl or $(C_2-C_9)$heteroaryl groups may be unsubstituted or substituted with one, two, or three substituents independently selected from the group consisting of halogen, cyano, and $(C_1-C_6)$alkyl;

P is a protecting group;
X is hydroxy or halogen; and q is 0, 1, 2, 3, or 4.

Scheme 1

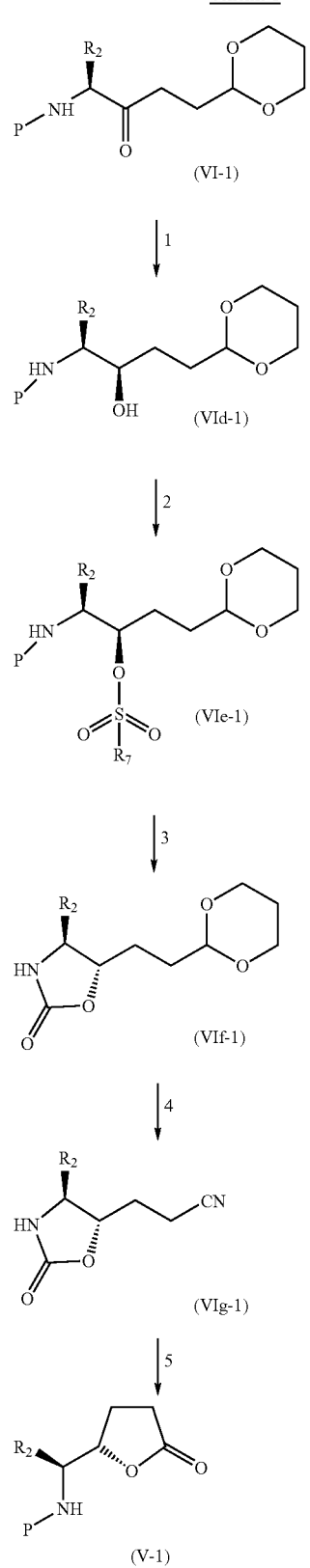

In scheme 1 step 1, a compound of the formula (VI-1) is reduced with a reducing agent under heat to form a compound of the formula (VId-1). In one embodiment, the reducing agent is aluminum triisopropoxide and isopropanol. Preferably, the temperature is maintained above room temperature, more preferably between about 60° C. and about 82° C. The product alcohol can be isolated by either cooling the reaction mixture to room temperature, diluting with more isopropanol and collecting the crystalline material or by cooling the reaction to room temperature and adding 1N HCL and water and collecting the crystalline material.

Step 2 of scheme 1 includes reacting a compound of the formula $R_7$—$SO_2$—X and a compound of the formula (VId-1) in the presence of a base to form the compound of the formula (VIe-1). Any amine base is suitable, including pyridine, triethylamine, N-methylmayholine, and diisoyropylethylamine. In one embodiment, $R_7$—$SO_2$—$R_8$ is p-toluenesulfonic acid, methanesulfonic acid, sulfuric acid, or methanesulfonyl chloride. In another embodiment, the conversion of hydroxy dioxane (VId-1) to dioxane oxazolidinone (VIe-1) can be achieved by treatment of the hydroxy dioxane (VId-1) with methanesulfonyl chloride and triethylamine in tetrahydrofuran solution and heating the mixture to cause the cyclization of the mesylate formed in situ to the oxazolidinone.

In step 3 of scheme 1, a compound of the formula (VIf-1) may be formed by heating the compound of the formula (VIe-1). The reaction may proceed by dissolving compound VIe-1 in a solvent such as pyridine or N-methylimidazole and heating the mixture for several hours at temperature from about 50° C. to about 100° C.; preferably at about 80° C. The mesylate (VIf-1) may be recovered by extraction into an organic solvent-such as ethyl acetate and removal of the amine solvents by extraction of the solution with aqueous acid.

Step 4 of scheme 1 depicts reacting hydroxylamine hydrochloride, a compound of the formula $R_7$—$SO_2$—X, and a compound of the formula (VIf-1) to form a compound of the formula (VIg-1). In one embodiment, $R_7$—$SO_2$—X is p-toluenesulfonic acid, methanesulfonic acid, sulfuric acid, or methanesulfonyl chloride. The reaction may occur in a solvent, such as methanol. In one embodiment, the reaction occurs in methanol with tosic acid at reflux for 8 to 24 hours. The resulting nitrile oxazolidinone contains a small amount of the corresponding ethyl ester which is not removed since it also is converted to the desired lactone in subsequent steps.

Step 5 of scheme 1 includes a) hydrolyzing a compound of the formula (VIg-1) with an aqueous solution in the presence of a base, b) protecting the amine group of the compound so formed, and c) cyclizing the compound so formed with heat and an acid catalyst. In one embodiment, the compound VIg-1 is hydrolyzed with sodium hydroxide. The pH is adjusted to approximately 10 and tetrahydrofuran and BOC dicarbonate are added. This provides the protected hydroxy acid, which may be heated in 10% acetic acid and toluene to provide the protected amine lactone (V-1).

The compound of formula (V-1) may also be produced according to scheme 2.

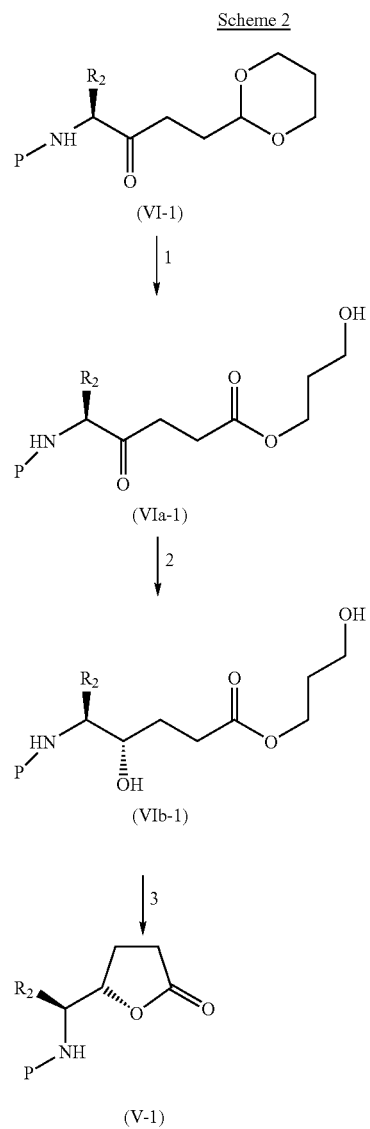

Scheme 2

In step 1 of scheme 2, a compound of the formula (VI-1) may be reacted with ozone to for a compound of the formula (VIa-1). The compound VI-1 may be present in a solvent, such as ethyl acetate, and the ozone introduced through sparging at a temperature below room temperature, preferably at about −15° C., until the starting dioxane ketone is substantially reacted. Any excess ozone may be removed by bubbling nitrogen through the solution. The resulting crude ketone ester mixture may be isolated after treatment with aqueous sodium bisulfite to remove any hydroperoxides.

Alternatively, in step 1 of scheme 2, the compound of the formula (VIa-1) may be formed by reacting hypochlorous acid and a compound of the formula (VI-1). Such an oxidation reaction typically produces chlorinated forms of the compound VIa-1 as side products in addition o the compound VIa-1. This oxidation reaction proceeds by mixing the compound VI-1 in solvent, such as acetic acid and/or acetone, and adding sodium hypochlorite, while keeping the mixture at a low temperature, preferably at or below about 0° C.

As a means to convert the side product chlorinated forms of the compound VIa-1 to compounds of the formula V-1, the compounds formed from the hypochlorous acid oxidation reaction may optionally be hydrogenated by reaction with hydrogen in the presence of a catalyst. The hydrogenation may include introducing the products from the hypochlorous acid oxidation reaction into a solvent system of tetrahydrofuran and water, followed by addition of a Pd/C catalyst. The resulting mixture is subjected to hydrogen above atmospheric pressure and temperature. In one embodiment, the pressure is about 80 pounds per square inch and the temperature is maintained from about 60° C. to about 70° C. until the reaction is substantially complete.

In step 2 of scheme 2, the compound of the formula (VIb-1) may be formed by reacting a silyating agent and a compound of the formula (VIa-1) and reacting the compound so formed with a reducing agent. In one embodiment, the reducing agent is N-selectride. In another emodiment, the silyating agent is 1,1,1,3,3,3-hexamethyl-disilazane. The reduction reaction may occur at temperatures below about 0° C., preferably below about −20° C., more preferably below about −50° C. In addition, the reducing agent may be present in slight excess.

In step 3 of scheme 2, the compound of the formula (V-1) is formed by heating a compound of the formula (VIb-1) in the presence of an acid catalyst, such as acetic acid. In one embodiment, the cyclization reaction occurs by introducing the compound VIb-1 into a solvent mixture, such as toluene and 10% acetic acid, at the solvent reflux temperature for 8 to 16 hours. This provides the desired lactone as a crystalline solid after work up.

One method of making the compound of the formula (VI-1) is by reacting a compound of the formula (VII-1)

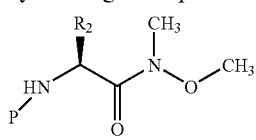

(VII-1)

with a Grinard reagent formed in situ by addition of 2-(2-bromo-ethyl)-[1,3]dioxane to a mixture comprising magnesium and the compound of the formula (VII-1). In one embodiment, the mixture further comprises methyl magnesium chloride and/or methyl magnesium bromide in a solvent. Any exotherm formed from the reaction may be controlled by the rate of addition of the bromide.

The compound of the formula (VII-1) may be formed by coupling N,O-dimethylhydroxylamine hydrochloride and a compound of the formula (VIII-1)

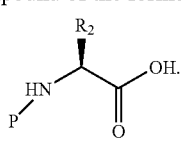

(VIII-1)

This coupling reaction may be performed by mixed anhydride procedure. In one mixed anhydride procedure, compound VIII-1 is combined with methylene chloride and N-methylmorpholine is added followed by isobutyl chloroformate. In a separate mixture, a slurry of N,O-dimethylhydroxylamine hydrochloride is treated with N-methylmorpholine. The two reaction mixtures are combined and then quenched with a solution of citric acid in water. This procedure preferably operates at a temperature below about 20° C., more preferably below about 0° C.

Compounds of formula (V-1) may be used to produce compounds of the formula (IVa1-1) according to scheme 3:

Scheme 3

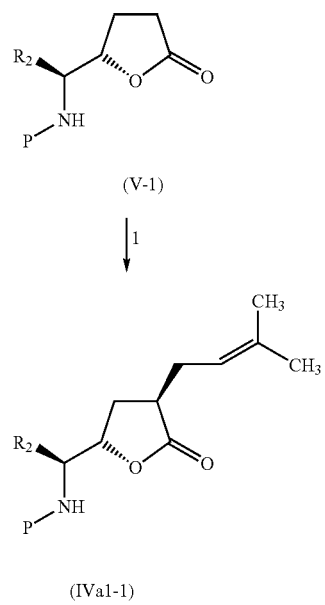

In step 1 of scheme 3, the compound of the formula (IVa1-1) may be formed by reacting 4-halo-2-methyl-2-butene and a compound of the formula (V-1) in the presence of a base. Exemplary bases include lithium dialkyl amides such as lithium N-isopropyl-N-cyclohexylamide, lithium bis(trimethylsilyl)amide, lithium di-isopropylamide, and potassium hydride. Suitable solvents include aprotic polar solvents such as ethers (such as tetrahydrofuran, glyme or dioxane), benzene, or toluene, preferably tetrahydrofuran. The aforesaid reaction is conducted at a temperature from about −78° C. to about 0° C., preferably at about −78° C. In one embodiment, alkylation of the lactone (V-1) is accomplished by reacting the lactone (V-1) with lithium bis(trimethylsilyl)amide and dimethylallyl bromide in tetrahydrofuran at a temperature from about −78° C. to about −50° C. Reaction times range from several hours or if an additive such as dimethylimidazolidinone is present, the reaction may be complete in minutes.

Compounds of formula (IVa1-1) may be used to produce compounds of the formula (Ia-1) according to scheme 4:

Scheme 4

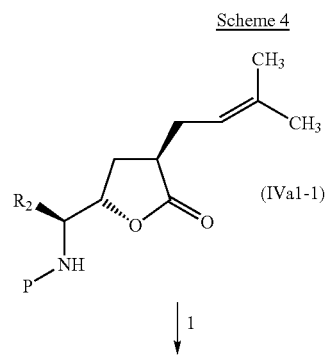

(IVa1-1)

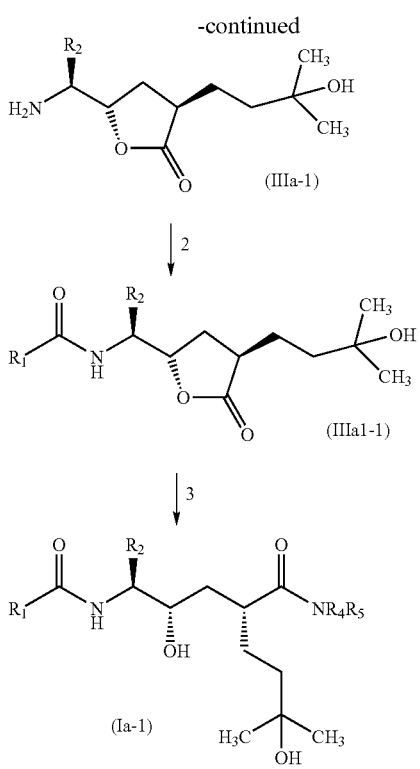

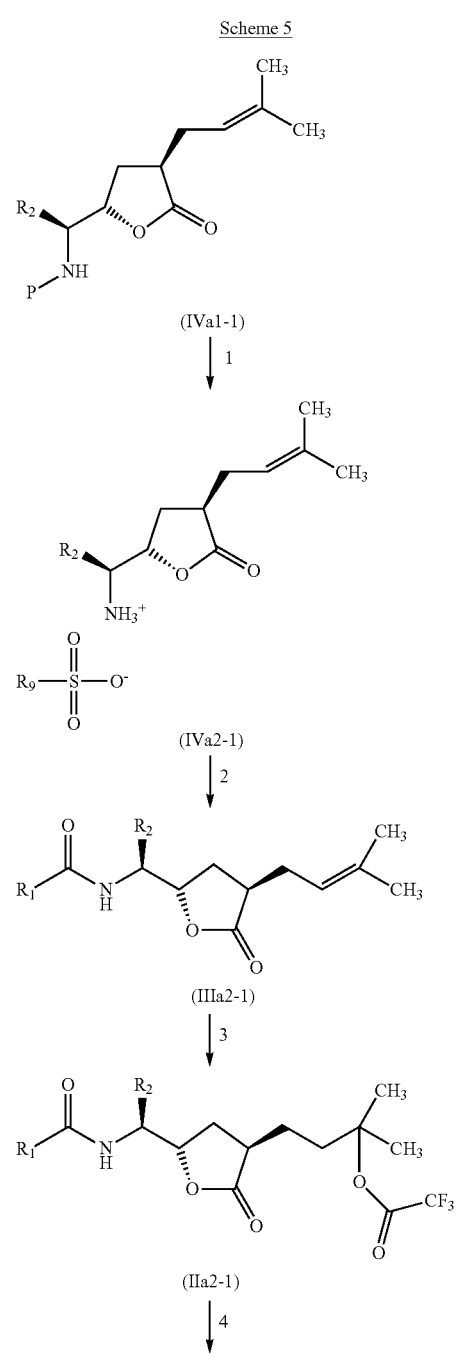

In step 1 of scheme 4, a compound of the formula (IIIa1-1) is formed by reacting a compound of the formula (IVa1-1) with phosphoric acid. Preferably, this reaction occurs in any suitable solvent, such as non-alcoholic solvents. Two preferred solvents include tetrahydrofuran and dichloroethane. The reaction may take place at any suitable temperature, preferably from about −25° C. to about 120° C., more preferably from about 15° C. to about 40° C. Reaction time is dependent on temperature and batch size, amount other factors, but typically reaction time is from about 2 hours to about 14 hours.

Step 2 of scheme 4 depicts coupling a compound IIIa1-1 with a compound having the formula $R_1$—CO—X to form a compound having the formula (IIa1-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI), and diethylphosphorylcyanide. The coupling is conducted in an inert solvent, preferably an aprotic solvent, such as tetrahydrofuran, acetonitirile, dichloromethane, chloroform, or N,N-dimethylformamide. One preferred solvent is tetrahydrofuran. In one embodiment, quinoxaline acid is combined with CDI in anhydrous tetrahydrofuran and heated to provide the acylimidazole. Compound IIIa1-1 is added to the acylimidazole at room temperature to form the compound IIa1-1.

Step 3 of scheme 4 includes reacting the compound of formula IIa1-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa1-1 is dissolved in methanol which has been saturated with ammonia gas. In another embodiment, the compound IIa1-1 in methanol is treated with ammonium hydroxide in tetrahydrofuran at room temperature.

Scheme 5 represents an alternative method to form compounds of formula Ia-1 from compounds of formula IVa1-1.

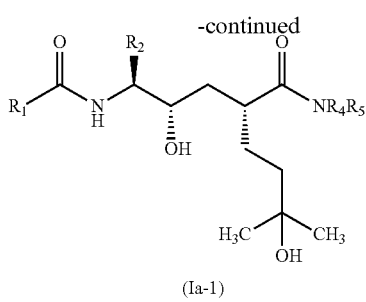

(Ia-1)

In step 1 of scheme 5, a compound of the formula (IVa1-1) is reacted with a compound of the formula R$_9$—SO$_2$—X to form a compound of the formula (IVa2-1). Any suitable acidic deprotection reaction may be performed. In one example, an excess of p-toluenesulfonic acid hydrate in ethyl acetate is introduced to the compound IVa1-1 at room temperature. Suitable solvents include ethyl acetate, alcohols, tetrahydrofuran, and mixtures thereof. The reaction may proceed at ambient or elevated temperatures. Typically, the reaction is substantially complete within two and twelve hours. The resulting compound IVa2-1 may be crystallized and separated from the reaction mixture, and may be further purified to remove impurities by recrystallization from hot ethyl acetate.

In step 2 of scheme 5, the compound IVa2-1 may be coupled with a compound having the formula R$_1$—CO—X to form a compound of the formula (IIIa2-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethoxy-1-ethoxycarbonyl-1,2-dihydroquinoline (EEDQ), carbonyl diimidazole (CDI)/dimethylaminopyridine (DMAP), and diethylphosphorylcyanide. The coupling is conducted in an inert solvent, preferably an aprotic solvent, such as acetonitirile, dichloromethane, chloroform, or N,N-dimethylformamide. One preferred solvent is methylene chloride. In one embodiment, quinoxaline acid is combined with methylene chloride, oxalyl chloride and a catalytic amount of N,N-dimethylformamide to form an acid chloride complex.

The Compound

IVa2-1 is added to the acid chloride complex followed by triethylamine at a temperature from about 0° C. to about 25° C. to form the compound IIIa2-1.

Step 3 of scheme 5 includes reacting a compound IIIa2-1 with trifluoroacetic acid to produce a compound of the formula (IIa2-1). In one embodiment, the hydration with trifluoroacetic acid occurs in methylene chloride solution at room temperature. The hydration may take several hours to complete at room temperature. A catalytic amount of sulfuric acid can be added to the reaction solution to increase the rate of reaction.

Step 4 of scheme 5 includes reacting the compound of formula IIa2-1 with an amine having a formula NHR$_4$R$_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa2-1 is dissolved in methanol which has been saturated with ammonia gas. In another embodiment, the compound IIa2-1 in methanol is treated with ammonium hydroxide in tetrahydrofuran at room temperature.

A particular group of drugs useful in the invention, especially when the drug is in nanoparticulate form, are Danazol, 5α,17α,-1'-(methylsulfonyl)-1'H-pregn-20-yno-[3,2-c]-pyrazol-17-ol, piposulfam, piposulfan, camptothecin, and ethyl-3,5-diacetamido-2,4,6-triiodobenzoate.

Drug in Microparticulate Form

The term "microparticulate form" as employed herein, refer to a solubility-improved form of a drug comprising drug particles generally less than about 10 µm and preferably less than about 5 µm in average particle size, and are generally greater than about 400 nm in average particle size. Such drug in microparticulate form is generally primarily crystalline, but may also contain substantial amounts of amorphous drug. Conventional bulk drug may be converted to microparticulate form by various types of milling and grinding operations. For example, dry milling, wet milling, wet grinding, ball milling, and air jet milling may all be employed to reduce the particle size of bulk crystalline drug. See for example, Lachman et al., *The Theory and Practice of Industrial Pharmacy*, Chapter 2, "Milling" (1986) and U.S. Pat. No. 4,540,602 (Motoyama et al.). In many cases, agglomeration and caking of the drug as it is processed limits the minimum drug particle size that may be obtained. Mixing various excipients such as surfactants, polymers and inorganic powders such as silicon dioxide prior to or during the milling or grinding steps have been shown to aid in obtaining small particle sizes.

It is well known that reduction in the particle size of crystalline drug can increase the rate and extent of drug dissolution. Such microparticulate drug forms often show enhanced bioavailability relative to larger particle size drug forms. This enhanced bioavailability is thought to be a direct consequence of the increased dissolution rate of the drug, as well as, in some cases, the attainment of a higher level of dissolved drug.

The addition of concentration-enhancing polymer to the crystalline drug prior to such grinding and milling steps or following such grinding and milling steps may further enhance the rate of drug dissolution. It may also increase the maximum concentration of dissolved drug attained or it may also increase the length of time that the concentration of dissolved drug remains high.

Drug in Nanoparticulate Form

The terms "nanoparticulate," and "nanoparticulate form" as employed herein refer to a solubility-improved form of a drug in the form of particles generally having an effective average particle size of less than about 1 um, preferably less than about 400 nm, more preferably less than about 250 nm and even more preferably less than about 100 nm. Examples of such nanoparticulate forms of drug are further described in U.S. Pat. No. 5,145,684.

Such nanoparticulate drug form generally comprises about 10% to 99.9% by weight of a crystalline drug substance having a solubility in water less than about 10 mg/mL and the drug substance having an effective average particle size of less than about 400 nm. As described in U.S. Pat. No. 5,145,684, nanoparticulate drug forms preferably consist essentially of 10% to 99.9% by weight of a crystalline drug substance having a solubility in water of less than 10 mg/mL, said drug substance having a non-crosslinked surface modifier adsorbed on the surface thereof in an amount of 0.1 to 90% by weight and sufficient to maintain an effective average particle size of less than about 400 nm.

Particle size can be measured by conventional particle size measuring techniques well known to those skilled in the art, such as sedimentation field flow fractionation, photon correlation spectroscopy, or disk centrifugation. By "an effective average particle size of less than about 400 nm" is meant that at least 90% of the particles have a weight average particle size of less than about 400 nm when measured by the above-noted techniques. Preferred embodiments of the invention will have an effective average particle size of less than about 250 nm. In some embodiments of the invention, the effective average particle size will be less than about 100 nm. In reference to the effective average particle size, it is contemplated that at least 95% and, and more particularly at least 99% of the particles have a particle size that is less than the effective average, e.g., 400 nm.

The nanoparticles of the drug can be prepared in a method comprising the steps of dispersing a drug substance in a liquid dispersion medium and applying mechanical means in the presence of grinding media to reduce the particle size of the drug substance to the effective average particle size. The particles can be reduced in size in the presence of a surface modifier. Alternatively, the particles can be contacted with a surface modifier after attrition.

A general procedure for preparing the nanoparticles is set forth below. The drug substance selected is obtained commercially and/or prepared by techniques known in the art in a conventional coarse form. It is preferred, but not essential, that the particle size of the coarse drug substance selected be less than about 100 µm as determined by sieve analysis. If the coarse particle size of the drug substance is greater than about 100 µm, then it is preferred that the particles of the drug substance be reduced in size to less than 100 µm using a conventional milling method such as airjet or fragmentation milling.

The coarse drug substance selected can then be added to a liquid medium in which it is essentially insoluble to form a premix. The concentration of the drug substance in the liquid medium can vary from about 0.1-60%, and preferably is from 5-30% (w/w). Although not essential, a surface modifier may be present in the premix.

The mixture can be used directly by subjecting it to mechanical means to reduce the average particle size in the drug substance to the desired size. It is preferred that the premix be used directly when a ball mill is used for attrition. Alternatively, the drug can be mixed in the liquid medium using suitable agitation, e.g., a roller mill or a Cowles type mixer, until a homogeneous mixture is observed in which there are no large agglomerates visible to the naked eye. It is preferred that the premix be subjected to such a premilling mixing step when a recirculating media mill is used for attrition.

The mechanical means applied to reduce the particle size of the drug substance conveniently can take the form of a mill. Suitable mills include a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media which are preferably spherical or particulate in form having an average size of less than about 3 mm and, more preferably, less than about 1 mm. Such media desirably can provide the particles of the invention with shorter processing times and impart less wear to the milling equipment. The selection of material for the grinding media is not believed to be critical. Zirconium oxide, such as 95% ZrO stabilized with magnesia, zirconium silicate, and glass grinding media provide particles having levels of contamination which are believed to be acceptable for the preparation of pharmaceutical compositions may be used. However, other media, such as stainless steel, titania, alumina, and 95% ZrO stabilized with yttrium, are expected to be useful. Preferred media have a density greater than about 3 $g/cm^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) may provide the desired results using a high shear media mill.

The particles must be reduced in size at a temperature that does not significantly degrade the drug substance. If desired, the processing equipment can be cooled with conventional cooling equipment. The method is conveniently carried out under conditions of ambient temperature and at processing pressures that are safe and effective for the milling process. For example, ambient processing pressures are typical of ball mills, attritor mills and vibratory mills. Processing pressures up to about 20 psi (1.4 $kg/cm^2$) are typical of media milling.

A surface modifier may be added to the premix or added to the mixture after attrition to aid in maintaining the effective average particle size. Optionally, the mixture can be subjected to a sonication step, e.g., using an ultrasonic power supply. For example, the mixture can be subjected to ultrasonic energy having a frequency of 20-80 kHz for a time of about 1 to 120 seconds.

The concentration-enhancing polymer may be added to the drug before the milling step, or after. Preparation of compositions comprising drug in nanoparticulate form and concentration-enhancing polymers is discussed below.

Another method of forming nanoparticulates, which provide enhanced stability is found in U.S. Pat. No. 5,560,932, incorporated by reference in its entirety. Essentially, the drug form is made in the presence of a surface modifying and colloid stability enhancing surface active agent by the steps of:

1. Dissolving a drug in aqueous base with stirring;
2. Adding above #1 formulation with stirring to a surface active surfactant (or surface modifiers) solution to form a clear solution;
3. Neutralizing above formulation #2 with stirring with an appropriate acid solution. The procedure can be followed by;
4. Removal of formed salt by dialysis or diafiltration; and/or
5. Concentration of dispersion by conventional means.

In general, this process produces stabilized nanoparticulates with effective average particle size having a diameter of less than about 400 nm (as measured by photon correlation spectroscopy) that are stable in particle size upon storage at room temperature or refrigerated conditions. Preferred embodiments have an effective particle size of less than about 250 nm. In some embodiments of the invention, an effective average particle size of less than about 100 nm is even more preferred. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

Yet another method of producing nanoparticulates is found in U.S. Pat. No. 5,874,029, herein incorporated by reference. In this embodiment, a drug/solvent solution is sprayed through a nozzle into an antisolvent. In more detail, the process includes the steps of: (1) introducing a solution (including drug dissolved in a solvent) and a compressed gas (i.e., an energizing gas) into a nozzle; and (2) causing the compressed gas to flow through the nozzle under conditions such that the solution forms a spray of atomized droplets at the nozzle exit. In one embodiment, the solution and compressed gas flow through separate channels of the nozzle. The compressed gas exits the nozzle at a velocity such that the spray is shattered into extremely small droplets at the nozzle exit. The atomized spray of droplets is brought into contact with the antisolvent to cause depletion of the solvent in the atomized spray droplets so that particles are formed from the solute. Contact between the extremely small spray droplets and a turbulent stream of virtually pure antisolvent results in high solvent depletion rates, i.e. high mass-transfer rates, and low probability for droplet coalescence.

Absorbed Drug

Another solubility-improved form of the drug is drug absorbed into a material, (herein after referred to as "absorbed," "absorbed drug" or "absorbed drug form"). An example is drug incorporated into a water-swellable but insoluble cross-linked polymer. An example of such a solubility-improved form is disclosed in U.S. Pat. No. 5,569,469, the disclosure of which is incorporated by reference. One method to manufacture absorbed drug that is incorporated into a crosslinked polymer is implemented in two stages as follows:

1st stage: In the 1st stage the drug is incorporated into a water-swellable but water-insoluble crosslinked polymer (or mixture of two or more such polymers) by any known method such as any of the following:

(1a) the drug is dissolved in a suitable solvent and a certain volume of the solution is sprayed onto a given quantity of polymer with the weight ratio of solution to polymer being chosen on the basis of the polymer swelling capacity and on the basis of the concentration of the drug in the solution. The spraying can be carried out in any apparatus used for the purpose, such as in a continuously stirred reactor, in a rotary evaporator under continuous rotation, in a vacuum granulator under constant mixing, in a mortar under light mixing with a pestle, or in a fluidized bed with the polymer kept suspended in an air stream. The product obtained is then dried in the aforesaid apparatuses or in other suitable apparatuses.

(1b) the drug is dissolved in a suitable solvent and a quantity of a water-swellable but water-insoluble crosslinked polymer (or a mixture of two or more such polymers) is suspended in an excess of the solution obtained. The suspension is kept stirred until the polymer particles swell. The suspension is then filtered or separated by other suitable means and the product is recovered and dried.

(1c) the drug in powder form and the water-swellable but water-insoluble crosslinked polymer (or mixture of two or more such polymers) in powder form are homogeneously mixed together and then ground together in a suitable apparatus such as a ball mill, high-energy vibratory mill, air jet mill etc.

(1d) the drug in powder form and the water-swellable but water-insoluble crosslinked polymer in powder form are mixed homogeneously and then heated together to the drug melting point in an apparatus such as an oven, rotary evaporator, reaction vessel, oil bath etc. until the drug has melted and has been absorbed by the polymer.

The weight ratio of the drug to said polymer (or mixture of two or more polymers) is in all cases between 0.1 and 1000 parts by weight of drug per 100 parts by weight of polymer and preferably between 10 and 100 parts by weight of drug per 100 parts by weight of polymer.

2nd stage: In the 2nd stage the polymer in which the drug has been incorporated by any of the methods described for the 1st stage is brought into contact with a solvent in the vapor or liquid state by any suitable method, for example by any of the following:

(2a) the polymer with the drug incorporated is introduced into a chamber into which the solvent in vapor form is fed through a valve. The chamber can be that in which the 1st stage was carried out;

(2b) the polymer with the drug incorporated is introduced into a sealed chamber already saturated with solvent vapor generated by a solvent container situated within the chamber and kept in the sealed chamber until saturation is complete;

(2c) the polymer with the drug incorporated is suspended in a fluidized bed by an air stream and is then sprayed with the liquid solvent or is exposed to an air stream saturated with the solvent vapor;

(2d) the polymer with the drug incorporated is suspended in an excess of solvent in liquid form, for example in a reaction vessel, in a mixer etc., and is then filtered off or separated by other means.

The time of contact between the polymer with the drug incorporated and the solvent in vapor or liquid form is dependent on the drug/polymer/solvent combination in order to obtain the desired characteristics of high drug concentration in the surface layers and/or transformation of the physical state of the drug into a crystalline state of lower melting point. The treatment with solvent in gaseous form is conducted at a temperature preferably of between 20° and 100° C. and the treatment with solvent in liquid form is conducted at a temperature preferably of between 5° and 90° C. The time of contact with the gaseous solvent is between 0.5 and 48 hours when the solvent is not water, and between 12 and 36 hours when the solvent is water. The time of contact with the liquid solvent is between 1 minute and 96 hours when the solvent is water, and between 1 and 15 hours when the solvent is water. The final drying of the product is preferably conducted in an oven under vacuum at a temperature of between 20° and 100° C.

The solvent (or solvent mixtures) suitable for the method according to the invention are all those which are able to swell the polymer or to be absorbed by the polymer into which the drug has been incorporated. Examples of solvents are water, water-alcohol mixtures, methanol, ethanol, higher alcohols, acetone, chlorinated solvents, formamide, dimethylformamide, fluorinated hydrocarbons and others.

Examples of water-swellable but water-insoluble crosslinked polymers suitable for use (singly or in combinations of two or more than two) in the process of the invention are: crosslinked polyvinylpyrrolidone (abbreviated to crospovidone) as described in National Formulary XV, Supplement 3, page 368; crosslinked sodium carboxymethylcellulose as described in National Formulary XV, Supplement 3, page 367; crosslinked β-cyclodextrin polymer as described in WO patent 83/00809 and by Fenyvest et al. in Pharmacie, 39, 473, 1984; and crosslinked dextran. Other polymers suitable to form the crosslinked polymer should have a hydrophilic polymer lattice allowing high swellability in water, and a water insolubility as determined by the nature of the polymer lattice.

Thus, in one embodiment, the absorbed drug form comprises a poorly soluble drug supported on a polymer substance in a form capable of increasing the dissolving rate of the drug, prepared by a method comprising: 1) bringing a drug incorporated into particles of a crosslinked polymer which is swellable in water but insoluble in water by treating the polymer particles with a solution of the drug in a non-aqueous organic solvent and drying, or by mixing the polymer particles with the drug, heating to the drug melting point, and then cooling at ambient temperature; 2) bringing the thus formed product into contact with a non-aqueous organic solvent, in gaseous or liquid form, which is capable of swelling the polymer, wherein contact with the gaseous solvent is conducted for a period of time of between 0.5 and 48 hours, and wherein contact with the non-aqueous organic liquid solvent is conducted for a period of time of between 1 minute and 96 hours; and 3) drying the product obtained in step 2) under vacuum to produce a drug supported on a polymer substance wherein the drug has been transformed from a metastable amorphous state to a stable high-energy crystalline state and is present in higher concentration in the surface layers of the polymer particles than in their inner layers.

Another embodiment of this drug form can be found in U.S. Pat. No. 4,769,236, herein incorporated by reference. In general, this embodiment is obtained by spray-drying the amorphous form of the drug in the presence of a stabilizer and an agent that inhibits crystal formation. The resulting drug form is absorbed onto a crosslinked polymer to prevent recrystalization.

Other embodiments of the drug form can be found in U.S. Pat. Nos. 5,008,114, 5,225,192, 5,275,824, 5,354,560, 5,449,521, and 5,569,469, all of which are hereby incorporated by reference.

Drug in Nanosuspension Form

In another embodiment of the invention, the solubility-improved form of the drug is a nanosuspension. A nanosuspension is a disperse system of solid-in-liquid or solid-in-semisolid, the dispersed phase comprising pure active compound or an active compound mixture. The average diameter of the dispersed phase is generally between 10 nm and 1,000 nm (determined by photon correlation spectroscopy), the size distribution of the dispersed active phase being quite narrow. That is, the proportion of "microparticles" (that is, particles larger than about 5 μm) in the active particle population is very low. The nanosuspension can be surfactant-free, but can also comprise surfactants or stabilizers or both. The nanosuspension can also be lyophilized or spray dried, and the nanoparticles of a nanosuspension can also be incorporated into a solid carrier matrix. See U.S. Pat. No. 5,858,410, the entire contents of which are hereby incorporated by reference.

Although there are many methods to produce the nanosuspensions, one method suitable is by comminuting the solid particles by using cavitation or shearing and impact forces with introduction of a high amount of energy. A specific process for comminuting the solid particles comprises preparing a suspension of active drug in an aqueous solution followed by passing the aqueous suspension through a piston-gap homogenizer at least once and up to 10 to 30 times. Exemplary piston-gap homogenizers are the Micron Lab 40, Microfluidizer Model 110-Y (Microfluidics, Inc.) and the Nanojet (Nanojet Engineering, GmbH). A second method for producing the nanosuspension is by rapid expansion from a supercritical solution. See U.S. Pat. No. 6,177,103, the entire contents of which are hereby incorporated by reference. In this process the nanosuspension is produced by: (a) dissolving the drug and a surface modifier in a liquefied compressed gas solvent to form a solution of greater than 1% w/w of drug in the solvent; then (b) expanding the compressed fluid solution prepared in step (a) into water or an aqueous solution containing a second surface modifier; then (c) homogenizing the suspension of step (b) at high pressure.

A concentration-enhancing polymer may be comminuted with the drug and other excipients, or the nanosuspension form may first be prepared and then mixed with the concentration-enhancing polymer.

Drug in Supercooled Form

Yet another solubility-improved form of the drug is drug that is in a supercooled form. By "supercooled," "supercooled melt" or "supercooled form" means that the drug, which is normally a solid, crystalline or amorphous substance at ambient conditions, has been formulated so that it is not present in a solid, crystalline state at temperatures below its bulk melting point, but is instead in a solid state which is characterized by a more random distribution of atoms or molecules such as is observed in liquids or melts. An example of supercooled drug is disclosed in U.S. Pat. No. 6,197,349, which is incorporated by reference.

The supercooled drug is often in the form of a dispersion. One such dispersion can be made by a specific melt emulsification method characterized by the following steps:

1. The drug is melted. Optionally, one or more additives, which decrease the melting point of the drug and/or impede or inhibit the recrystallization of the molten drug are added.

2. Optionally, one or more stabilizing agents (e.g. amphiphilic substances, surfactants, emulsifiers) are dissolved or dispersed in the melt or in the dispersion medium depending on their physicochemical characteristics. Stabilizers can also be added or exchanged after homogenization, e.g. by adsorption of polymers or by dialysis of water-soluble stabilizers.

3. Preferably, the dispersion medium is heated to approximately the temperature of the melt prior to mixing and may contain additives, e.g., stabilizers, isotonicity agents, buffering agents, cryoprotectants and/or preservatives.

4. Optionally, the dispersion medium and the melt are added and predispersed to give a crude dispersion, for example by shaking, stirring, sonication or vortexing. Predispersing is preferably carried out at temperatures above the melting point of the substance or the mixture of substances or the mixture of substances and additives, e.g., stabilizers, respectively. Predispersing can he omitted for well dispersible systems.

5. The melt is then emulsified in the dispersion medium, preferably at temperatures above the melting point of the substance or the mixture of substances or the mixture of substances and additives, e.g., stabilizers, respectively. Emulsification is preferably carried out by high pressure homogenization or by sonication, but may be also possible by high speed stirring, vortexing and vigorous hand shaking.

6. The dispersion can then be further processed into suitable dosage forms.

A concentration-enhancing polymer may be mixed with the molten drug or the supercooled drug form may first be prepared and then mixed with the concentration-enhancing polymer.

Cyclodextrin/Drug Formulations

Various solubility-improved drug forms using cyclodextrin are well known in the art. As used herein, the term "cyclodextrin" refers to all forms and derivatives of cyclodextrin. Particular examples of cyclodextrin include α-cyclodextrin, β-cyclodextrin, and γ-cyclodextrin. Exemplary derivatives of cyclodextrin include mono- or polyalkylated β-cyclodextrin, mono- or polyhydroxyalkylated β-cyclodextrin, hydroxypropyl β-cyclodextrin (hydroxypropylcyclodextrin), mono, tetra or hepta-substituted β-cyclodextrin, and sulfoalkyl ether cyclodextrin (SAE-CD). These drug forms, also known as cyclodextrin derivatives, herein after referred to as "cyclodextrin/drug forms" can be simple physical mixtures. An example of such is found in U.S. Pat. No. 5,134,127, herein incorporated by reference. For example, the active drug and sulfoalkyl ether cyclodextrin (SAE-CD) may be preformed into a complex prior to the preparation of the final formulation. Alternatively, the drug can be formulated by using a film coating surrounding a solid core comprising a release rate modifier and a SAE-CD/drug mixture, as disclosed in U.S. Pat. No. 6,046,177 ('177), herein incorporated by reference. Upon exposure in the use environment, the SAE-CD/drug mixture converts to a complex. Alternatively, controlled-release formulations containing SAE-CD may consist of a core comprising a physical mixture of one or more SAE-CD derivative, an optional release rate modifier, a therapeutic agent, a major portion of which is not complexed to the SAE-CD, and an optional release rate modifying coating surrounding the core. Other cyclodextrin/drug forms contemplated by the invention are found in U.S. Pat. Nos. 5,134,127, 5,874,418, and 5,376,645, all of which are incorporated by reference. For example, the drug in cyclodextrin, e.g. SAE-CD, may be physically mixed, wherein a major portion of the drug is not complexed to the SAE-CD in the composition. A preferred SAE-CD is sulfobutyl ether-CD.

Drug in the Form of a Softgel

Another solubility-improved drug form, herein referred to as the "softgel form," generally relates to a drug encapsulated in soft-gelatin. Typically, such softgel forms comprise a soft-gelatin capsule filled with a material, the material often being a highly concentrated solution of drug in a liquid. The fill material generally comprises either a water miscible carrier, such as polyethylene glycol or polyvinylpyrrolidone, or a water immiscible carrier, such as a lipid or oil, in which the drug is dissolved with or without a surfactant or emulsifying agent. The fill material is placed into the soft gelatin capsule, for example, by encapsulating the fill material between two sheets of gelatin as it passes between a pair of die rolls having surface cavities shaped to form the desired shape of the resulting softgel. Such soft-gel drug forms are well-known and are described in "The Theory and Practice of Industrial Pharmacy", by L. Lachman, H. Lieberman, and J. Kanig, Lea and Febiger, publisher, 3$^{rd}$ Edition, 1986.

A concentration-enhancing polymer may be blended with the fill material prior to filling the soft gelatin capsule, it may be added separately to the soft-gelatin capsule, or the softgel drug form may first be prepared and then blended with the concentration-enhancing polymer.

One variation on the softgel form is found in U.S. Pat. Nos. 5,071,643 and 5,360,615, the disclosures of which are incorporated herein by reference. These patents disclose a solvent system for enhancing the solubility of a pharmaceutical agent to produce a highly concentrated solution suitable for softgel filling comprising 10 to 80% polyethylene glycol, 1 to 20% by weight of water, and the pharmaceutical agent. The composition also comprises 0.2 to 1.0 mole equivalents of an ionizing agent per mole equivalent pharmaceutical agent. Glycerin or polyvinylpyrrolidone may be added to further enhance the solubility of certain drugs. U.S. Pat. No. 5,376,688, herein incorporated by reference, disclose the use of a fill material comprising 0 to 20% water, a solution of a pharmaceutical agent, an ionizing agent, and a solvent selected from the group consisting of diethylene glycol monoethyl ether, polyglycerol oleate, alpha-hydro-w-hydroxypoly(oxyethylene)-poly(oxypropylene)-poly(oxyethylene) bloc copolymers, and mixtures thereof.

A separate embodiment of this drug form can be found in EP 0 605 497, herein incorporated by reference. This drug form can be varied from a semi-liquid to a semi-solid formed by high-pressure homogenization of a pre-emulsion of melted lipid containing a dissolved drug. After cooling to room temperature, solid particles are formed. Drugs may be adsorbed in the lipid depending on the physicochemical properties of the drug.

Gelatin Form

Another solubility-improved drug form is a gelatin form of the drug, herein referred to as the "gelatin form" or "gelatin drug form." Gelatin drug form comprises a drug and a gelatin-based material, the drug either coated with, encapsulated in, or dispersed in the gelatin-based material, typically using an aqueous-based solvent system. It is believed the gelatin coats or encapsulates the particles of the drug and prevents aggregation or clumping of the particles, leading to increased solubility and/or dissolution of the drug. (Hereinafter, the terms "coated with" or "coats" are used to describe the drug coated with, encapsulated in, or dispersed in the gelatin-based material.)

One particular gelatin form is found in U.S. Pat. Nos. 5,851,275, 5,834,022 and 5,686,133 herein incorporated by reference. In this embodiment, the drug is mixed with gelatin and lecithin and then coated, or the drug is coated with gelatin and lecithin using standard coating methods. When coated with the gelatin and lecithin, the general method includes the steps of dissolving gelatin in water heated to between 35° C. to 40° C. Lecithin is added to the gelatin/water mixture and is thoroughly mixed therein. At least one pharmaceutical ingredient in solid particulate form is then added slowly and mixed so as to cause thorough and uniform coating of the particles of the pharmaceutical ingredient. Following coating with the gelatin/lecithin mixture, the aqueous solvent is removed by various techniques, including lyophylization (e.g., freeze-drying) or spray drying.

The general range of concentrations of excipient (i.e., the lecithin/gelatin) and pharmaceutical ingredient is shown. The concentration in the coating solution of gelatin and lecithin broadly ranges from approximately 0.001-99.9% (w/v) each and more preferably 0.01 to 2.0% each. The concentration in the coating solution of the pharmaceutical ingredient ranges from approximately 0.1-15.0% (w/v). It is preferable that the lecithin and gelatin be present in a 1:1 ratio.

The contacting step includes coating the pharmaceutical ingredient with the mixture including water gelatin and lecithin. The coating step can be accomplished by simple immersion of the particles of the pharmaceutical ingredient. It is believed that the gelatin coats the particles of the pharmaceutical ingredient and prevents aggregation or clumping of the particles. The lecithin element is thought to reduce surface tension thereby preventing aggregation or form a microemulsion or to form micelles that facilitate dissolution of the pharmaceutical ingredient. In acting in this complementary fashion, the coating including gelatin and lecithin increases the dissolution rate of water-insoluble pharmaceutical ingredients. The above-described theory is provided merely for descriptive purposes and is no way intended to limit the scope of the present invention.

Another embodiment of this drug form, useful to increase a drug's rate of dissolution and bioavailability in a use environment, is disclosed in U.S. Pat. Nos. 5,405,616 and 5,560,924, herein incorporated by reference. This drug form is generally prepared by selecting a gelatin or gelatin derivative according to their isoelectric point (IEP), so that their IEP is adapted to the charge of the drug particles, leading to a neutral charge when the gelatin or its derivative is combined with the undissolved drug at a determined pH value. The gelatin or its derivatives are converted into an aqueous sol form, their pH value is set according to the IEP of the gelatin at a value that stabilizes the particle of the drug at an approximately or totally neutral charge. Before or after this last step, the drug is dissolved in the aqueous gelatin sol or a solution of the drug is blended with the aqueous gelatin sol. Then, the drug or drug blend can be dried, creating a dry powder.

A concentration-enhancing polymer may be mixed with the drug prior to coating with the gelatin, or the gelatin drug form may first be prepared and then mixed with the concentration-enhancing polymer.

Drug in Self-Emulsifying Form

Another solubility-improved drug form is a self-emulsifying form of the drug, herein referred to as the "self-emulsifying form." A "self-emulsifying form" as used herein, generally refers to a drug form comprising a drug dissolved in a mixture of lipophilic material or phase, and one or more surfactants and cosurfactants. Preferably, upon ingestion of the self-emulsifying form, the drug/lipophilic material/surfactant mixture forms a microemulsion thereby enhancing the absorption of the drug in vivo. Self-emulsifying drug forms avoid the dissolution step that frequently limits the rate of absorption of low-solubility drugs from the crystalline state. See for example, C. W. Pouton, "Formation of Self-Emulsifying Drug Delivery Systems," *Advanced Drug Delivery Reviews*, 25 (1997)$_{47}$-58. Self-emulsifying drug forms are often filled into soft-gelatin capsules, as discussed under the softgel drug form.

In one embodiment, the self-emulsifying drug form is comprised of at least one drug; a lipophilic phase, including an oil or lipid material; a surfactant; and a hydrophilic phase. The materials used are often selected based on the empirical parameter commonly referred to as the hydrophilic-lipophilic balance (HLB value) of the material. Materials with low HLB values are more lipophilic, while those with high HLB values are more hydrophilic. Materials used in self-emulsifying drug form compositions include polyglycolyzed glycerides, polyethoxylated fatty acids, polyethylene glycol fatty acid diesters, polyethylene glycol fatty acid mono- and di-ester mixtures, polyethylene glycol glycerol fatty acid esters, transesterification products of natural and hydrogenated oils, polyglycerized fatty acids, propylene glycol fatty acid esters, mixtures of propylene glycol esters and glycerol esters, mono- and di-glycerides, tri-glycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, ionic surfactants, and mixtures thereof. Examples of self-emulsifying drug forms can be found in U.S. Pat. Nos. 6,294,192 B1, 6,054,136, 5,444,041, 5,993,858, 6,054,136, 6,280,770 B1, 6,309,665 B2, 6,312,704 B1, and PCT Patent Application No. WO 01/01960 A1, the disclosures of which are incorporated by reference.

A concentration-enhancing polymer may be included as part of the self-emulsifying drug form formulation, or the self-emulsifying drug form may first be prepared and then mixed with the concentration-enhancing polymer.

Three-Phase Form

Another solubility-improved drug form is the "three-phase form." An example of a three-phase form is described in U.S. Pat. No. 6,042,847, herein incorporated by reference. Essentially, the three-phase form gives a constant or controlled release of an amorphous active ingredient stabilized with polymers for a single daily peroral application, which is especially suitable for active ingredients existing in amorphous form or in one or more polymorphous forms, which exhibit poor solubility in crystal form depending on the polymorphous form, particle size and the specific surface area of the active ingredient. In general, this form comprises a core consisting of a first and a second phase and a coating representing the third phase. In the first phase the three-phase pharmaceutical form contains an amorphous active ingredient, the water-soluble polymer polyvinylpyrrolidone and a cellulose ether as carriers of the amorphous active ingredient and simultaneously as inhibitors of its crystallization, and a surfactant that improves the solubility of the active ingredient and promotes the absorption of the amorphous active ingredient from gastrointestinal tract. In the second phase it contains a cellulose ether and a mixture of mono-, di- and triglycerides as sustained release agents. The third phase is represented by a poorly soluble or gastro-resistant film coating, which in the first few hours after the application controls the release of the active ingredient and can consist of an ester of hydroxypropylmethylcellulose with phthalic anhydride or of a copolymerizate based on methacrylic acid and ethyl acrylate.

Concentration-Enhancing Polymers

Concentration-enhancing polymers suitable for use in the various aspects of the present invention should be pharmaceutically acceptable, and should have at least some solubility in aqueous solution at physiologically relevant pHs (e.g. 1-8). Almost any neutral or ionizable polymer that has an aqueous-solublitity of at least 0.1 mg/mL over at least a portion of the pH range of 1-8 may be suitable.

It is preferred that the concentration-enhancing polymers be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution. A particularly preferred class of amphiphilic polymers are those that are ionizable, the ionizable portions of such polymers, when ionized, constituting at least a portion of the hydrophilic portions of the polymer. For example, while not wishing to be bound by a particular theory, such polymer/drug assemblies may comprise hydrophobic drug clusters surrounded by the concentration-enhancing polymer with the polymer's hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion pairing or hydrogen bonds, with ionic or polar groups of the drug. In the case of ionizable polymers, the hydrophilic regions of the polymer would include the ionized functional groups. In addition, the repulsion of the like charges of the ionized groups of such polymers (where the polymer is ionizable) may serve to limit the size of the polymer/drug assemblies to the nanometer or submicron scale. Such drug/concentration-enhancing polymer assemblies in solution may well resemble charged polymeric micellar-like structures. In any case, regardless of the mechanism of action, the inventors have observed that such amphiphilic polymers, particularly ionizable cellulosic polymers such as those listed below, have been shown to interact with drug so as to maintain a higher concentration of drug in an aqueous use environment.

One class of polymers suitable for use with the present invention comprises neutral non-cellulosic polymers. Exemplary polymers include: vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alky- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; polyethylene polyvinyl alcohol copolymers; and polyoxyethylene-polyoxypropylene block copolymers (also known as poloxamers).

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass.; amine-functionalized polyacrylates and polymethacrylates; high molecular weight proteins such as gelatin and albumin; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate substituents attached via ester linkages to a significant fraction of the cellulosic polymer's hydroxyl groups. Generally, the degree of substitution of each substituent can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulose polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of non-ionizable cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thio-acetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, ethyl carboxymethyl cellulose (also referred to as carboxymethyl ethyl cellulose), carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

The inventors have found the following cellulosic polymers result in exceptional concentration enhancement: hydroxypropyl methyl cellulose acetate succinate (HPMCAS), such as the LF, LG, MF, MG, HF, and HG grades available from Shin-Etsu; cellulose acetate phthalate (CAP), such as the HF and CE grades available from Eastman Chemical; hydroxypropyl methyl cellulose phthalate (HPMCP), such as the NF grade available from Eastman Chemical, cellulose acetate trimellitate (CAT), available from Eastman Chemical; and hydroxypropyl methyl cellulose such as the E3 PremLV grade available from Dow.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a p$K_a$ of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned provisional patent application U.S. Serial No. 60/300,256 entitled "Pharmaceutical Compositions of Drugs and Neutralized Acidic Polymers" Jun. 22, 2001, the relevant disclosure of which is incorporated by reference.

While specific concentration-enhancing polymers have been discussed as being suitable for use in the mixtures of the present invention, blends of such concentration-enhancing polymers may also be suitable. Thus, the term "concentration-enhancing polymer" is intended to include blends of concentration-enhancing polymers in addition to a single species of concentration-enhancing polymer.

Preparation of the Compositions

The compositions of the present invention may be prepared by dry- or wet-mixing the solubility-improved drug form with the concentration-enhancing polymer or a blend of concentration enhancing polymers to form the composition. Mixing processes include physical processing as well as wet-granulation and coating processes.

For example, mixing methods include convective mixing, shear mixing, or diffusive mixing. Convective mixing involves moving a relatively large mass of material from one part of a powder bed to another, by means of blades or paddles, revolving screw, or an inversion of the powder bed. Shear mixing occurs when slip planes are formed in the material to be mixed. Diffusive mixing involves an exchange of position by single particles. These mixing processes can be performed using equipment in batch or continuous mode. Tumbling mixers (e.g., twin-shell) are commonly used equipment for batch processing. Continuous mixing can be used to improve composition uniformity.

Milling may also be employed to prepare the compositions of the present invention. Milling conditions are generally chosen which do not alter the physical form of the drug in the sense that the drug and concentration-enhancing polymer are not mixed at the molecular level to form a dispersion of polymer and drug. Conventional mixing and milling processes suitable for use in the present invention are discussed more fully in Lachman, et al., *The Theory and Practice of Industrial Pharmacy* (3d Ed. 1986).

Alternatively, the concentration-enhancing polymer may be included as part of or as an additive to the solubility-improved drug form, the concentration-enhancing polymer being mixed with the drug when the solubility-improved drug form is prepared. For example, in the case of a nanoparticulate drug form, the concentration-enhancing polymer may be included with the drug in a dispersion media that is subjected to a mechanical means to reduce the particle size of the drug substance. In another example, the concentration-enhancing polymer can be added with the drug to a lipid or colloidal protein to form a softgel drug form.

In addition to the physical mixtures described above, the compositions of the present invention may constitute any device or collection of devices that accomplishes the objective of delivering to the use environment both the drug form and the concentration-enhancing polymer. For example, the composition may be in the form of a dosage form in which the drug form and concentration-enhancing polymer occupy separate regions within the dosage form. Thus, in the case of oral administration to a mammal, the dosage form may constitute a layered tablet wherein one or more layers comprise the drug form and one or more other layers comprise the concentration-enhancing polymer. Alternatively, the dosage form may be a coated tablet wherein the tablet core comprises the drug form and the coating comprises the concentration-enhancing polymer. In addition, the drug form and the concentration-enhancing polymer may even be present in different dosage forms such as tablets or beads and may be administered simultaneously or separately as long as both the drug form and concentration-enhancing polymer are administered in such a way that the drug form and polymer can come into contact in the use environment. When the drug form and the concentration-enhancing polymer are administered separately it is generally preferable to deliver the concentration-enhancing polymer prior to or at the same time as the drug.

The amount of concentration-enhancing polymer relative to the amount of drug form present in the mixtures of the present invention depends on the drug form and concentration-enhancing polymer and may vary widely from a drug-to-concentration-enhancing polymer weight ratio of about 0.01 to about 20. However, in most cases, except when the drug dose is quite low (e.g., 25 mg or less) it is preferred that the drug-to-polymer ratio is greater than 0.05 and less than about 5.0 and often the enhancement in drug concentration or relative bioavailability is observed at drug-to-polymer ratios of 1 or less or for some drugs even 0.2 or less. In cases when the drug dose is about 25 mg or less, the drug-to-polymer weight ratio may be significantly less than 0.05. In general, regardless of the dose, enhancements in drug concentration or relative bioavailability tend to increase with decreasing drug-to-polymer weight ratio down to a value of about 0.75 to 0.10. However, due to the practical limits of keeping the total mass of a tablet, capsule, or suspension low, it is often desirable to use a relatively high drug-to-polymer ratio as long as satisfactory results are obtained. The maximum drug: concentration-enhancing polymer ratio that yields satisfactory results varies from drug to drug and is best determined by conducting in vitro and/or in vivo dissolution tests described below.

Concentration Enhancement

The concentration-enhancing polymer is present in a sufficient amount so as to improve the concentration of the drug in a use environment relative to a control composition. At a minimum, the compositions of the present invention provide concentration-enhancement relative to a control comprising an equivalent quantity of the drug in the same solubility-improved form as the composition but with no concentration-enhancing polymer. Thus, the concentration-enhancing polymer is present in a sufficient amount so that when the composition is administered to a use environment, the composition provides improved drug concentration (as described more fully below) relative to a control consisting of an equivalent amount of drug in the same solubility-improved form, but with no concentration-enhancing polymer present.

The presence of the concentration-enhancing polymer increases the time required for the drug concentration to fall to equilibrium. In fact, when compositions of the invention are administered to a use environment such as the GI tract where dissolved drug is absorbed from the GI fluids, much or all of the drug may be absorbed prior to the drug being substantially converted to its lowest solubility form. Typical enhancements of dissolved drug concentration over equilibrium drug concentration may be on the order of 1.25-fold to 20-fold, and in some cases 20-fold to 100-fold. For example, where the control provides an equilibrium concentration of 1 mg/mL and the composition provides a maximum drug concentration of 1.25 mg/mL, the composition provides a 1.25-fold enhancement.

It is believed the concentration-enhancing polymers act to slow the rate of precipitation or crystallization of the drug after the drug is initially dissolved. As mentioned previously, because conversion of dissolved drug to a lower solubility form than that of the original solubility-improved form can occur rapidly relative to dissolution, the presence of the polymer may allow a much higher total dissolved drug concentration than is possible in its absence. The presence of the concentration-enhancing polymer(s) thus allows the initially increased or enhanced concentration provided by the drug form to be at least partially maintained for at least a few minutes and, in some cases, for many hours.

The concentration-enhancing polymers of the present invention provide enhanced concentration of the drug in a use environment exceeding the equilibrium concentration for a longer period of time than a control composition comprising an equivalent quantity of the drug form when subjected to a dissolution test. That is, even though the control composition may provide an enhanced concentration of drug in the use environment that exceeds the equilibrium concentration, the control does so for a shorter period of time than the compositions of the present invention which contain a concentration-enhancing polymer. Preferably, a composition of the present invention provides an enhanced drug concentration that exceeds the equilibrium concentration for a period of at least 15 minutes, preferably a period of at least 30 minutes, preferably a period of at least 60 minutes, and even more preferably a period of at least 90 minutes longer than does the drug concentration provided by a control composition that does not contain the concentration-enhancing polymer.

As used herein, the term "concentration of drug" in solution or in a use environment refers to drug that may be dissolved in the form of solvated monomeric molecules, so called "free drug," or any other drug-containing submicron structure, assembly, aggregate, colloid, or micelle. As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS) or a Model Fasted Duodenal (MFD) solution. An appropriate PBS solution is an aqueous solution comprising 20 mM sodium phosphate, 47 mM potassium phosphate, 87 mM NaCl and 0.2 mM KCl, adjusted to pH 6.5. An appropriate MFD solution is the same PBS solution wherein additionally is present 7.3 mM sodium taurocholic acid and 1.4 mM of 1-palmitoyl-2-oleyl-sn-glycero-3-phosphocholine.

A composition of the invention can be tested in vivo or, more conveniently, in vitro to ascertain whether it is within the scope of the invention. A composition can be dissolution-tested by adding it to a PBS or an MFD solution and agitating to promote dissolution. For example, a composition or a method for administration of drug that meets at least one or more of the concentration criteria in either PBS or MFD or meets one or more of the concentration or bioavailability criteria when dosed orally to the GI tract of an animal, including a mammal such as a human, is a composition or method of this invention.

In one aspect, the compositions of the present invention comprising a drug in a solubility-improved form combined with a concentration-enhancing polymer provide a maximum concentration of the drug in a use environment that is at least 1.25-fold the maximum concentration of drug in the use environment provided by a control composition comprising an equivalent amount of the drug form but without concentration-enhancing polymer present. The conventional or control composition is the drug form alone or combined with a weight of inert diluent equivalent to the weight of concentration-enhancing polymer in the inventive composition. Preferably, the maximum concentration of drug achieved with the composition of the present invention is at least 2-fold and more preferably at least 3-fold the maximum concentration provided by the control.

In making such comparisons using this dissolution test or any of the dissolution tests or bioavailability tests described below, it is important that the total amount of drug form dosed be sufficiently high that meaningful comparisons can be made. Specifically, both the compositions of this invention and the control compositions must be dosed at a level at least 2-fold and preferably at 4-fold, and more preferably at least 10-fold, the maximum drug concentration achieved by the control composition.

Alternatively, the compositions of the present invention provide a dissolution AUC for any period of at least 90 minutes between the time of introduction into the use environment and about 270 minutes following introduction to the use environment that is at least 1.25-fold that of a dissolution AUC provided by a control composition comprising an equivalent quantity of drug form but not containing the concentration-enhancing polymer. Dissolution AUC is the integration of a plot of the drug concentration versus time over a specified time period. For purposes of determining whether a composition or method is part of this invention, the dissolution AUC is calculated over a time period of at least 90 minutes. The time period may be chosen for any time period between the time of introduction into the use environment (time=0) and about 270 minutes following introduction into the use environment. Thus, among the many acceptable time periods are included, for example, (1) from the time of introduction into the use environment to 90 minutes following introduction into the use environment; (2) from the time of introduction into the use environment to 180 minutes following introduction into the use environment; and (3) from 90 minutes following introduction into the use environment to 180 minutes following introduction into the use environment. A composition or method is part of this invention if it meets the dissolution AUC criterion for at least one acceptable time period. In vitro determinations of AUC can be made by plotting drug concentration versus time after dissolving the drug composition in, for example, PBS or MFD solution. Measurement of the AUC in vivo, where the use environment is, for example, the GI tract, is more complicated. This requires sampling the GI fluid as a function of time and thus is less preferred than the in vitro dissolution test or the in vivo relative bioavailability test.

In a preferred embodiment, the composition comprising the mixture provides enhanced relative bioavailability of the drug. In general, compositions or methods of the present invention that are evaluated using one of the in vitro test methods and found to be a part of the invention will perform well in vivo as well. Bioavailability of drugs in the compositions or methods of the present invention can be tested in vivo in animals, such as mammals and humans using conventional methods for making such a determination. A convenient measure of in vivo bioavailability is the "relative bioavailability," defined as the ratio of the plasma or serum AUC determined from a plot of the plasma or serum drug concentration versus time measured for the composition or method of the present invention to the plasma or serum AUC of a control composition or method that is free of the concentration-enhancing polymer.

A composition of the present invention achieves a relative bioavailability that is at least 1.25 relative to the above-mentioned control. Preferably, the relative bioavailability provided by the composition of the present invention is at least 1.5, more preferably at least 2, and even more preferably at least 3 or more, relative to the control composition.

Compositions or methods of the invention pass either one or more in vitro dissolution tests or the in vivo relative bioavailability test or both in vitro and in vivo tests.

The concentration of dissolved drug in a dissolution test is typically measured by sampling the test medium and analyzing for the dissolved drug concentration. To avoid relatively large drug particulates which would give an erroneous determination, the test solution is either filtered or centrifuged. "Dissolved drug" is typically taken as that material that either passes a 0.45 µm syringe filter or alternatively the material that remains in the supernatant following centrifugation. Filtration can be conducted using a 13 mm, 0.45 µm polyvinylidine difluoride syringe filter sold by Scientific Resources under the trademark TITAN®. Centrifugation is typically carried out in a polypropylene microcentrifuge tube by centrifuging at about 13,000 G for about 60 seconds. Other similar filtration or centrifugation methods can be employed and useful results obtained. For example, using other types of microfilters may yield values somewhat higher or lower (±10-40%) than that obtained with the filter specified above but will still allow identification of preferred compositions. It will be appreciated by one of ordinary skill that this definition of "dissolved drug" encompasses not only monomeric solvated drug molecules but also a wide range of species such as polymer drug assemblies that have submicron dimensions such as drug aggregates, aggregates of mixtures of polymer and drug, micelles, polymeric micelles, colloidal particles, polymer/drug complexes, and other such drug-containing species that are present in the filtrate or supernatant in the specified dissolution test.

While not wishing to be bound by a particular theory, it is believed that while the concentration-enhancing polymer(s) of the present invention may to some extent solubilize insoluble drugs (that is, to increase the equilibrium concentration of free drug), the concentration-enhancing polymers also act to slow the rate of precipitation or crystallization of the drug after the drug is initially dissolved. The presence of the concentration-enhancing polymer(s) thus allows the initially increased or enhanced concentration provided by the drug form to be at least partially maintained for at least a few minutes and, in some cases, for many hours. In addition, in cases where dissolution of the drug is slow and precipitation of the drug, in the absence of the concentration-enhancing polymer, is fast, the presence of the concentration-enhancing polymer may result in the maximum concentration of drug observed being substantially higher than that observed in the absence of the concentration-enhancing polymer.

One possible mechanism for improving the drug concentration involves the association of the concentration-enhancing polymer and dissolved drug to form "polymer/drug assemblies." Such assemblies may constitute various forms, including polymeric micelles, high-energy polymer-drug aggregates ranging in size from a few nanometers to 5000 nanometers, polymer-stabilized drug colloids or polymer/drug complexes. An alternative view is that as dissolved drug begins to precipitate or crystallize from solution (e.g., as nucleation begins) the polymer adsorbs to these drug aggregates or nuclei, preventing, or at least retarding, the nucleation or crystal-growth process. In any case, the presence of the polymer serves to enhance the amount of drug that is dissolved or at least available for absorption. Drug present in the various drug/polymer assemblies listed above is apparently quite labile and may contribute to the drug absorption process.

In another aspect of the invention, the concentration-enhancing polymer is present in a sufficient amount so that the composition provides a relative bioavailability that is at least 1.25 relative to the same control composition mentioned above.

In another aspect of the invention, a method is provided for co-administering (1) a drug form and (2) a concentration-enhancing polymer. The concentration-enhancing polymer is co-administered in a sufficient amount so that there is provided in the use environment a maximum concentration of the drug that is at least 1.25-fold that of the maximum concentration provided by the drug form in the use environment of the patient without the polymer present.

In another aspect of the invention, a method is provided for co-administering (1) the drug form and (2) a concentration-enhancing polymer. The concentration-enhancing polymer is co-administered in a sufficient amount so that there is provided in the use environment a dissolution area under the concentration-versus-time curve (AUC) for any period of at least 90 minutes between the time of introduction into the use environment and about 270 minutes following introduction to the use environment that is at least 1.25-fold the corresponding area under the curve provided by the same control composition mentioned above.

In another aspect of the invention, a method is provided for co-administering (1) the drug form, and (2) a concentration-enhancing polymer. The concentration-enhancing polymer is co-administered in a sufficient amount so that there is provided a relative bioavailability that is at least 1.25-fold relative to the same control composition mentioned above.

Excipients and Dosage Forms

Although the key ingredients present in the compositions of the present invention are simply the drug form and the concentration-enhancing polymer(s), the inclusion of other excipients in the composition may be useful. These excipients may be utilized with the drug form/concentration-enhancing polymer mixture in order to formulate the mixture into tablets, capsules, suspensions, powders for suspension, creams, transdermal patches, depots, and the like. Drug and concentration-enhancing polymer can be added to other dosage form ingredients in essentially any manner that does not substantially alter the drug form. In addition, as described above, the drug form and the concentration-enhancing polymer may be mixed with excipients separately to form different beads, or layers, or coatings, or cores or even separate dosage forms.

One very useful class of excipients is surfactants. Suitable surfactants include fatty acid and alkyl sulfonates; commercial surfactants such as benzethanium chloride (HYAMINE® 1622, available from Lonza, Inc., Fairlawn, N.J.); DOCUSATE SODIUM (available from Mallinckrodt Spec. Chem., St. Louis, Mo.); polyoxyethylene sorbitan fatty acid esters (TWEEN®, available from ICI Americas Inc., Wilmington, Del.); LIPOSORB® P-20 (available from Lipochem Inc., Patterson N.J.); CAPMUL® POE-0 (available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, or formation of micelles. These surfactants may comprise up to 5 wt % of the composition.

The addition of pH modifiers such as acids, bases, or buffers may also be beneficial, retarding the dissolution of the composition (e.g., acids such as citric acid or succinic acid when the polymer is anionic) or, alternatively, enhancing the rate of dissolution of the composition (e.g., bases such as sodium acetate or amines when the polymer is anionic).

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition.

Examples of matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, maltodextrin, calcium carbonate, dibasic calcium phosphate, tribasic calcium phosphate, calcium sulfate, magnesium carbonate, magnesium oxide, poloxamers such as polyethylene polypropylene oxide, and hydroxypropyl methyl cellulose.

Examples of disintegrants include sodium starch glycolate, sodium carboxymethyl cellulose, calcium carboxymethyl cellulose, croscarmellose sodium, crospovidone, methyl cellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include silicon dioxide, talc, and cornstarch.

Other conventional form excipients may be employed in the compositions of this invention, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

Compositions of this invention may be used in a wide variety of dosage forms for administration of drugs. Exemplary dosage forms are powders or granules that may be taken orally either dry or reconstituted by addition of water to form a paste, slurry, suspension or solution; tablets; capsules; multiparticulates; and pills. Various additives may be mixed, ground, or granulated with the compositions of this invention to form a material suitable for the above dosage forms.

In some cases, the overall dosage form or particles, granules or beads that make up the dosage form may have superior performance if coated with a polymer, particularly an enteric polymer, to prevent or retard dissolution until the dosage form leaves the stomach. Exemplary enteric coating materials include HPMCAS, CAP, HPMCP, CAT, carboxylic acid-functionalized polymethacrylates, and carboxylic acid-functionalized polyacrylate.

Compositions of this invention may be administered in a controlled release dosage form. In one such dosage form, the composition of the drug form and concentration-enhancing polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the mixture of drug form and concentration-enhancing polymer. The aqueous-swollen matrix gradually erodes, swells, disintegrates or dissolves in the environment of use, thereby controlling the release of the drug mixture to the environment of use.

Alternatively, the compositions of the present invention may be administered by or incorporated into a non-erodible matrix device.

Alternatively, the invention may be delivered using a coated osmotic controlled release dosage form. This dosage form has two components: (a) the core which contains an osmotic agent and the drug form and the concentration-enhancing polymer either mixed or in separate regions of the core; and (b) a non-dissolving and non-eroding coating surrounding the core, the coating controlling the influx of water to the core from an aqueous environment of use so as to cause drug release by extrusion of some or all of the core to the environment of use. The osmotic agent contained in the core of this device may be an aqueous-swellable hydrophilic polymer, osmogen, or osmagent. The coating is preferably polymeric, aqueous-permeable, and has at least one delivery port.

Alternatively, the invention may be delivered via a coated hydrogel controlled release dosage form having three components: (a) a composition containing the drug form, (b) a water-swellable composition wherein the water-swellable composition is in a separate region within a core formed by the drug-containing composition and the water-swellable composition, and (c) a coating around the core that is water-permeable, water-insoluble, and has a least one delivery port therethrough. In use, the core imbibes water through the coating, swelling the water-swellable composition and increasing the pressure within the core, and fluidizing the drug-containing composition. Because the coating remains intact, the drug-containing composition is extruded out of the delivery port into an environment of use. The concentration-enhancing polymer may be delivered in a separate dosage form, may be included in the drug-containing composition or may constitute all or part of a coating applied to the dosage form.

Alternatively, the compositions of the present invention may be co-administered, meaning that the drug form can be administered separately from, but within the same general time frame as, the concentration-enhancing polymer. Thus, a drug form can, for example, be administered in its own dosage form which is taken at approximately the same time as the concentration-enhancing polymer which is in a separate dosage form. If administered separately, it is generally preferred to administer both the drug form and the concentration-enhancing polymer within 60 minutes of each other, so that the two are present together in the environment of use. When not administered simultaneously, the concentration-enhancing polymer is preferably administered prior to the drug form.

In addition to the above additives or excipients, use of any conventional materials and procedures for preparation of suitable dosage forms using the compositions of this invention known by those skilled in the art are potentially useful.

Other features and embodiments of the invention will become apparent from the following examples which are given for illustration of the invention rather than for limiting its intended scope.

EXAMPLE 1

A pharmaceutical composition comprising Danazol, a surface modifier (polyvinylpyrrolidone (PVP)), and a concentration-enhancing polymer is manufactured by the following steps.

Danazol (which can be purchased in a micronized form from Sterling Drug Inc.) is added to a solution of PVP (which can be purchased from GAF) and water. The solution is rolled for about a week to create a homogeneous mixture. This mixture is then milled in a mill-grinding chamber (such as a DYNO-MILL, Model KDL, manufactured by Willy A. Bachoffen AG Maschinenfabrik) with silica glass spheres. Milling will continue until the average particle size is less than about 400 nm. Particle size can be measured by using a DuPont sedimentation field flow factionator. A concentration-enhancing polymer is added to the milled mixture in an amount effective to achieve concentration enhancement. A suitable concentration-enhancing polymer is the MF grade of hydroxypropyl methyl cellulose acetate succinate (HPMCAS-MF, available from Shin Etsu). The concentration of drug in solution of the milled pharmaceutical composition can be measured as outlined supra. This can be compared to a control composition manufactured identically as above without the concentration-enhancing polymer.

EXAMPLE 2

A 600 ml cylindrical glass vessel is filled approximately halfway with zirconium oxide grinding spheres with diameters in the range of about 0.85-1.18 mm (Zircoa, Inc.). Then, about 10.8 g of micronized Danazol, about 3.24 g of PVP and about 201.96 g water are added to the glass vessel. The glass vessel is rotated horizontally about its axis at 57% of the "critical speed." The critical speed is defined as the rotational speed of the grinding vessel when centrifuging of the grinding media occurs. At this speed the centrifugal force acting on the grinding spheres presses and holds them firmly against the inner wall of the vessel. Conditions that lead to unwanted centrifuging can be computed from simple physical principles.

After about 5 days of ball milling, the slurry is separated from the grinding media through a screen and evaluated for particle size with the sedimentation field flow fractionator. The number average particle diameter should be less than about 400 nm, preferably less than about 100 nm. A concentration-enhancing polymer is then added in an amount effective to achieve concentration enhancement. Suitable concentration-enhancing polymers include HPMCAS, CAT, CAP, HPMCP and HPMC. Testing is then conducted as in Example 1 using a control that does not have the concentration-enhancing polymer.

EXAMPLE 3

A cylindrical glass vessel having a diameter of 2.75 inches (7.0 cm) with a volume of 400 ml is charged with 212 ml of unleaded glass grinding media. Then, about 30.4 g of micronized Danazol, about 9.12 g of PVP, and about 112.48 g of high purity water is added to the vessel. The vessel is rotated horizontally on its axis at a controlled rotational speed of about 80.4 revolutions per minute (50% of critical speed) for about 5 days. The slurry is immediately separated from the grinding media and evaluated for particle size and grinding media attrition using inductively coupled plasma emissions (ICP). The particle size measured with a sedimentation field flow fractionator should yield a number average diameter of less than 400 nm, but preferably between about 110 nm and 180 nm. A concentration-enhancing polymer is then added in an amount effective to achieve concentration enhancement. Suitable concentration-enhancing polymers include HPMCAS, CAT, CAP, HPMCP and HPMC. Testing is then conducted as in Example 1 using a control that does not have the concentration-enhancing polymer.

EXAMPLE 4

To a 3 gallon porcelain jar, about 6100 ml of unleaded glass spheres with diameter of between 0.85-1.18 mm are added. Then, about 1000 g of micronized Danazol, about 300 g of PVP, and about 3700 g high purity water are added. The vessel is rolled about 5 days at a rotational speed of 39.5 revolutions per minute (50% critical speed). The liquid slurry is separated from the grinding media with a screen and used to prepare solid oral doses. Average particle size should be less than 400 nm, but more preferably, it should be between 135-225 nm. A concentration-enhancing polymer is then added in an amount effective to achieve concentration enhancement. Suitable concentration-enhancing polymers include HPMCAS, CAT, CAP, HPMCP and HPMC. Testing is then conducted as in Example 1 using a control that does not have the concentration-enhancing polymer.

EXAMPLE 5

A media mill equipped with a 50 ml grinding chamber ("Mini" Motormill manufactured by Eiger Machinery Inc.) can be used to manufacture nanoparticulate form of a drug. About 27 g of PVP can be dissolved in about 183 g of water and agitated in a steel vessel with a 50 mm "Cowles" type blade until the solution is clear and free of undissolved PVP polymer. The rotational speed of the mixer should be maintained at 5000 RPM. About 90 g of micronized Danazol is slowly added to this blend with the same mixing for 30 min. Then, about 200 cc of this mix is added to a holding tank of a media mill and recirculated. The mill should contain about 42.5 ml of unleaded glass beads (Glens Mills) having diameters ranging between 0.75 mm and 1.0 mm. The final average particle size should be less than about 400 nm, preferably between about 80 nm and 165 nm. A concentration-enhancing polymer is then added in an amount effective to achieve concentration enhancement. Suitable concentration-enhancing polymers include HPMCAS, CAT, CAP, HPMCP and HPMC. Testing is then conducted as in Example 1 using a control that does not have the concentration-enhancing polymer.

EXAMPLE 6

A nanoparticulate form of a steroid, 5α,17α,-1'-(methylsulfonyl)-1'H-pregn-20-yno-[3,2-c]-pyrazol-17-ol, can be prepared by ball milling with zirconium oxide grinding beads. The steroid can be prepared in the absence of a surface modifier and a post addition of Lecithin and a sonication step if required to stabilize and prevent agglomeration and rapid sedimentation. A slurry of about 5 g of unmilled coarse grains of a steroid is mixed with about 95 g high purity water with about 135 ml of Zirbeads (manufactured by Zircoa Inc.) having diameters ranging from about 0.85 mm and 1.18 mm. The slurry is then ball milled at a speed of about 86 rmp. After milling, the slurry is separated from the grinding media through a screen. About one gram of this unstabilized slurry is added to 10 g of an aqueous solution of Lecithin (1% Centrolex "P" by weight in high purity water, Lecithin manufactured by Central Soya Company, Inc.) and mixed by vigorous shaking, followed by a sonication step for 20 seconds using an ultrasonic horn (Model 350 Branson Ultrasonic Power Supply, Horn Diameter=0.5 inch (1.27 cm), Power setting=2). Milling should continue until particle size should be less than about 400 nm. A concentration-enhancing polymer is then added in an amount effective to achieve concentration enhancement. Suitable concentration-enhancing polymers include HPMCAS, CAT, CAP, HPMCP and HPMC. Testing is then conducted as in Example 1 using a control that does not have the concentration-enhancing polymer.

EXAMPLE 7

Example 6 can be repeated except that the Lecithin is replaced with the non-ionic surfactant Triton X-200 (manufactured by Rohm and Haas).

EXAMPLE 8

10 Example 6 can be repeated except that the Lecithin is replaced with gum acacia (available from Eastman Kodak Co.)

EXAMPLE 9

Example 6 can be repeated except that the Lecithin is replaced with sodium lauryl sulfate (available as Duponol ME from DuPont, Inc.).

EXAMPLE 10

Example 6 can be repeated except that the Lecithin is replaced with sodium bis(1-ethylhexyl)sulfosuccinate.

EXAMPLE 11

Example 6 can be repeated except that the Lecithin is replaced with Pluronic F68, a block copolymer of polyethylene oxide and polypropyleneoxide (available from BASF Corp.).

EXAMPLE 12

A nanoparticulate form of the steroid, 5α,17α,-1'-(methylsulfonyl)-1'H-pregn-20-yno-[3,2-c]-pyrazol-17-ol, can be prepared by ball milling with zirconium oxide grinding media. About 70 cc of Zircoa is added to a 115 cc vessel followed by about 2.5 g of a unmilled tabular crystal steroid purchased from Sterling Drug Inc. along with about 0.75 g of Pluronic F68 (BASF) and about 46.75 g high purity water. The resulting mixture is ball milled at 50% of the critical rotational speed. The mixture is then separated from the grinding media. Particle size is then measured to ensure an average particle size of less than about 400 nm. A concentration-enhancing polymer is then added in an amount effective to achieve concentration enhancement. Suitable concentration-enhancing polymers include hydroxypropyl methyl cellulose acetate succinate (HPMCAS), cellulose acetate trimellitate (CAT), cellulose acetate phthalate (CAP), hydroxypropyl methyl cellulose phthalate (HPMCP), and hydroxypropyl methyl cellulose (HPMC). Testing is then conducted as in Example 1 using a control that does not have the concentration-enhancing polymer.

EXAMPLE 13

Example 12 can be repeated except that Pluronic F68 is replaced with Centrolex® P (a lecithin derivative).

EXAMPLE 14

1 st stage: 10 g of crospovidone (Kollidon CI, BASF) is swollen by slow addition of 20 ml of a 100 mg/ml solution of griseofulvin in dimethylformamide, mixing the powder continuously in a mortar. The powder swollen in this manner is then placed in an oven under vacuum at a temperature of 100° C for about 12 hours or until completely dried.

2nd stage: 2 g of the product obtained in the first stage is disintegrated through a sieve (14 mesh) and then placed in a hermetically sealed container at ambient temperature, saturated with methylenechloride vapor from a receptacle filled with this solvent and placed in the container. After about 24 hours the powder treated in this manner is dried for about 1 hour at 30° C. in an oven under vacuum, sieved through a 14 mesh sieve and mixed for 10 minutes.

A concentration-enhancing polymer is then added in an amount effective to achieve concentration enhancement. A suitable concentration-enhancing polymer is the MF grade of hydroxypropyl methyl cellulose acetate succinate (HPMCAS-MF, available from Shin Etsu). The concentration of drug in a use environment from the resultant pharmaceutical composition can be measured as outlined supra. This can be compared to a control composition manufactured identically as above without the concentration-enhancing polymer.

EXAMPLE 15

1 st stage: 10 g of crospovidone (Knollidon CI, BASF) is swollen by slow addition of 2 ml of a 100 mg/ml solution of griseofulvin in dimethylformamide, mixing the powder continuously in a mortar. The powder swollen in this manner is then placed in an oven under vacuum at a temperature of 100° C. for about 12 hours or until completely dried.

2nd stage: 2 g of the powder obtained in the first stage is placed in a drier at ambient temperature and under an internal humidity of 90-92% obtained by an aqueous solution of suitable salts placed at the base of the same drier below the perforated floor on which the powder to be treated is placed. After about 24 hours the powder treated in this manner is dried for about 1 hour at 80° C. in an oven under vacuum, sieved through a 14 mesh sieve and mixed for 10 minutes.

A concentration-enhancing polymer is then added in an amount effective to achieve concentration enhancement. Suitable concentration-enhancing polymers include hydroxypropyl methyl cellulose acetate succinate (HPMCAS), cellulose acetate trimellitate (CAT), cellulose acetate phthalate (CAP), hydroxypropyl methyl cellulose phthalate (HPMCP), and hydroxypropyl methyl cellulose (HPMC). The concentration of drug in a use environment from the resultant pharmaceutical composition can be measured as outlined supra. This can be compared to a control composition manufactured identically as above without the concentration-enhancing polymer.

EXAMPLE 16

1 st stage: 10 g of crospovidone (Kollidon CI, BASF) is swollen by slow addition of 20 ml of a 100 mg/ml solution of griseofulvin in dimethylformamide, mixing the powder continuously in a mortar. The powder swollen in this manner is then placed in an oven under vacuum at a temperature of 100° C. for about 12 hours or until completely dried.

2nd stage: 1 g of the powder obtained in the first stage is wetted with 1 ml of demineralized water in a mortar, mixing the powder slowly for about 1.5 hours. The swollen powder is dried for about 1 hour at 80° C. in an oven under vacuum. It is then disintegrated through a 14 mesh sieve and mixed for 10 minutes.

A concentration-enhancing polymer is then added in an amount effective to achieve concentration enhancement. Suitable concentration-enhancing polymers include HPMCAS, CAT, CAP, HPMCP and HPMC. The concentration of drug in a use environment from the resultant pharmaceutical composition can be measured as outlined supra. This can be compared to a control composition manufactured identically as above without the concentration-enhancing polymer.

EXAMPLE 17

1 st stage: 500 g of crospovidone is swollen with 1000 ml of a 100 mg/ml solution of griseofulvin in dimethylformamide, this solution being added to the crospovidone kept mixing in a high-speed granulator. The swollen powder is then dried in an oven under vacuum at 100° C. for about 12 hours and then disintegrated through a 14 mesh sieve and mixed for 10 minutes.

2nd stage: 100 g of the powder obtained in the first stage is suspended in a air-operated fluidized bed (GLATT) provided with a spraying apparatus (WURSTER) and sprayed with 200 ml of demineralized water in one hour. They are then dried while remaining suspended in the fluidized bed by the flow of hot air. The powder is then recovered in the collection sleeve, disintegrated through a 14 mesh sieve and mixed for 10 minutes.

A concentration-enhancing polymer is then added in an amount effective to achieve concentration enhancement. Suitable concentration-enhancing polymers include HPMCAS, CAT, CAP, HPMCP and HPMC. The concentration of drug in a use environment from the resultant pharmaceutical composition can be measured as outlined supra. This can be compared to a control composition manufactured identically as above without the concentration-enhancing polymer.

EXAMPLE 18

1st stage: 3 g of griseofulvin is mixed with 9 g of crospovidone. One g of this mixture is placed in a rotary flask under vacuum (ROTOVAPOR) in an $N_2$ atmosphere (after evacuating the residual air) for 20 minutes under rotation while keeping the flask immersed in a silicone oil bath at 235° C. The flask is then cooled to ambient temperature, the powder extracted and sieved through a 14 mesh sieve and then mixed for 10 minutes.

2nd stage: 0.250 g of the powder obtained in the first stage were wetted in a mortar with 0.5 ml of demineralized water, mixing the system forcibly for 1.5 hours to homogeneously wet the powder. The wetted powder obtained is dried in an oven under vacuum at 80° C. for 1 hour, then disintegrated through a 14 mesh sieve and mixed for 10 minutes.

A concentration-enhancing polymer is then added in an amount effective to achieve concentration enhancement. Suitable concentration-enhancing polymers include HPMCAS, CAT, CAP, HPMCP and HPMC. The concentration of drug in a use environment from the resultant pharmaceutical composition can be measured as outlined supra. This can be compared to a control composition manufactured identically as above without the concentration-enhancing polymer.

EXAMPLE 19

3.0 g ubidecarenone is melted in a thermostatized vessel at 70° C. 1.8 g lecithin (Phospholipon 100. Naftermann) is added in the melt by sonication (Soniprep, MSE). 95.2 g bidistilled water heated to 70° C. is added to the dispersion of lecithin in molten ubidecarenone. The warm mixture is then subjected to high speed vortexing (Ultra Turrax) for 120 sec. The mixture is homogenized at 900 bar for 10 min in a high pressure homogenizer type Microfluidizer (Microfluidics Corp.) which is immersed in a water bath heated to 70° C. then allowed to stand at room temperature for cooling.

A concentration-enhancing polymer is then added in an amount effective to achieve concentration enhancement. Suitable concentration-enhancing polymers include HPMCAS, CAT, CAP, HPMCP and HPMC. The concentration of drug in a use environment from the resultant pharmaceutical composition can be measured as outlined supra. This can be compared to a control composition manufactured identically as above without the concentration-enhancing polymer.

EXAMPLE 20

3.0 g ubidecarenone is melted in a thermostatized vessel at 70° C. 1.5 g lecithin (Phospholipon 100, Nattermann) is added to the melt by sonication (Soniprep, MSE). 300 mg sodium glycocholate is dissolved in 95.2 g bidistilled water, and the solution is heated to 70° C. The heated aqueous phase is added to the mix of lecithin in molten ubidecarenone. The warm mixture is subjected to high speed vortexing (Ultra Turrax) for 120 sec. The mix is homogenized at 900 bar for 10 min in a high pressure homogenizer type Microfluidizer (Microfluidics Corp.) which is immersed in a water bath heated to 70° C. then allowed to stand at room temperature for cooling.

A concentration-enhancing polymer is then added in an amount effective to achieve concentration enhancement. Suitable concentration-enhancing polymers include HPMCAS, CAT, CAP, HPMCP and HPMC. The concentration of drug in a use environment from the resultant pharmaceutical composition can be measured as outlined supra. This can be compared to a control composition manufactured identically as above without the concentration-enhancing polymer.

EXAMPLE 21

3.0 g ubidecarenone is melted in a thermostatized vessel at 70° C. 1.8 g lecithin (Phospholipon 100, Nattermann) is added to the melt by sonication (Soniprep, MSE). 380 mg sodium glycocholate is dissolved in 94.8 g bidistilled water, and the solution is heated to 70° C. The heated aqueous phase is added to the mix of lecithin in molten ubidecarenone. The warm mixture is then subjected to high speed vortexing (Ultra Turrax) for 120 sec. The mixture is homogenized at 900 bar for 10 min in a high pressure homogenizer type Microfluidizer (Microfluidics Corp.) which is immersed in a water bath heated to 70° C. then allowed to stand at room temperature for cooling.

A concentration-enhancing polymer is then added in an amount effective to achieve concentration enhancement. Suitable concentration-enhancing polymers include HPMCAS, CAT, CAP, HPMCP and HPMC. The concentration of drug in a use environment from the resultant pharmaceutical composition can be measured as outlined supra. This can be compared to a control composition manufactured identically as above without the concentration-enhancing polymer.

EXAMPLE 22

2.5 g ubidecarenone is melted in a thermostatized vessel at 70° C. 450 mg lecithin (Phospholipon 100, Nattermann) is added to the melt by sonication (Soniprep. MSE). 210 mg sodium glycocholate is dissolved in 46.8 g bidistilled water, and the solution is heated to 70° C. The heated aqueous phase is added to the mix of lecithin in molten ubidecarenone. Probe sonication (Soniprep. MSE) for 120 min at 70° C. yields a fine mixture of ubidecarenone nanoparticles. After cooling to room temperature evaporated water is substituted. The mixture is centrifuged at 4000 rpm in a laboratory centrifuge for 20 min to remove metal shed of the sonication probe.

A concentration-enhancing polymer is then added in an amount effective to achieve concentration enhancement. Suitable concentration-enhancing polymers include HPMCAS, CAT, CAP, HPMCP and HPMC. The concentration of drug in a use environment from the resultant pharmaceutical composition can be measured as outlined supra. This can be compared to a control composition manufactured identically as above without the concentration-enhancing polymer.

EXAMPLES 23-29

For Examples 23-29, a complex of ziprasidone mesylate and sulfobutyl ether cyclodextrin (SBECD) was formed, and the complex was mixed with various concentration-enhancing polymers. The dissolution performance of each complex/polymer mixture was evaluated in in vitro tests.

The ziprasidone complex was formed using the following procedure. First, 1.1374 g SBECD was dissolved in 3.16 g water, by stirring in a 37° C. temperature-controlled chamber for about 5 minutes. Next, 0.2169 g of ziprasidone mesylate was added, and the solution was removed from the warm chamber and stirred at ambient temperature for about 1 minute. The clear solution was frozen, and the water was removed by lyophilization to obtain a dry powder. The complex contained 16.02 wt % ziprasidone mesylate, or 11.74 wt % active drug.

The dissolution of ziprasidone from the complex mixed with various concentration-enhancing polymers was evaluated in an in vitro dissolution test using a microcentrifuge method. A 6.13 mg sample of the ziprasidone complex was placed into a microcentrifuge tube with 0.061 mg (1 wt %), 0.307 mg (5 wt %), or 0.613 mg (10 wt %) of polymer. The polymer amounts are expressed as wt % based on the weight of the complex. Example 23 comprised a mixture of the complex with 1 wt % HPMCAS, MF grade (HPMCAS-MF, from Shin Etsu, Tokyo, Japan). Example 24 comprised a mixture of the complex with 5 wt % HPMCAS-MF. Example 25 comprised a mixture of the complex with 10 wt % HPMCAS-MF. Example 26 comprised a mixture of the complex with 1 wt % HPMCAS, HF grade (HPMCAS-HF, from Shin Etsu, Tokyo, Japan). Example 27 comprised a mixture of the complex with 1 wt % CAP (NF grade from Eastman Chemical Co., Kingsport, Tenn.). Example 28 comprised a mixture of the complex with 1 wt % carboxymethylethyl cellulose (CMEC) (Freund Industrial Co. Ltd., Tokyo, Japan).

Example 29 comprised a mixture of the complex with 5 wt % CMEC. Tests were performed in duplicate. The tubes were placed in a 37° C. temperature-controlled chamber, and 1.8 mL of 50 mM 4-morpholinepropanesulfonic acid (MOPS) buffer with 150 mM NaCl (pH 7.4) was added. The samples were quickly mixed using a vortex mixer for about 60 seconds. The samples were centrifuged at 13,000 G at 37° C. for 1 minute. The resulting supernatant solution was then sampled and diluted 1:4 (by volume) with methanol and then analyzed by high-performance liquid chromatography (HPLC). A Phenomenex Ultracarb 5 ODS HPLC column was used with a mobile phase of 60 vol. % of 0.02 M $KH_2PO_4$ (pH 3.0), and 40 vol. % acetonitrile. UV detection was measured at 254 nm. The contents of the tubes were mixed on the vortex mixer and allowed to stand undisturbed at 37° C. until the next sample was taken. Samples were collected at 4, 10, 30, 60, and 90 minutes. For Control 1 (C1), 6.13 mg of ziprasidone complex was tested without concentration-enhancing polymer in the test solution. °Control 2 (C2) consisted of 0.982 mg ziprasidone mesylate alone. The concentrations of drug obtained in these samples are shown below.

TABLE 1

| Example | Time (min) | Ziprasidone Concentration (μg/mL) | AUC (min*μg/mL) |
|---|---|---|---|
| 23 SBECD complex + 1 wt % HPMCAS-MF | 0 | 0 | 0 |
|  | 4 | 204 | 400 |
|  | 10 | 88 | 1300 |
|  | 30 | 64 | 2800 |
|  | 60 | 70 | 4800 |
|  | 90 | 62 | 6800 |
| 24 SBECD complex + 5 wt % HPMCAS-MF | 0 | 0 | 0 |
|  | 4 | 227 | 500 |
|  | 10 | 172 | 1700 |
|  | 30 | 53 | 3900 |
|  | 60 | 29 | 5100 |
|  | 90 | 50 | 6300 |
| 25 SBECD complex + 10 wt % HPMCAS-MF | 0 | 0 | 0 |
|  | 4 | 254 | 500 |
|  | 10 | 202 | 1900 |
|  | 30 | 48 | 4400 |
|  | 60 | 39 | 5700 |
|  | 90 | 33 | 6800 |
| 26 SBECD complex + 1 wt % HPMCAS-HF | 0 | 0 | 0 |
|  | 4 | 194 | 400 |
|  | 10 | 78 | 1200 |
|  | 30 | 26 | 2200 |
|  | 60 | 24 | 3000 |
|  | 90 | 18 | 3600 |
| 27 SBECD complex + 1 wt % CAP | 0 | 0 | 0 |
|  | 4 | 196 | 400 |
|  | 10 | 132 | 1400 |
|  | 30 | 82 | 3500 |
|  | 60 | 44 | 5400 |
|  | 90 | 58 | 6900 |
| 28 SBECD complex + 1 wt % CMEC | 0 | 0 | 0 |
|  | 4 | 236 | 500 |
|  | 10 | 92 | 1500 |
|  | 30 | 43 | 2800 |
|  | 60 | 49 | 4200 |
|  | 90 | 47 | 5600 |
| 29 SBECD complex + 5 wt % CMEC | 0 | 0 | 0 |
|  | 4 | 276 | 600 |
|  | 10 | 174 | 1900 |
|  | 30 | 46 | 4100 |
|  | 60 | 41 | 5400 |
|  | 90 | 46 | 6700 |
| C1 SBECD complex | 0 | 0 | 0 |
|  | 4 | 12 | 0 |
|  | 10 | 10 | 100 |
|  | 30 | 7 | 300 |
|  | 60 | 6 | 500 |
|  | 90 | 8 | 700 |
| C2 Ziprasidone Mesylate | 0 | 0 | 0 |
|  | 4 | 3 | 0 |
|  | 10 | 1 | 0 |
|  | 30 | 1 | 0 |
|  | 60 | 1 | 0 |
|  | 90 | 1 | 100 |

Results from dissolution tests of Examples 23-29, and Controls C1 and C2, are summarized in Table 2.

TABLE 2

| Example | Concentration Enhancing Polymer* | Amount of Polymer (wt % of complex) | $C_{max,90}$ (μg/mL) | $AUC_{90}$ (min*μg/mL) |
|---|---|---|---|---|
| 23 | HPMCAS-MF | 1 | 204 | 6800 |
| 24 | HPMCAS-MF | 5 | 227 | 6300 |
| 25 | HPMCAS-MF | 10 | 254 | 6800 |
| 26 | HPMCAS-HF | 1 | 194 | 3600 |
| 27 | CAP | 1 | 196 | 6900 |
| 28 | CMEC | 1 | 236 | 5600 |
| 29 | CMEC | 5 | 276 | 6700 |
| C1 SBECD complex | none | — | 12 | 700 |
| C2 ziprasidone mesylate | none | — | 3 | 100 |

*Polymer designations: HPMCAS = hydroxypropylmethyl cellulose acetate succinate, CAP = cellulose acetate phthalate, CMEC = carboxymethylethyl cellulose.

As can be seen from the data in Table 2, the ziprasidone complex mixed with concentration-enhancing polymers provides $C_{max90}$ values 16- to 23-fold that of the complex alone, and $AUC_{90}$ values 5- to 10-fold that of the complex alone. The dissolution performance of the complex (C1) compared to drug alone (C2) shows that the complex is a solubility-improved form.

EXAMPLES 30-33

For Examples 30-33, complexes of ziprasidone mesylate were formed with various cyclodextrins, and the complexes were each mixed with 1 wt % HPMCAS-MF as the concentration-enhancing polymer. The dissolution performance of each complex/polymer mixture was evaluated in in vitro tests.

The ziprasidone complexes were formed by mixing drug, cyclodextrin, and polymer together in a microcentrifuge tube. The amounts of drug and cyclodextrin were chosen to yield a molar ratio of 1/1.25 drug/cyclodextrin. HPMCAS was added in an mount to equal 1 wt % of the total weight of the complex. Example 30 comprised a mixture of 0.982 mg ziprasidone mesylate, 4.715 mg SBECD, and 0.057 mg HPMCAS-MF. Example 31 comprised a mixture of 0.982 mg ziprasidone mesylate, 2.853 mg hydroxypropyl β-cyclodextrin (HPCD), and 0.038 mg HPMCAS-MF. Example 32 comprised a mixture of 0.982 mg ziprasidone mesylate, 2.474 mg β-cyclodextrin, and 0.035 mg HPMCAS-MF. Example 33 comprised a mixture of 0.982 mg ziprasidone mesylate, 2.827 mg γ-cyclodextrin, and 0.038 mg HPMCAS-MF. Control 3 (C3) comprised a mixture of ziprasidone mesylate and SBECD without concentration-enhancing polymer. Control 4 (C4) comprised a mixture of ziprasidone mesylate and HPCD without concentration-enhancing polymer. β-cyclodextrin and γ-cyclodextrin complexes were not tested without concentration-enhancing polymer.)

The dissolution of ziprasidone from these complexes mixed with concentration-enhancing polymer was evaluated using the in vitro dissolution test described in the Examples above. The results are shown in Table 3.

TABLE 3

| Example | Time (mins) | Ziprasidone Concentration (μg/mL) | AUC (min*μg/mL) |
|---|---|---|---|
| 30 | 0 | 0 | 0 |
| SBECD complex + 1 wt % | 4 | 167 | 300 |
| HPMCAS-MF | 10 | 82 | 1100 |
|  | 30 | 31 | 2200 |
|  | 60 | 26 | 3100 |
|  | 90 | 18 | 3700 |
| 31 | 0 | 0 | 0 |
| HPCD complex + 1 wt % | 4 | 52 | 100 |
| HPMCAS-MF | 10 | 20 | 300 |
|  | 30 | 35 | 900 |
|  | 60 | 30 | 1800 |
|  | 90 | 17 | 2600 |
| 32 | 0 | 0 | 0 |
| β-CD complex + 1 wt % | 4 | 26 | 100 |
| HPMCAS-MF | 10 | 34 | 200 |
|  | 30 | 29 | 900 |
|  | 60 | 36 | 1800 |
|  | 90 | 17 | 2600 |
| 33 | 0 | 0 | 0 |
| γ-CD complex + 1 wt % | 4 | 14 | 0 |
| HPMCAS-MF | 10 | 4 | 100 |
|  | 30 | 18 | 300 |
|  | 60 | 10 | 700 |
|  | 90 | 10 | 1000 |
| C3 | 0 | 0 | 0 |
| SBECD complex | 4 | 9 | 0 |
|  | 10 | 11 | 100 |
|  | 30 | 5 | 200 |
|  | 60 | 10 | 500 |
|  | 90 | 6 | 700 |
| C4 | 0 | 0 | 0 |
| HPCD complex | 4 | 10 | 0 |
|  | 10 | 6 | 100 |
|  | 30 | 6 | 100 |
|  | 60 | 16 | 300 |
|  | 90 | 15 | 1100 |

Results from dissolution tests of Examples 30-33, and Controls C3 and C4, are summarized in Table 4.

TABLE 4

| Example | Cyclodextrin | $C_{max,90}$ (μg/mL) | $AUC_{90}$ (min*μg/mL) |
|---|---|---|---|
| 30 | SBECD | 167 | 3700 |
| 31 | HPCD | 52 | 2600 |
| 32 | β-CD | 36 | 2600 |
| 33 | γ-CD | 18 | 1000 |
| C3 no polymer | SBECD | 11 | 700 |
| C4 no polymer | HPCD | 16 | 1100 |

As can be seen from the data in Table 4, the ziprasidone SBECD complex mixed with concentration-enhancing polymer provides a $C_{max90}$ 15.2-fold that of Control C3, and an $AUC_{90}$ 5.3-fold that of Control C3. The ziprasidone HPCD complex mixed with concentration-enhancing polymer provides a $C_{max90}$ 3.3-fold that of Control $C_4$, and an $AUC_{90}$ 2.4-fold that of Control C4. Examples 32 and 33 provided $C_{max90}$ values 12- and 6-fold that of the drug alone (C2, Table 2), and $AUC_{90}$ values 26- and 10-fold that of the drug alone.

The invention has been described in detail with particular reference to particular embodiments thereof, but it will be understood that variations and modifications can be effected within the spirit and scope of the invention.

The invention claimed is:
1. A composition comprising:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer selected from the group consisting of hydroxypropyl methyl cellulose acetate succinate, cellulose acetate phthalate, hydroxypropyl methyl cellulose phthalate, and cellulose acetate trimellitate wherein said concentration-enhancing polymer is present in a sufficient amount so that said composition provides, after introduction to said use environment, a maximum concentration of said drug in said use environment that is at least 1.25-fold a maximum concentration of said drug provided by a control composition, wherein said control composition is an equivalent quantity of said drug in said solubility-improved form alone;
wherein said solubility-improved form is selected from the group consisting of drug in nanoparticulate form, absorbed drug, drug in a nanosuspension, a supercooled melt of drug, cyclodextrin/drug form, gelatin form, softgel form, and three phase form; and
wherein said drug in said nanoparticulate form comprises a surface modifier adsorbed on said surface of said drug, and said concentration enhancing polymer is separate from said surface modifier.

2. A composition comprising:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer selected from the group consisting of hydroxypropyl methyl cellulose acetate succinate, cellulose acetate phthalate, hydroxypropyl methyl cellulose phthalate, and cellulose acetate trimellitate;
wherein said concentration-enhancing polymer is present in a sufficient amount so that said composition provides, after introduction to a use environment, a dissolution area under the concentration versus time curve for any period of at least 90 minutes between the time of introduction into the use environment and about 270 minutes following introduction to the use environment that is at least 1.25-fold the corresponding area under the curve provided by a control composition, wherein said control composition is an equivalent quantity of said drug in said solubility-improved form alone; and
wherein said solubility-improved form is selected from the group consisting of drug in nanoparticulate form, absorbed drug, drug in a nanosuspension, a supercooled melt of drug, cyclodextrin/drug form, gelatin form, softgel form, and three phase form; and wherein said drug in said nanoparticulate form comprises a surface modifier adsorbed on said surface of said drug, and said concentration enhancing polymer is separate from said surface modifier.

3. A composition comprising:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer selected from the group consisting of hydroxypropyl methyl cellulose acetate succinate, cellulose acetate phthalate, hydroxypropyl methyl cellulose phthalate, and cellulose acetate trimellitate;
wherein said concentration-enhancing polymer is present in a sufficient amount so that said composition provides, after introduction to said use environment, a relative bioavailability of at least 1.25 relative to a control composition, wherein said control composition is an equivalent quantity of said drug in said solubility-improved form alone; and
wherein said solubility-improved form is selected from the group consisting of drug in nanoparticulate form, absorbed drug, drug in a nanosuspension, a supercooled melt of drug, cyclodextrin/drug form, gelatin form, softgel form, and three phase form; and
wherein said drug in said nanoparticulate form comprises a surface modifier adsorbed on said surface of said drug, and said concentration enhancing polymer is separate from said surface modifier.

4. The composition of any one of claims 1, 2 and 3 wherein said solubility-improved drug form is said cyclodextrin/drug form.

5. The composition of any one of claims 1, 2 and 3 wherein said solubility-improved drug form is said cyclodextrin/drug form, said drug is ziprasidone[, and said polymer is selected from the group consisting of hydroxypropyl methyl cellulose acetate succinate, cellulose acetate phthalate, and carboxymethyl ethyl cellulose].

6. A method of administering a low-solubility drug comprising co-administering:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer selected from the group consisting of hydroxypropyl methyl cellulose acetate succinate, cellulose acetate phthalate, hydroxypropyl methyl cellulose phthalate, and cellulose acetate trimellitate;
wherein said concentration-enhancing polymer is co-administered with said drug in a sufficient amount, so that after introduction to said use environment, a maximum concentration of said drug in said use environment is provided that is at least 1.25-fold a maximum concentration of said drug provided by a control composition, wherein said control composition is an equivalent quantity of said drug in said solubility-improved form alone.

7. A method of administering a low-solubility drug comprising co-administering:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer selected from the group consisting of hydroxypropyl methyl cellulose acetate succinate, cellulose acetate phthalate, hydroxypropyl methyl cellulose phthalate, and cellulose acetate trimellitate;
wherein said concentration-enhancing polymer is co-administered with said drug in a sufficient amount so that, after introduction to said environment, a dissolution area under the concentration versus time curve for any period of at least 90 minutes between the time of introduction into the use environment and about 270 minutes following introduction to the use environment is provided that is at least 1.25-fold the corresponding area under the curve provided by a control composition; and
wherein said control composition is an equivalent quantity of said drug in said solubility-improved form alone.

8. A method of administering a low-solubility drug comprising co-administering:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer selected from the group consisting of hydroxypropyl methyl cellulose acetate succinate, cellulose acetate phthalate, hydroxypropyl methyl cellulose phthalate, and cellulose acetate trimellitate;
wherein said concentration-enhancing polymer is co-administered with said drug in a sufficient amount so that, after introduction to said use environment, a relative bioavailability is provided that is at least 1.25-fold that of a control composition, wherein said control composition is an equivalent quantity of said drug in said solubility-improved form alone.

9. A composition comprising:
(a) a drug in a solubility-improved form which provides, when administered to a use environment, at least one of a dissolved drug concentration in said use environment that exceeds an equilibrium concentration of a lowest solubility form of said drug in said use environment and a dissolution rate that exceeds a dissolution rate of said lowest solubility form of said drug in said use environment; and
(b) a concentration-enhancing polymer wherein said concentration-enhancing polymer is present in a sufficient amount so that said composition provides, after introduction to said use environment, a maximum concentration of said drug in said use environment that is at least 1.25-fold a maximum concentration of said drug provided by a control composition, wherein said control composition is an equivalent quantity of said drug in said solubility-improved form alone;
wherein said solubility-improved form is selected from the group consisting of drug in softgel form and self-emulsifying form, and wherein said polymer is selected from the group consisting of hydroxypropyl methyl cellulose acetate succinate, [hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, ethyl carboxymethyl cellulose, carboxymethyl cellulose, carboxymethyl ethyl cellulose,] cellulose acetate phthalate, [methyl cellulose acetate phthalate, ethyl cellulose acetate phthalate, hydroxypropyl cellulose acetate phthalate,] hydroxypropyl methyl cellulose acetate phthalate, [hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate,] and cellulose acetate trimellitate, [methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate, and neutralized forms thereof].

10. The composition of any one of claims 1, 2 and 3 wherein said drug is ziprasidone.

* * * * *